United States Patent [19]

Yamada et al.

[11] Patent Number: 5,789,139
[45] Date of Patent: Aug. 4, 1998

[54] HYDRAZIDE COMPOUND AND SILVER HALIDE PHOTOGRAPHIC PHOTOSENSITIVE MATERIAL COMPRISING THE SAME

[75] Inventors: Kohzaburoh Yamada; Hiroyuki Suzuki; Toshihide Ezoe; Koji Kawato, all of Kanagawa, Japan

[73] Assignee: Fuji Photo Film Co., Ltd., Kanagawa, Japan

[21] Appl. No.: 774,360

[22] Filed: Dec. 27, 1996

[30] Foreign Application Priority Data

| Dec. 27, 1995 | [JP] | Japan | 7-351132 |
| Dec. 27, 1995 | [JP] | Japan | 7-351168 |
| Dec. 27, 1995 | [JP] | Japan | 7-351269 |
| Feb. 16, 1996 | [JP] | Japan | 8-052516 |
| Oct. 25, 1996 | [JP] | Japan | 8-283817 |
| Oct. 25, 1996 | [JP] | Japan | 8-299878 |

[51] Int. Cl.$^6$ .................................................. G03C 1/43
[52] U.S. Cl. .......................... 430/264; 430/448; 564/310; 564/311; 564/313
[58] Field of Search ........................ 430/264, 448; 564/310, 311, 313

[56] References Cited

U.S. PATENT DOCUMENTS

| 5,212,045 | 5/1993 | Koga et al. | 430/264 |
| 5,279,920 | 1/1994 | Onodera et al. | 430/264 |
| 5,378,578 | 1/1995 | Hoshimiya et al. | 430/264 |

FOREIGN PATENT DOCUMENTS

WO9532453  11/1995  WIPO.

*Primary Examiner*—Hoa Van Le
*Attorney, Agent, or Firm*—Sughrue, Mion, Zinn, Macpeak & Seas, PLLC

[57] ABSTRACT

A hydrazide compound represented by the following formula (I), and a silver halide photographic photonsensitive material comprising the hydrazide compound:

$$A-(B)_b \qquad (I)$$

wherein A represents a heterocyclic group, a condensed polycyclic aromatic group or a group formed by connecting at least two aromatic groups to each other, B represents a group represented by the following formula (I-B) or (II-B), and b represents an integer from 2 to 6;

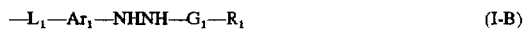

$$-L_1-Ar_1-NHNH-G_1-R_1 \qquad (I-B)$$

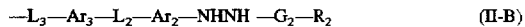

$$-L_3-Ar_3-L_2-Ar_2-NHNH-G_2-R_2 \qquad (II-B)$$

wherein each of $G_1$ and $G_2$ represents a carbonyl group, an oxalyl group, a sulfonyl group or a phosphoryl group; each of $R_1$ and $R_2$ represents a hydrogen atom or a blocking group; each of $Ar_1$, $Ar_2$ and $Ar_3$ represents an aromatic group or an aromatic heterocyclic group; and each of $L_1$, $L_2$ and $L_3$ represents a linkage group.

2 Claims, No Drawings

HYDRAZIDE COMPOUND AND SILVER HALIDE PHOTOGRAPHIC PHOTOSENSITIVE MATERIAL COMPRISING THE SAME

FIELD OF THE INVENTION

The present invention relates to a hydrazide compound having a particular structure and a silver halide photographic photosensitive material comprising the hydrazide compound.

BACKGROUND OF THE INVENTION

In the field of graphic arts, an image forming system capable of providing ultra-hard photographic characteristics (especially a gamma value of not lower than 10) is required for satisfactory halftone-image reproduction from a continuous tone image or line original. Further, it is requested to find an image forming system in which development is carried out using a processing solution having high storage stability, and yet ultra-hard photographic characteristics are obtained. For instance, the system of forming an ultra-hard negative image having a gamma value higher than 10 by processing a surface latent-image type photographic photosensitive material, to which a special acylhydrazine compound is added, with a developer containing a sulfite preservative in a concentration of at least 0.15 mole/l and adjusted to pH 11.0–12.3 has been reported, e.g., in U.S. Pat. Nos. 4,166,742, 4,168,977, 4,221,857, 4,224,401, 4,243,739, 4,272,606 and 4,311,781. Although only the use of silver chlorobromide having a high chloride content is allowed in conventional methods of forming ultra-hard images, the new image formation system mentioned above has an advantage of allowing the use of silver iodobromide and silver chloroiodobromide also. In addition, such an image formation system is also characterized by relatively good storage stability due to a high content of sulfite preservative in the developer used, as compared with conventional with developer which permits the presence of a extremely slight amount of sulfite preservative. However, developers above the pH 11 are unstable due to liability to air oxidation, so that they cannot withstand long-term storage and use. Thus, it has been attempted to devise a means to form high-contrast images by developing a hydrazine compound-containing silver halide photographic photosensitive material with a developer below the aforesaid pH value. For instance, JP-A-01-179939 and JP-A-01-179940 describe the measures in which a photographic photosensitive material comprising a nucleation development accelerator having a group capable of being adsorbed by silver halide grains and a nucleating agent having such an adsorbable group is processed with a developer below the pH of 11.0. However, since the emulsions used therein are a silver bromide emulsion and a silver iodobromide emulsion, photographic properties are changed greatly by variations in progress of development and compositions of processing solutions. Therefore, those measures cannot be said to be sufficient with respect to consistency.

Further, the hydrazine compounds containing repeating units of ethylene oxide and the hydrazine compounds having pyridinium groups are disclosed in U.S. Pat. Nos. 4,998,604, 4,994,365 and 4,975,354. Judging from the descriptions in Examples thereof, however, the contrast attained is not high enough, and it is difficult to achieve high contrast and desired Dmax under practical development conditions. In addition, the nucleation hard photosensitive materials using hydrazine derivatives have photographic properties greatly varying with the pH of a developer used. The pH of a developer fluctuates greatly, e.g., through a rise caused by air oxidation of the developer and concentration of the developer due to evaporation of water, and a drop caused by absorption of carbon dioxide in the air. Accordingly, it has been attempted to devise a means to minimize the influence of developer's pH upon photographic properties.

On the other hand, photosensitive materials for dot to dot work, which are generally handled in an illuminated room hold a large field as the photosensitive materials for plate making. In this sphere, reverse image quality high enough to reproduce even Ming-style slender chinese characters is required. In order to meet this requirement, it has been desired to seek for a nucleating agent of higher activity. In particular, it is difficult for low-speed photosensitive materials having illuminated room processing suitability to heighten their contrast by the use of a nucleating agent. Therefore, the development of a nucleating agent having much higher activity has been expected.

With the intention of achieving such a purpose, the hydrazine compounds disclosed, e.g., in JP-A-06-148828, JP-A-06-180477 and JP-A-06-194774 have been developed as highly active nucleating agent.

In particular, nucleating agents which contain in their acyl group an alkyl moiety substituted with at least one electron-withdrawing group are favorable ones, because they can provide a very high-contrast, photographic characteristic even when a developer below pH 11 is used, and brings about a slight change in photographic properties even when an exhausted developer is used. Among those agents, however, some nucleating agents themselves are subject to oxidation, and so it is required for them to make an improvement in keeping quality.

Further, the compounds having two hydrazino groups per molecule are disclosed in JP-A-64-86134, JP-A-04-16938 and JP-A-05-197091. In particular, JP-A-05-197091 discloses several compounds which are superior in high contrast properties to conventional acylhydrazine compounds having the same acyl groups respectively. Even those compounds are not wholly satisfactory with respect to high contrast achieved by the use of a developer below pH 11, stability to variation factors of processing solutions, keeping quality and so on, so that it is required for them to undergo improvements.

On the other hand, the method of forming a direct-positive image by processing an internal latent-image type silver halide photographic emulsion with a surface developer in the present of a nucleating agent, and the photographic emulsions or the photosensitive materials usable therein are known, e.g., in U.S. Pat. Nos. 2,456,953, 2,497,875, 2,497, 876, 2,588,982, 2,592,250, 2,675,318, 3,227,552 and 3,317, 322, British Patents 1,011,062, 1,151,363, 1,269,649 and 2,011,391, JP-B-43-29405, JP-B-49-38164, JP-B-53-16623, JP-B-53-137133, JP-B-54-37732, JP-B-54-40629, JP-B-54-74536, JP-B-54-74729, JP-B-55-52055 and JP-B-55-90940.

In the foregoing method of forming a direct-positive image, the nucleating agent may be added to the developer, but it is a more general way to incorporate the nucleating agent in a photographic emulsion layer or another appropriate layer of the photosensitive material.

As for the nucleating agent incorporated in a direct-positive silver halide photosensitive material, hydrazine compounds are the best-known examples thereof. Specifically, such hydrazine compounds include those recited in Research Disclosure, No. 23510 (November, 1983), ibid., No. 15162 (Vol. 151, November, 1976), and ibid., No. 17626 (Vol. 176, December, 1978). In general, hydrazine nucleation agents are most excellent with respect to discrimination since they can ensure a great difference between the maximum density (Dmax) and the minimum density (Dmin), but they have a disadvantage of requiring high pH (11 or higher) for processing. Thus, it has also been expected to introduce improvements therein.

SUMMARY OF THE INVENTION

Therefore, a first object of the present invention is to provide a silver halide photographic photosensitive material which can exhibit ultra-hard photographic characteristics, such as a gamma higher than 10, upon processing with a stable developer.

A second object of the present invention is to provide a silver halide photographic photosensitive material for plate making which has high processing stability and excellent keeping quality.

A third object of the present invention is to provide a direct-positive photosensitive material which can achieve sufficient reversal effect despite the small-amount addition of a nucleation agent thereto and the use of a processing solution having a low pH value.

A fourth object of the present invention is to provide a hydrazide compound having a particular structure which is useful for the accomplishment of the above-mentioned objects.

The present objects as described above are attained with a silver halide photographic photosensitive material comprising a hydrazide compound represented by the following formula (I):

A—(B)$_b$      (I)

wherein A represents a heterocyclic group, a condensed polycyclic aromatic group or a group formed by connecting at least two aromatic groups to each other, B represents a group represented by the following formula (I-B) or (II-B), and b represents an integer from 2 to 6;

—L$_1$—Ar$_1$—NHNH—G$_1$—R$_1$      (I-B)

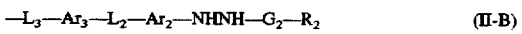

—L$_3$—Ar$_3$—L$_2$—Ar$_2$—NHNH—G$_2$—R$_2$      (II-B)

wherein each of G$_1$ and G$_2$ represents a carbonyl group, an oxalyl group, a sulfonyl group or a phosphoryl group; each of R$_1$ and R$_2$ represents a hydrogen atom or a blocking group; each of Ar$_1$, Ar$_2$ and Ar$_3$ represents an aromatic group or an aromatic heterocyclic group; and each of L$_1$, L$_2$ and L$_3$ represents a linkage group.

DETAILED DESCRIPTION OF THE INVENTION

The compound of the present invention is illustrated below in detail.

The heterocyclic group represented by A in formula (I) is a saturated or unsaturated, 3- to 7-membered, at least one N, O or S atom-containing, monocyclic or condensed heterocyclic group, to which another cyclic hydrocarbon or hetero ring may further be connected via a single bond or a divalent organic group.

Specific examples of the saturated or non-aromatic unsaturated heterocyclic group include an oxoran ring, a thiolane ring, a pyrrolidine ring, a 1,4-dioxane ring, a 1,4-dithiane ring, a 2,4,8,10-tetraoxaspiro-(5,5)undecane ring, a piperidine ring, a piperazine ring, an indoline ring, a 1,3-benzodioxole ring, a 1,2,4,5-benzenetetracarboxydiimide ring, a 1,4,5,8-naphthalenetetracarboxylic acid diimide ring and biphthalimide ring.

Specific examples of the aromatic heterocyclic group include a pyridine ring, an imidazole ring, a quinoline ring, a benzimidazole ring, a pyrimidine ring, a pyrazole ring, a triazine ring, an isoquinoline ring, a thiazole ring, a benzothiazole ring, a benzoxazole ring, a quinoxaline ring, an acridine ring, a carbazole ring, a dibenzothiophene-5,5-dioxide ring and a 1,10-phenanthroline ring.

Specific examples of the heterocyclic group connected to another cyclic hydrocarbon or hetero ring via a single bond or a divalent organic group include 2,2'-bipyridine, 4,4'-bipyridine, 2,2'-biquinoline, 4,4'-biphthalimide, stilbazole, 2,2'-bithienyl, 2,2'-dithiobispyridine, 2,2':6',2''-terpyridine and 4,4'-trimethylenedipyridine.

Additionally, the heterocyclic group represented by A in formula (I) includes no heterocyclic group of the type which contains a quaternarized nitrogen atom.

The group represented by A in formula (I) may have a substituent.

Examples of the condensed polycyclic aromatic group represented by A in formula (I) include naphthalene, triphenylene, indane, anthracene, perylene, phenanthrene and fluorenone rings respectively-are examples thereof. Of these groups, those derived from naphthalene and triphenylene rings respectively are preferred over the others. Of these, a naphthalene ring is particularly preferred.

A in formula (I) may also represent a group formed by connecting at least two aromatic groups to one another.

The term "aromatic group" as used herein means monocyclic and dicyclic aryl groups. Substituted or unsubstituted phenyl or naphthyl groups are specific examples thereof.

In the group represented by A in formula (I), which is formed by connecting two or more of those aromatic groups to one another, adjacent aromatic groups are connected by a single bond or a divalent organic group, but they are not fused together.

Specific examples of the divalent organic group include a single bond, —O—, —N(R$_{Nd}$)—, —SO$_2$—, —C(R$_{C1}$)(R$_{C2}$)—, —CO—, —C(=S)—, —C=C—, —C≡C— and —N=N—, with the proviso that the divalent organic group excludes —S—, wherein R$_{Nd}$ represents a single bond, a hydrogen atom, an alkyl group, an aryl group, an acyl group, an alkylsulfonyl group, an arylsulfonyl group, a carbamoyl group or an oxycarbonyl group, and R$_{C1}$ and R$_{C2}$ each represent a hydrogen atom, an alkyl group or an aryl group. When each of R$_{Nd}$, R$_{C1}$ and R$_{C2}$ represents an alkyl group, it is preferable for the alkyl group to be a substituted or unsubstituted alkyl group containing 1 to 8 carbon atoms in all. When each of them represents an aryl group, it is preferable for the aryl group to be a substituted or unsubstituted aryl group containing 6 to 12 carbon atoms in all, especially a substituted or unsubstituted phenyl group. The groups represented by R$_{Nd}$, R$_{C1}$ and R$_{C2}$ respectively are not permitted to contain as their substituents the groups represented by B in formula (I).

Of the two or more of aromatic groups connected by single bond(s) or divalent organic group(s), which is represented by A in formula (I), at least two aromatic groups each link with at least one group represented by B in formula (I).

Specific examples of the group represented by A, which is formed by connecting at least two aromatic groups to one another in formula (I) include the groups illustrated below:

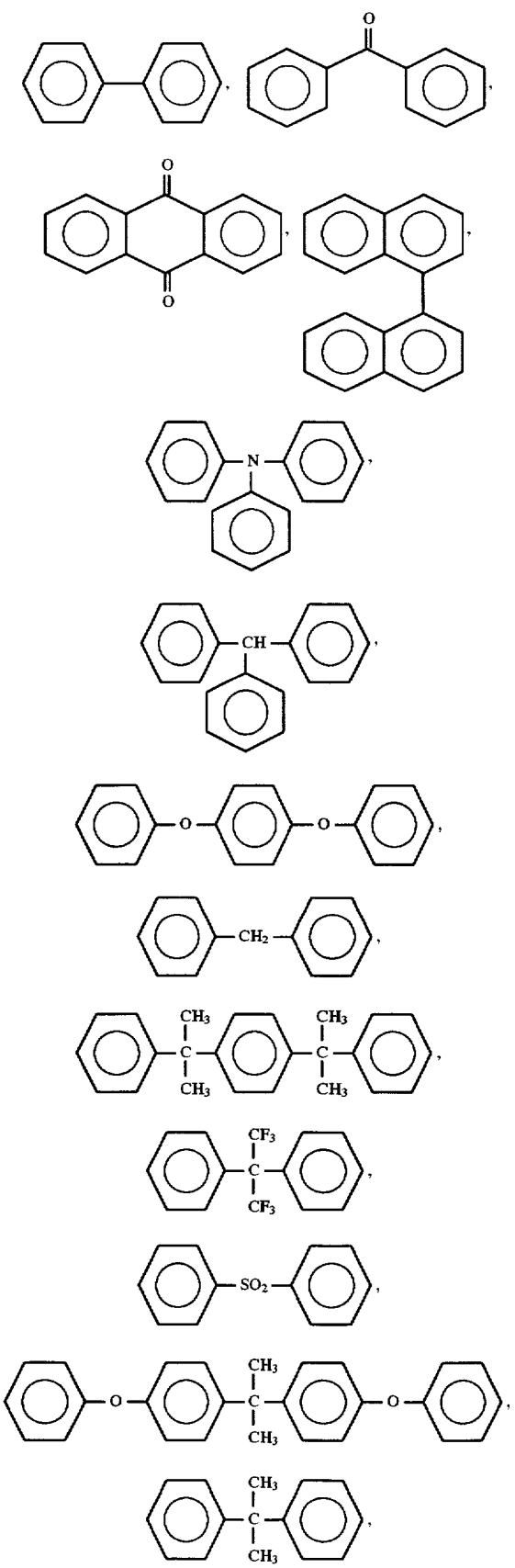
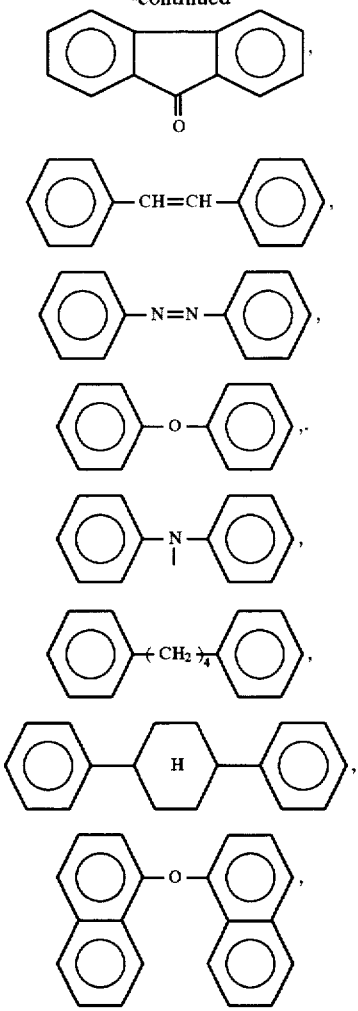

The groups preferred as A in formula (I) are groups in which two or three benzene rings are present and the adjacent rings are connected by a single bond or a divalent organic group.

The substituent which A may have includes a halogen atom and a group capable of being attached to a ring or a main chain via its carbon, oxygen, nitrogen or sulfur atom. Examples of the group to be attached via its carbon atom include an alkyl group, an alkenyl group, an alkynyl group, an aryl group, a carbamoyl group, an alkoxycarbonyl group, an aryloxycarbonyl group, an acyl group, an acylcarbamoyl group, a sulfonylcarbamoyl group, a carboxyl or carboxylate group, a cyano group and a heterocyclic group. Examples of the group to be attached via its oxygen atom include a hydroxy group, an alkoxy group, an aryloxy group, a heterocyclic oxy group, an acyloxy group, a carbamoyloxy group and a sulfonyloxy group. Examples of the group to be attached via its nitrogen atom include an acylamino group, an amino group, an alkylamino group, an arylamino group, a heterocyclic amino group, an ureido group, a sulfamoylamino group, an alkoxycarbonylamino group, an aryloxycarbonylamino group, a sulfonamido group, an imido group and a heterocyclic group. Examples of the group to be attached via its sulfur atom include a mercapto group, an alkylthio group, an arylthio group, a heterocyclic thio group, a sulfamoyl group, an acylsulfamoyl group, an alkoxysulfonyl group, an aryloxysulfonyl group, a sulfonyl group, a sulfo or sulfonate group and a sulfinyl group. Those groups each may further be substituted with a group as recited above.

Further details of the above-described substituents are described below. The halogen atom includes a fluorine atom, a chlorine atom and a bromine atom. The alkyl group includes straight-chain, branched and cyclic alkyl groups containing 1 to 16 carbon atoms, preferably 1 to 10 carbon atoms, such as methyl, ethyl, isopropyl, t-butyl, benzyl and cyclopentyl groups. The alkenyl group includes those containing 2 to 16 carbon atoms, such as vinyl, 1-propenyl, 1-hexenyl and styryl groups. The alkynyl group includes those containing 2 to 16 carbon atoms, such as ethynyl, 1-butynyl, 1-dodecynyl and phenylethynyl groups. The aryl group includes those containing 6 to 24 carbon atoms, such as phenyl, naphthyl and p-methoxyphenyl groups.

The carbamoyl group includes those containing 1 to 18 carbon atoms, such as carbamoyl, N-ethylcarbamoyl, N-octylcarbamoyl and N-phenylcarbamoyl groups. The alkoxycarbonyl group includes those containing 2 to 18 carbon atoms, such as methoxycarbonyl and benzyloxycarbonyl groups. The aryloxycarbonyl group includes those containing 7 to 18 carbon atoms, such as a phenoxycarbonyl group. The acyl group includes those containing 1 to 18 carbon atoms, such as acetyl and benzoyl groups. The heterocyclic group whose connective atom is a carbon atom on the ring includes 5- or 6-membered, saturated or unsaturated heterocyclic groups which contain in their individual rings 1 to 5 carbon atoms and at least one oxygen, nitrogen or sulfur atom. As for the hetero atom(s) in such a heterocyclic group, the number thereof may be one or more, and the kind thereof may be the same or different. Specific examples of such a heterocyclic group include 2-furyl, 2-thienyl, 2-pyridyl and 2-imidazolyl groups. The acylcarbamoyl group includes those containing 1 to 18 carbon atoms, such as N-acetylcarbamoyl and N-benzoylcarbamoyl groups. The sulfonylcarbamoyl group includes those containing 1 to 18 carbon atoms, such as N-methanesulfonylcarbamoyl and N-benzenesulfonylcarbamoyl groups.

The alkoxy group includes those containing 1 to 16 carbon atoms, preferably 1 to 10 carbon atoms, such as methoxy, 2-methoxyethoxy and 2-methanesulfonylethoxy groups. The aryloxy group includes those containing 6 to 24 carbon atoms, such as phenoxy, p-methoxyphenoxy and m-(3-hydroxypropionamido) phenoxy groups. The hetrocyclic oxy group includes 5- or 6-membered, saturated or unsaturated heterocyclic oxy groups which contain in their individual rings 1 to 5 carbon atoms and at least one oxygen, nitrogen or sulfur atom. Therein, the number of ring-constituting hetero atom(s) may be one or more and the kind thereof may be the same or different. Specific examples of such a heterocyclic oxy group include 1-phenyltetrazolyl-5-oxy, 2-tetrahydropyranyloxy and 2-pyridyloxy groups. The acyloxy group includes those containing 1 to 16 carbon atoms, preferably 1 to 10 carbon atoms, such as acetoxy, benzoyloxy and 4-hydroxybutanoyloxy groups. The carbamoyloxy group includes those containing 1 to 16 carbon atoms, preferably 1 to 10 carbon atoms, such as N,N-dimethylcarbamoyloxy, N-hexylcarbamoyloxy and N-phenylcarbamoyloxy groups. The sulfonyloxy group includes those containing 1 to 16 carbon atoms, such as methanesulfonyloxy and benzenesulfonyloxy groups.

The acylamino group includes those containing 1 to 16 carbon atoms, preferably 1 to 10 carbon atoms, such as acetamido and p-chlorobenzoylamido groups. The alkylamino group includes those containing 1 to 16 carbon atoms, preferably 1 to 10 carbon atoms, such as N,N-dimethylamino and N-(2-hydroxyethyl)amino groups. The arylamino group includes those containing 6 to 24 carbon atoms, such as anilino and N-methylanilino groups. The heterocyclic amino group includes 5- or 6-membered, saturated or unsaturated heterocyclic amino groups which contain in their individual rings 1 to 5 carbon atoms and at least one oxygen, nitrogen or sulfur atom. Therein, the ring-constituting hetero atom(s) may be one or more in number, and they may be the same or different in kind. Specific examples of such a heterocyclic amino group include 2-oxazolylamino, 2-tetrahydropyranylamino and 4-pyridylamino groups. The ureido group includes those containing 1 to 16 carbon atoms, preferably 1 to 10 carbon atoms, such as ureido, methylureido, N,N-diethylureido and 2-methanesulfonylamidoethylureido groups.

The sulfamoylamino group includes those containing 0 to 16 carbon atoms, preferably 0 to 10 carbon atoms, such as methylsulfamoylamino and 2-methoxyethylsulfamoylamino groups. The alkoxycarbonylamino group includes those containing 2 to 16 carbon atoms, preferably 2 to 10 carbon atoms, such as a methoxycarbonylamino group. The aryloxycarbonylamino group includes those containing 7 to 24 carbon atoms, such as phenoxycarbonylamino and 2,6-dimethoxyphenoxycarbonylamino groups. The sulfonamido group includes those containing 1 to 16 carbon atoms, preferably 1 to 10 carbon atoms, such as methanesulfonamido and p-toluenesulfonamido groups. The imido group includes those containing 4 to 16 carbon atoms, such as N-succinimido and N-phthalimido groups. The oxamoylamino group includes those containing, 2 to 16 carbon atoms, preferably 2 to 10 carbon atoms, such as an N-ethyloxamoylamino group. The heterocyclic group whose connective atom is a nitrogen atom on the ring includes 5- or 6-membered heterocyclic groups which contain in their individual rings one or more of a nitrogen atom and at least one carbon, oxygen or sulfur atom, such as pyrrolidino, morpholino and imidazolino groups.

The alkylthio group includes those containing 1 to 16 carbon atoms, preferably 1 to 10 carbon atoms, such as methylthio and 2-phenoxyethylthio groups. The arylthio group includes those containing 6 to 24 carbon atoms, such as phenylthio and 2-carboxyphenylthio groups. The heterocyclic thio group includes 5- or 6-membered, saturated or unsaturated heterocyclic thio groups which contain in their individual hetero rings 1 to 5 carbon atoms and at least one oxygen, nitrogen or sulfur atom. Therein, the number of ring-constituting hetero atom(s) may be one or more, and the kind thereof may be the same or different. Specific examples of such a heterocyclic thio group include 2-benzothiazolylthio and 2-pyridylthio groups.

The sulfamoyl group includes those containing 0 to 16 carbon atoms, preferably 0 to 10 carbon atoms, such as sulfamoyl, methylsulfamoyl and phenylsulfamoyl groups. The alkoxysulfonyl group includes those containing 1 to 16 carbon atoms, preferably 1 to 10 carbon atoms, such as a methoxysulfonyl group. The aryloxysulfonyl group includes those containing 6 to 24 carbon atoms, preferably 6 to 12 carbon atoms, such as a phenoxysulfonyl group. The sulfonyl group includes those containing 1 to 16 carbon atoms, preferably 1 to 10 carbon atoms, such as methanesulfonyl and benzenesulfonyl groups. The sulfinyl group includes those containing 1 to 16 carbon atoms, preferably 1 to 10 carbon atoms, such as methanesulfinyl and benzenesulfinyl groups. The acylsulfamoyl group includes those containing 1 to 18 carbon atoms, preferably 1 to 16 carbon atoms, such as N-acetylsulfamoyl and N-benzoyl-sulfamoyl groups.

Of those substituents which the group represented by A in formula (I) can have, a hydroxy group, a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, an ureido group, a sulfamoylamino group, an alkoxycarbonylamino group, a sulfonamido group, a sulfamoyl group and a sulfonyl group are preferred over the others. In particular, a halogen atom, an alkyl group, an aryl group, a carbamoyl group, an alkoxy group, an aryloxy group, an acylamino group, an ureido group, a sulfonamido group and a sulfamoyl group are advantageous.

The hydrazide compound of formula (I) may have as a substituent a group capable of promoting the adsorption to silver halide grains.

Examples of a group capable of promoting the adsorption to silver halide grains include the thiourea groups, the heterocyclic thioamido groups, the mercaptoheterocyclic groups and the triazolyl groups described in U.S. Pat. Nos. 4,385,108 and 4,459,347, JP-A-59-195233, JP-A-59-200231, JP-A-59-201045, JP-A-59-201046, JP-A-59-201047, JP-A-59-201048, JP-A-59-201049, JP-A-61-170733, JP-A-61-270744, JP-A-62-948, JP-A-63-234244, JP-A-63-234245, JP-A-63-234246, and so on.

Specific examples of a substituent preferred as the above-described adsorption promoting group include thioamido, thioureido, thiourethane, 5-mercaptotetrazolyl, 3-mercapto-1,2,4-triazolyl, 2-mercapto-1,3,4-thiadiazolyl, 2-mercapto-1,3,4-oxadiazolyl, alkylmercapto, arylmercapto and benzotriazolyl groups.

The aromatic groups represented by $Ar_1$, $Ar_2$ and $Ar_3$ in formula (I-B) or (II-B) include monocyclic and dicyclic arylene groups. Specific examples of such arylene groups include substituted or unsubstituted phenylene and naphthylene groups. The aromatic heterocyclic groups represented by $Ar_1$, $Ar_2$ and $Ar_3$ in formula (I-B) or (II-B) include 5- or 6-membered aromatic heterocyclic groups containing at least one N, O or S atom as hetero atom are included therein. The ring present in each of such groups may be a single ring or a condensed ring in which an aromatic hetero ring and an aromatic carbon ring or hetero ring are fused together. Specific examples of such an aromatic heterocyclic group include pyridyl, imidazolyl, quinolinyl, benzimidazolyl, pyrimidinyl, pyrazolinyl, isoquinolinyl, thiazolinyl and benzothiazolinyl groups.

In formula (I-B) or (II-B), each of $Ar_1$, $Ar_2$ and $Ar_3$ represents preferably an arylene group, especially preferably a phenylene group.

The group represented by $Ar_1$, $Ar_2$ and $Ar_3$ each may have one or more of a substituent. Such a substituent includes the same groups as included in examples of a substituent which the group represented by A in formula (I) may have.

Suitable examples of substituent(s) which the group represented by $Ar_1$, $Ar_2$ and $Ar_3$ each can have include a carboxyl group, a sulfo group, an alkyl group, an amino group, an alkylamino group, a hydroxy group, an alkoxy group, a halogen atom, an acylamino group, a sulfonamido group and an ureido group. The total number of carbon atoms contained in the substituent(s) is from 1 to 12, preferably from 1 to 8.

$Ar_3$ in formula (II-B) may have as substituents two or more of groups represented by —$L_2$—$Ar_2$—NHNH—$G_2$—$R_2$ (wherein $L_2$, $Ar_2$, $G_2$ and $R_2$ have the same meaning as in formula (II-B) respectively).

However, an unsubstituted phenylene group is preferred in particular as $Ar_1$, $Ar_2$ and $Ar_3$ each in formula (I-B) or (II-B).

The linkage group represented by $L_1$ in formula (I-B) and $L_2$ in formula (II-B) each is —O—, —S—, —N($R_N$)— (wherein $R_N$ represents a hydrogen atom, an alkyl group or an aryl group), —CO—, —C(=S)—, —$SO_2$—, —SO—, —P(=O)—, an alkylene group, or a group formed by combining two or more thereof. Herein, however, the group formed by combination does not include the case in which $L_1$ linked to a heterocyclic group represented by A in formula (I) takes the form of a carbamoyl group.

The linkage group represented by $L_3$ in formula (II-B) is —O—, —S—, —N($R_N$)— (wherein $R_N$ represents a hydrogen atom, an alkyl group or an aryl group), —CO—, —C(=S)—, —$SO_2$—, —SO—, —P(=O)—, an alkylene group, an arylene group, and a group formed by combining two or more thereof.

Specific examples of a group formed by the combination include —CON($R_N$)—, —$SO_2$N($R_N$)—, —COO—, —N($R_N$)CON($R_N$)—, —N($R_N$)CSN($R_N$)—, —N($R_N$)$SO_2$N($R_N$)—, —$SO_2$N($R_N$)CO—, $SO_2$N($R_N$)CON($R_N$)—, —N($R_N$)COCON($R_N$)—, —CON($R_N$)CO—, —S-alkylene-CONH—, —O-alkylene-CONH—, —O-alkylene-NHCO—, —N($R_N$)N($R_N$)CONH—, —(—O—)$_2$P(=O)O—, and —NHCO-arylene-$SO_2$NH—. Additionally, these groups each may be attached to A in formula (I) at the left or right linking site.

When each of the linkage groups, $L_1$ in formula (I-B) and $L_2$ and $L_3$ in formula (II-B), contains a trivalent group or above, two or more of —$Ar_1$—NHNH—$G_1$—$R_1$ groups may be attached to $L_1$ in formula (I-B), two or more of —$Ar_2$—NHNH—$G_2$—$R_2$ groups may be attached to $L_2$ in formula (II-B), and two or more of —$Ar_3$—$L_2$—$Ar_2$NHNH—$G_2$—$R_2$ groups may be attached to $L_3$ in formula (II-B).

The term "a trivalent group or above" as used therein specifically signifies an amino or alkylene group in the cases of $L_1$ and $L_2$, and an amino, alkylene or arylene group in the case of $L_3$.

The hydrazide compound represented by formula (I) does not contain diphenyl sulfide and 1,4-bis(phenylthio)benzene structures as a partial structure.

Furthermore, the hydrazide compound represented by formula (I) contains neither quaternarized nitrogen atom, such as an ammonio group, nor heterocyclic group containing a quaternarized nitrogen, such as a pyridinio group, in moieties other than $R_1$ in formula (I-B) and $R_2$ in formula (II-B).

Each of $L_1$ in formula (I-B) and $L_2$ in formula (II-B) is preferably —$SO_2$NH—, —NHCONH—, —O—, —S— or —N($R_N$)—, and particularly preferably —$SO_2$NH—.

$L_3$ in formula (II-B) is preferably —CONH—, —$SO_2$NH—, —NHCONH— or —COO—.

$G_1$ in formula (I-B) and $G_2$ in formula (II-B) each represent a carbonyl group, an oxalyl group, a sulfonyl group or a phosphoryl group, preferably a carbonyl group or an oxalyl group, and more preferably a carbonyl group.

$R_1$ in formula (I-B) and $R_2$ in formula (II-B) each represent a hydrogen atom or a blocking group. Specifically, such a blocking group includes an alkyl group, an aralkyl group, an alkenyl group, alkynyl group, an aryl group, a heterocyclic group, an alkoxy group, an aryloxy group, an amino group and a hydrazino group. These groups other than a hydrogen atom each may be substituted.

Examples of the alkyl group include methyl, trifluoromethyl, difluoromethyl, 2-carboxytetrafluoroethyl, methoxyethyl, phenoxymethyl, pyridiniomethyl, 3-hydroxypropyl, 3-methanesulfonamidopropyl and phenylsulfonylmethyl groups. Examples of the aralkyl group include o-hydroxybenzyl and o-aminobenzyl groups. Examples of the alkenyl group include vinyl and 2-ethoxycarbonylvinyl groups. Examples of the alkynyl group include ethynyl and 2-methoxycarbonylethynyl groups. Examples of the aryl group include 3,5-dichlorophenyl, 2-hydroxymethylphenyl, 2-carbamoylphenyl, 3,5-dichloro-2-hydroxymethylphenyl, 2-methanesulfonamidophenyl, 4-cyanophenyl and 3,4-dinitrophenyl groups. Examples of the heterocyclic group include 4-pyridyl, benzotriazole-5-yl, 3-(2-mercaptotetrazolyl)phenyl and N-methyl-4-pyridinio groups. Examples of the alkoxy group include methoxy, propoxy and 2-hydroxyethoxy groups. Examples of the aryloxy group include phenoxy and 1-naphthyloxy groups. Examples of the amino group include amino, propylamino, dimethylamino, 2,2,6,6-tetramethylpiperidine-4-yl, anilino, 2-hydroxyanilino, 5-benzotriazolylamino and 1-benzyl-3-pyridinioamino groups. Examples of the hydrazino group include hydrazino, 2-phenylhydrazino and 4-benzenesulfonamidophenylhydrazino groups.

When such a blocking group as recited above have at least one substituent, the substituent include the same ones as given as examples of substituent(s) which A in formula (I) can have. The number of total carbons in the substituents is preferably from 0 to 12, more preferably from 0 to 8.

When $G_1$ in formula (I-B) or $G_2$ in formula (II-B) represents a carbonyl group, $R_1$ or $R_2$ respectively represents preferably a hydrogen atom, an alkyl group, an alkenyl group, an alkynyl group, an aryl group or a heterocyclic group, more preferably a hydrogen atom, an alkyl group or an aryl group, most preferably an alkyl group.

When $G_1$ in formula (I-B) or $G_2$ in formula (II-B) represents an oxalyl group, $R_1$ or $R_2$ respectively represents preferably an alkoxy group, an aryloxy group or an amino group, more preferably an amino group.

Symbol b in formula (I) represents an integer of from 2 to 6, preferably 2, 3 or 4, particularly preferably 2 or 3. As b is an integer of from 2 to 6, a plurality of B are present in formula (I), and they may be the same as or different from one another.

Of the groups represented by formulae (I-B) and (II-B), those represented by formulae (III-B) and (IV-B) respectively are preferred:

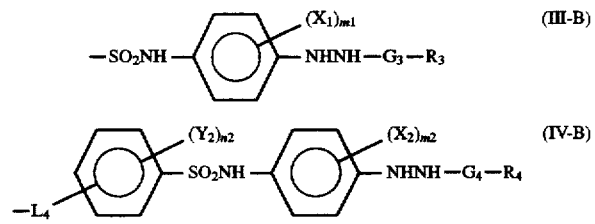

wherein $G_3$, $G_4$, $R_3$, $R_4$ and $L_4$ have the same meanings as $G_1$, $G_2$, $R_1$, $R_2$ and $L_3$ respectively in formulae (I-B) and (II-B); $X_1$, $X_2$ and $Y_2$ each represent a substituent; and $m_1$, $m_2$ and $n_2$ each represent an integer of from 0 to 4.

The substituents represented by $X_1$, $X_2$ and $Y_2$ in formulae (III-B) and (IV-B) include the same as the substituents which the aromatic groups represented by $Ar_1$, $Ar_2$ and $Ar_3$ in formulae (I-B) and (II-B) can have, and the preferred range of those substituents is also the same as that of the substituents on the aromatic groups. $m_1$, $m_2$ and $n_2$ each represent an integer of from 0 to 4, preferably 0 or 1, particularly preferably 0.

Of the compounds represented by formula (I), the compounds represented by the following formulae (V) or (VI) are preferred over the others:

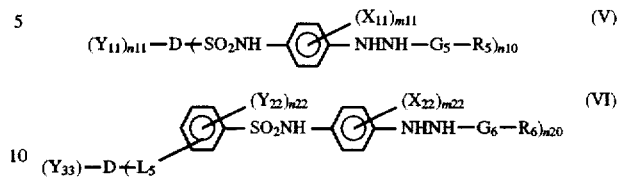

In the above formulae, $X_{11}$, $X_{22}$, $Y_{22}$, $m_{11}$, $m_{22}$ and $n_{22}$ have the same meanings as $X_1$, $X_2$, $Y_2$, $m_1$, $m_2$ and $n_2$ respectively in formulae (III-B) and (IV-B), and $L_5$ has the same meaning as $L_4$ in formula (IV-B). The preferred ranges of those symbols are the same as those of their corresponding ones. $G_5$ and $G_6$ each represent a carbonyl group or an oxalyl group. $R_5$ and $R_6$ each represent a hydrogen atom, a substituted alkyl group or a substituted phenyl group when $G_5$ and $G_6$ are each a carbonyl group; while when $G_5$ and $G_6$ are each an oxalyl group, $R_5$ and $R_6$ each represents an amino group.

$G_5$ in formula (V) and $G_6$ in formula (VI) each is preferably a carbonyl group. R5 and R6 each is preferably an alkyl group substituted with at least one fluorine atom, more preferably a trifluoromethyl group, a difluoromethyl group or a 2-carboxytetrafluoroethyl group, most preferably a trifluoromethyl or a difluoromethyl group.

$Y_{33}$ and $Y_{11}$ each represent a substituent. Examples of the substituent include the substituents which A in formula (I) can have. They each have the same preferred range as the substituents on A.

$n_{11}$ and $n_{33}$ each represent an integer of from 0 to 6, preferably from 0 to 4, particularly preferably 0, 1 or 2. When $n_{11}$ and $n_{33}$ each represents 2 or above, $Y_{33}$ groups may be the same or different, and $Y_{11}$ groups also may be the same or different.

D in the formulae (V) and (VI) is a 5- or 6-membered, saturated or unsaturated heterocyclic group which contains at least one N, O or S atom as a hetero atom and may further be fused together with another ring, or a group represented by the following formula (VII), (VIII) or (IX):

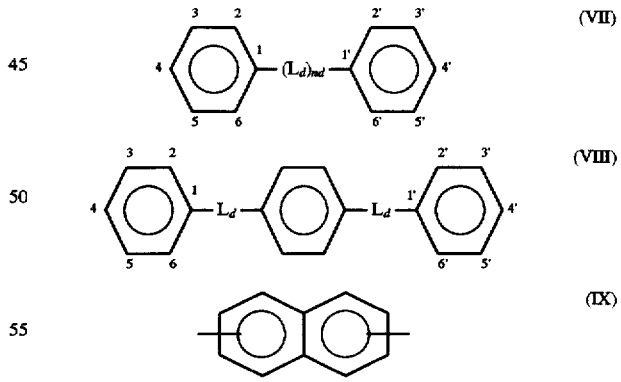

In the above formulae, $L_d$ represents a divalent organic group, and $n_d$ represents 0 or 1. Specifically, $L_d$ represents —O—, —N($R_{Nd}$)—, —SO$_2$—, —C($R_{C1}$)($R_{C2}$)— or —CO—, wherein $R_{Nd}$ represents a hydrogen atom, an alkyl group, an aryl group, an acyl group, a sulfonyl group or an oxycarbonyl group, and $R_{C1}$ and $R_{C2}$ each represent a hydrogen atom, an alkyl group or an aryl group. When each of $R_{Nd}$, $R_{C1}$ and $R_{C2}$ represents an alkyl group, the alkyl group is preferably a substituted or unsubstituted alkyl group containing 1 to 8 carbon atoms in total. When each of them represents an aryl group, the aryl group is preferably a substituted or unsubstituted aryl group containing 6 to 12 carbon atoms in total, especially preferably a-substituted or unsubstituted phenyl group.

The group represented by formula (VII) or (VIII) can combine with the substituent of D in formula (V) or (VI), namely $Y_{11}$ or $Y_{33}$, or the groups represented by the following respective formulae at an arbitrary position. However, the group is preferably substituted at such a position as not to impair the symmetry of the molecule. Therefore, the position suitable for the substitution is the 2,2'-, 3,3'-, 4,4'-, 5,5'- or 6,6'-position in the formula (VII) or (VIII), or the combined position thereof.

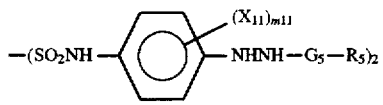

-continued or

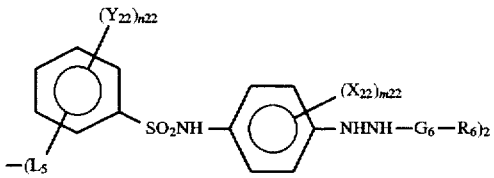

$n_{10}$ and $n_{20}$ are each 2 or 3, with the proviso that $n_{10}$ and $n_{20}$ are each 2 when D is represented by formula (VII) or (VIII).

Specific examples of the present compound are illustrated below. However, the invention should not be construed as being limited to these examples.

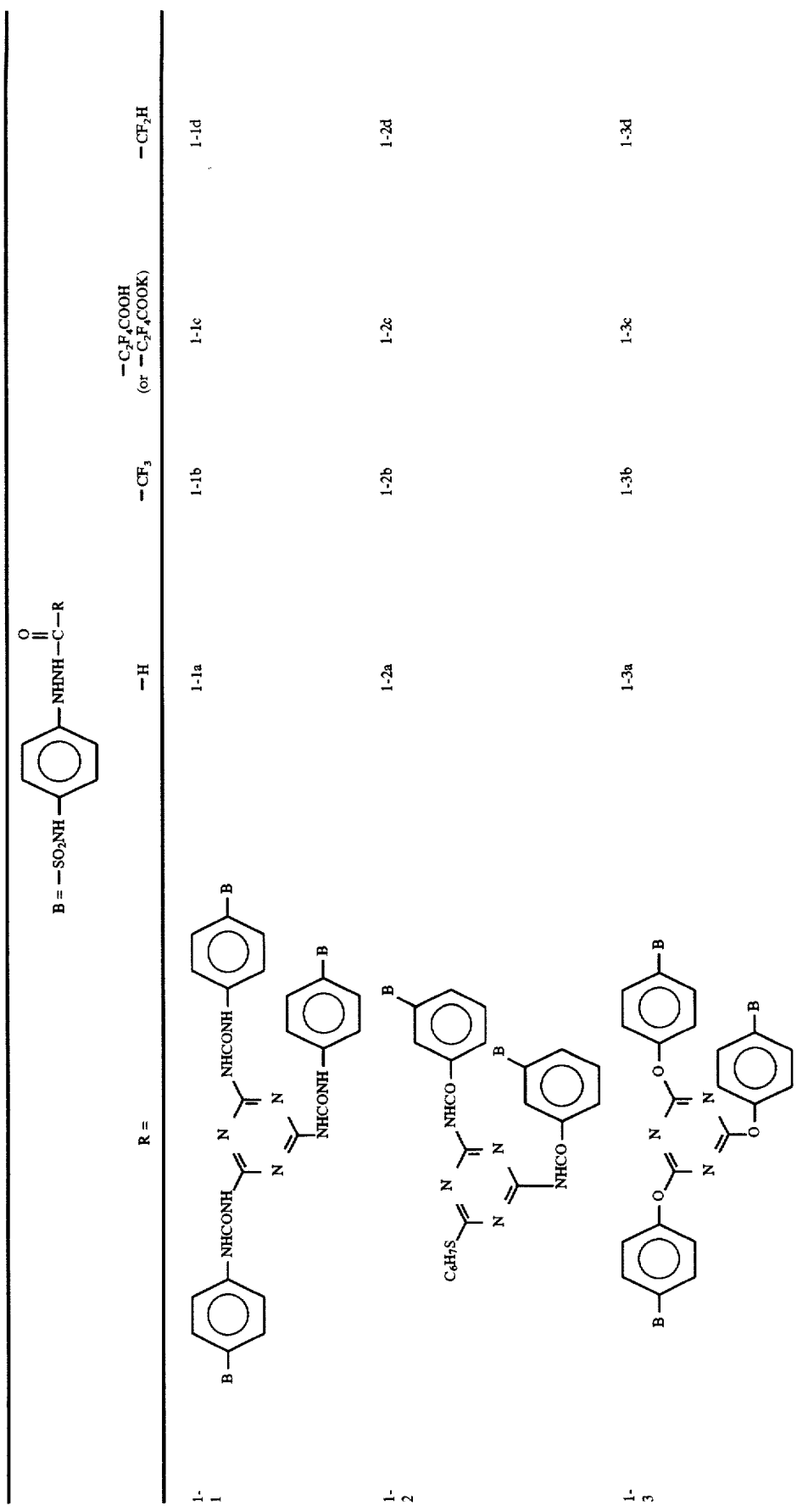

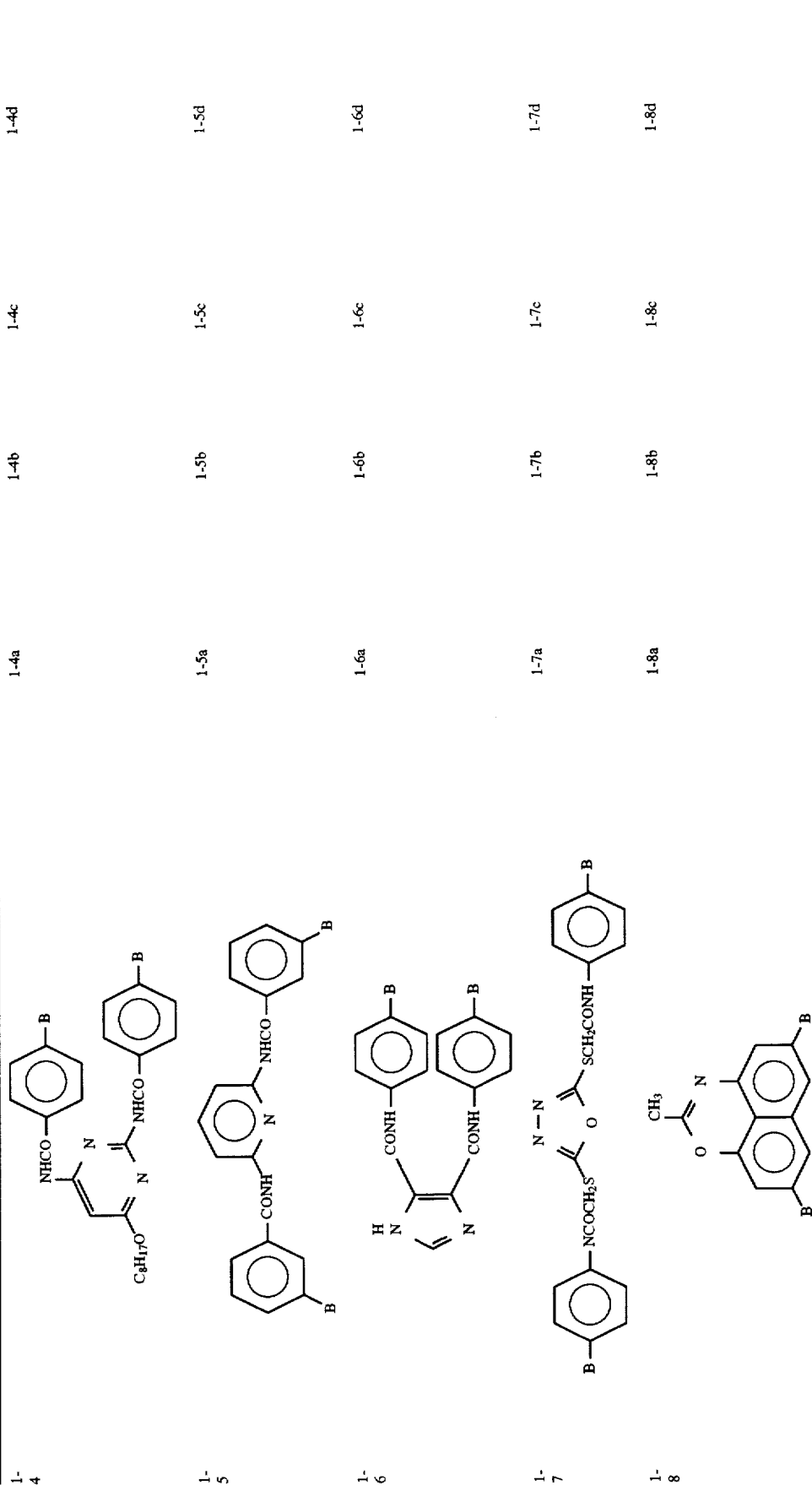

-continued
| | | | | | |
|---|---|---|---|---|---|
| 1-9 | 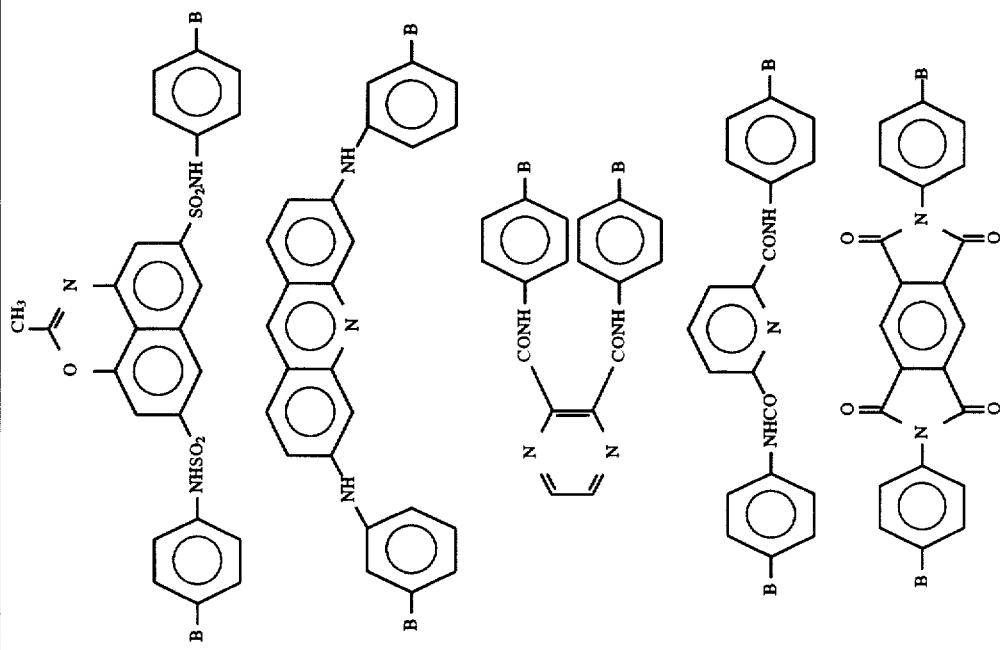 | 1-9a | 1-9b | 1-9c | 1-9d |
| 1-10 | | 1-10a | 1-10b | 1-10c | 1-10d |
| 1-11 | | 1-11a | 1-11b | 1-11c | 1-11d |
| 1-12 | | 1-12a | 1-12b | 1-12c | 1-12d |
| 1-13 | | 1-13a | 1-13b | 1-13c | 1-13d |

-continued

| | | | | |
|---|---|---|---|---|
| 1-14 | (structure) | 1-14a | 1-14b | 1-14c | 1-14d |
| 1-15 | (structure) | 1-15a | 1-15b | 1-15c | 1-15d |
| 1-16 | (structure) | 1-16a | 1-16b | 1-16c | 1-16d |
| 1-17 | (structure) | 1-17a | 1-17b | 1-17c | 1-17d |
| 1-18 | (structure) | 1-18a | 1-18b | 1-18c | 1-18d |
| 1-19 | (structure) | 1-19a | 1-19b | 1-19c | 1-19d |
| 1-20 | (structure) | 1-20a | 1-20b | 1-20c | 1-20d |

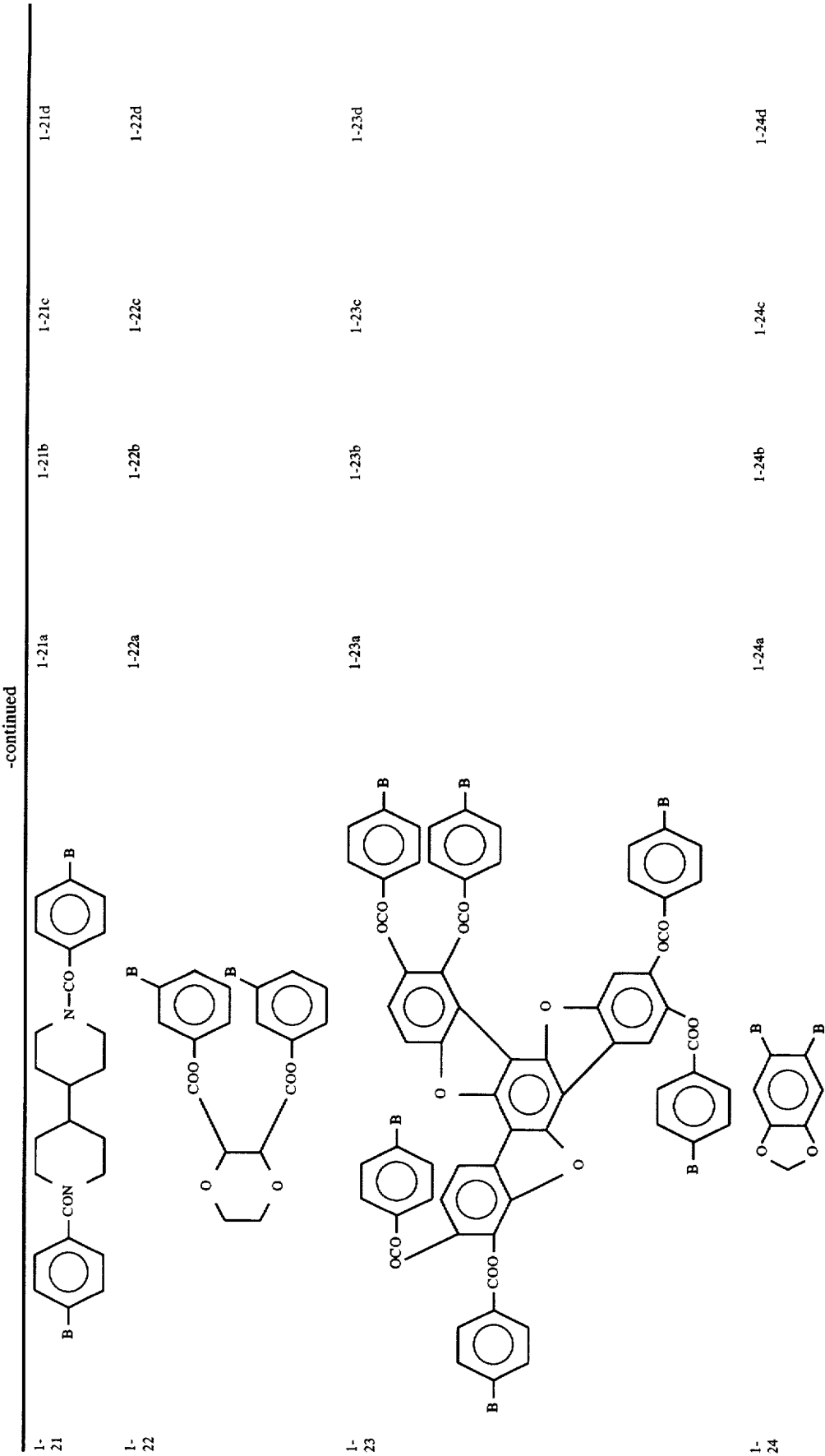

| | | | | | |
|---|---|---|---|---|---|
| 1-25 | structure with two SO₂NH groups linked to benzodioxole, each connected to phenyl-B | 1-25a | 1-25b | 1-25c | 1-25d |
| 1-26 | benzodioxole with two B substituents | 1-26a | 1-26b | 1-26c | 1-26d |
| 1-27 | 2-methylbenzoxazole with two B substituents | 1-27a | 1-27b | 1-27c | 1-27d |
| 1-28 | benzodioxole with two NHCO-phenyl-B groups | 1-28a | 1-28b | 1-28c | 1-28d |
| 1-29 | benzodioxole with two CONH-phenyl-B groups | 1-29a | 1-29b | 1-29c | 1-29d |
| 1-30 | naphthalenediimide with two N-phenyl-B groups | 1-30a | 1-30b | 1-30c | 1-30d |

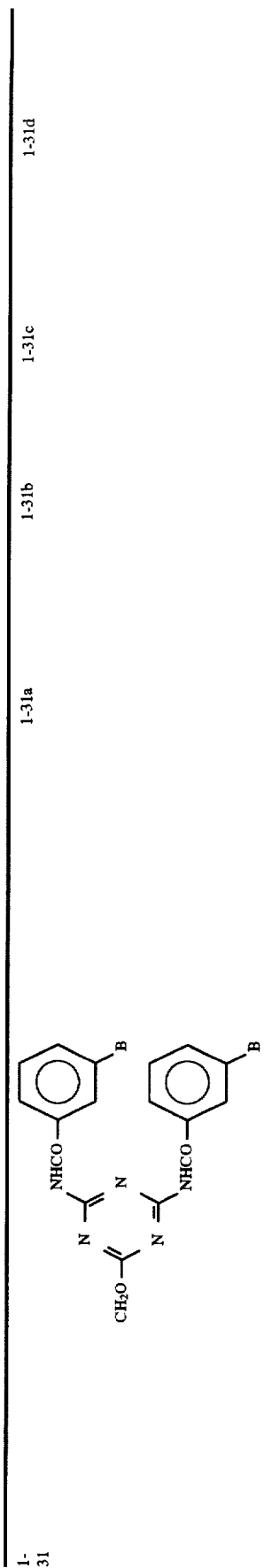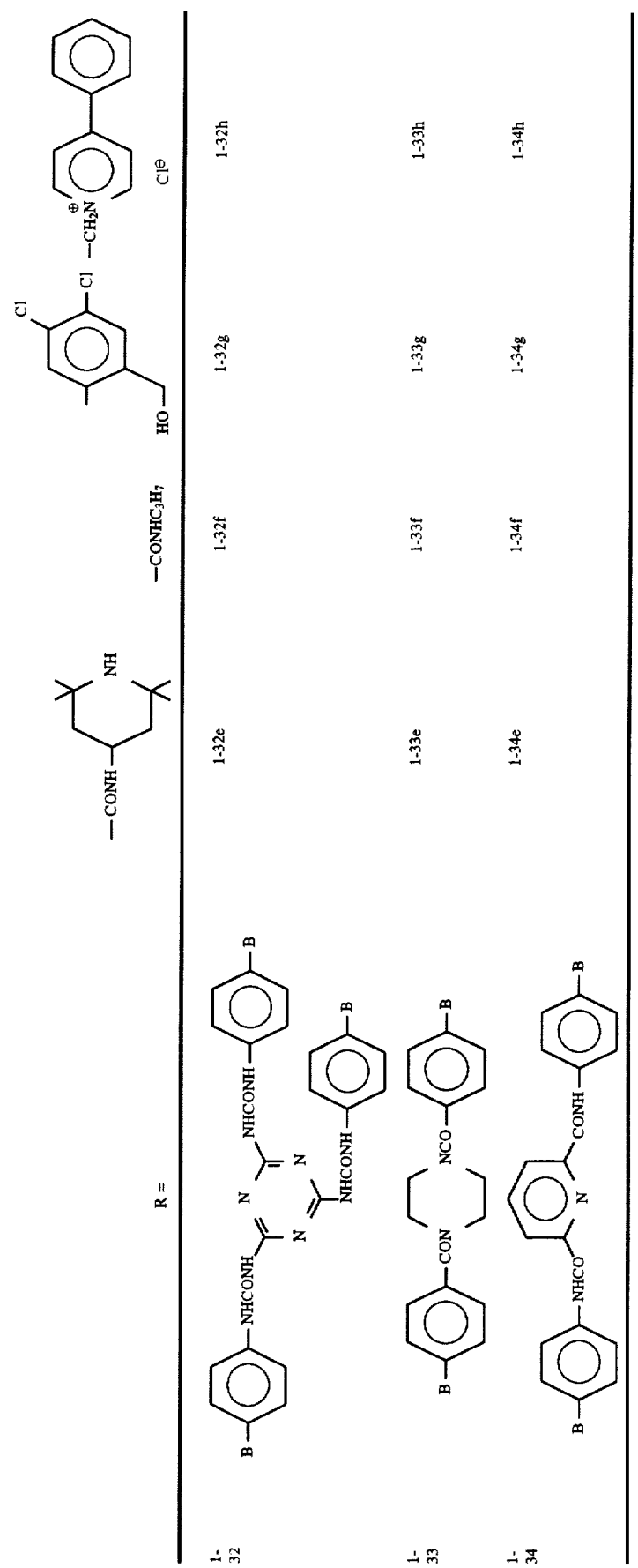

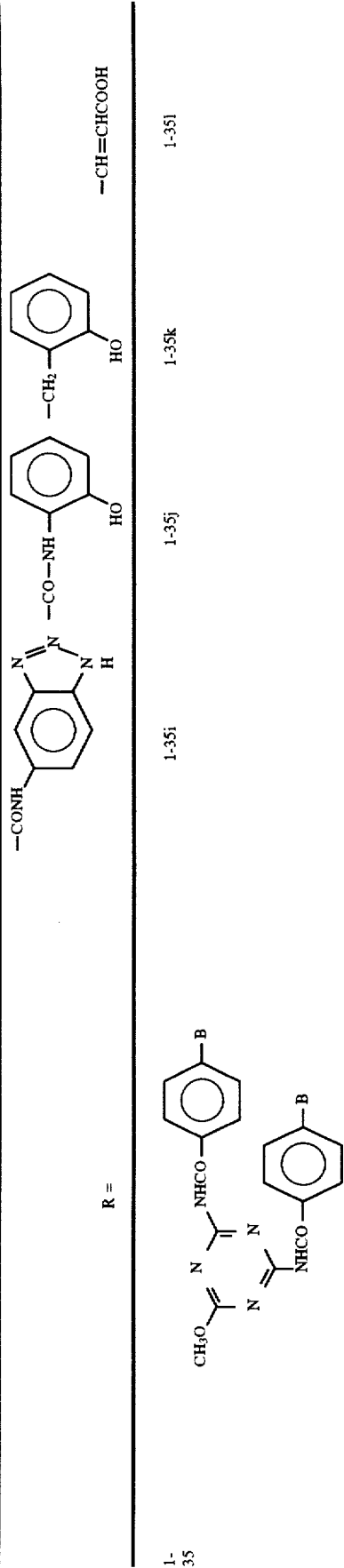
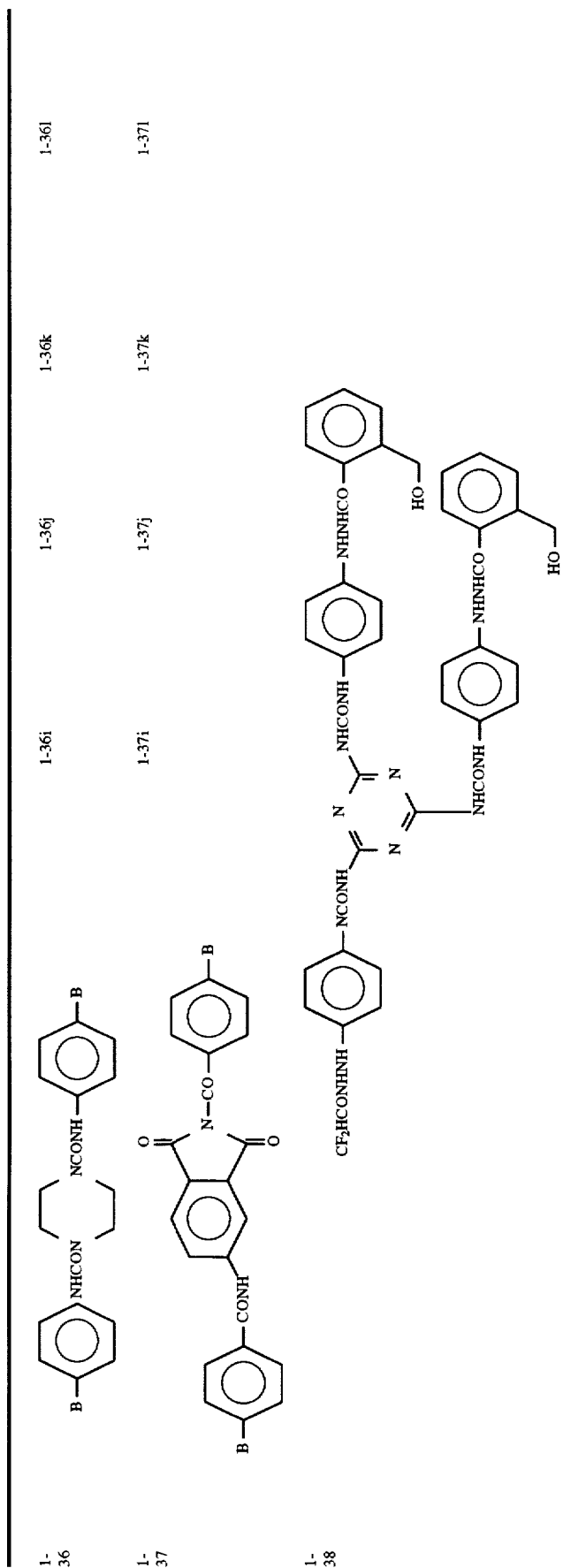

-continued
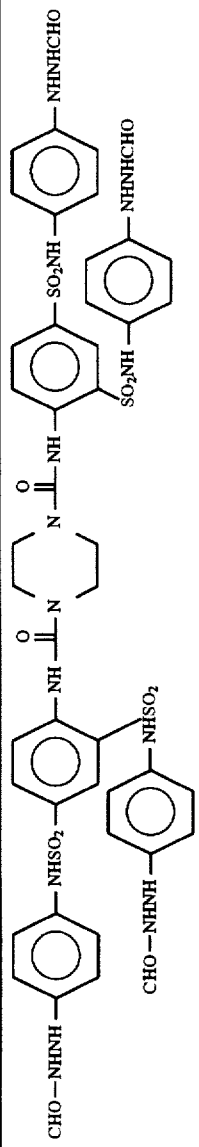
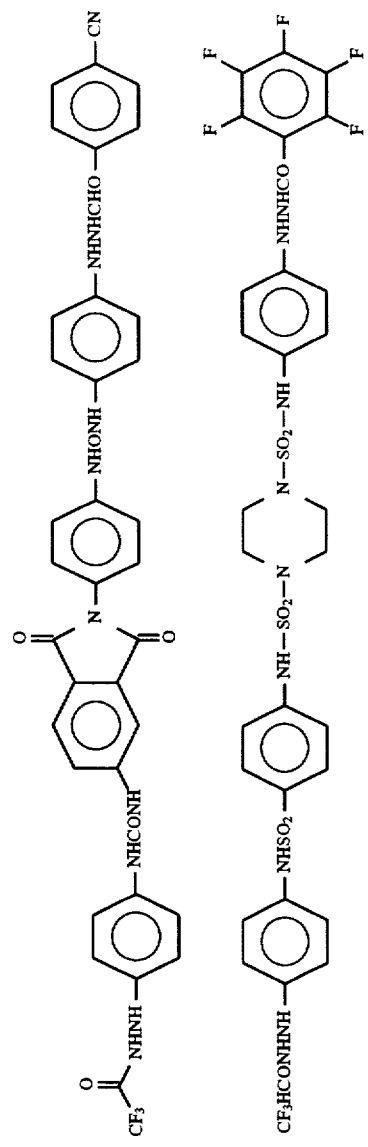

$B = -SO_2NH-\phantom{x}\underset{\phantom{x}}{\text{C}_6\text{H}_4}-NHNH-\overset{O}{\underset{\|}{C}}-R$

| | R = | −H | −CF₃ | −CF₂H | −CF₂CF₂COOH |
|---|---|---|---|---|---|
| 2-1 | naphthalene-1,5-diyl with B at both positions | 2-1a | 2-1b | 2-1c | 2-1d |
| 2-2 | naphthalene-2,6-diyl with B at both positions | 2-2a | 2-2b | 2-2c | 2-2d |
| 2-3 | naphthalene-1,6-diyl with B at both positions | 2-3a | 2-3b | 2-3c | 2-3d |
| 2-4 | naphthalene-1,5-diyl with -SO₂NH-C₆H₄-B at both positions | 2-4a | 2-4b | 2-4c | 2-4d |
| 2-5 | naphthalene-2,6-diyl with -SO₂NH-C₆H₄-B and -NHSO₂-C₆H₄-B | 2-5a | 2-5b | 2-5c | 2-5d |

-continued

| | | | | |
|---|---|---|---|---|
| 2-6 | ![structure with NHCO-C6H4-B groups on naphthalene] | 2-6a | 2-6b | 2-6c | 2-6d |
| 2-7 | ![structure with NHCO-C6H4-B groups on naphthalene] | 2-7a | 2-7b | 2-7c | 2-7d |
| 2-8 | ![structure with NHSO2-C6H4-B groups on naphthalene] | 2-8a | 2-8b | 2-8c | 2-8d |
| 2-9 | ![structure with OCO-C6H4-B groups on naphthalene] | 2-9a | 2-9b | 2-9c | 2-9d |

-continued

| | | 2-10a | 2-10b | 2-10c | 2-10d |
|---|---|---|---|---|---|
| 2-10 | (naphthalene with two OCO-C6H4-B groups) | | | | |
| 2-11 | (naphthalene with two NHCO-C6H4-B groups) | 2-11a | 2-11b | 2-11c | 2-11d |
| 2-12 | (naphthalene with two NHCONH-C6H4-B groups) | 2-12a | 2-12b | 2-12c | 2-12d |
| 2-13 | (naphthalene with two CONH-C6H4-B groups) | 2-13a | 2-13b | 2-13c | 2-13d |

-continued

| | | | | | |
|---|---|---|---|---|---|
| 2-14 | (structure) | 2-14a | 2-14b | 2-14c | 2-14d |
| 2-15 | (structure) | 2-15a | 2-15b | 2-15c | 2-15d |
| 2-16 | (structure) | 2-16a | 2-16b | 2-16c | 2-16d |
| 2-17 | (structure) | 2-17a | 2-17b | 2-17c | 2-17d |
| 2-18 | (structure) | 2-18a | 2-18b | 2-18c | 2-18d |
| 2-19 | (structure) | 2-19a | 2-19b | 2-19c | 2-19d |

-continued
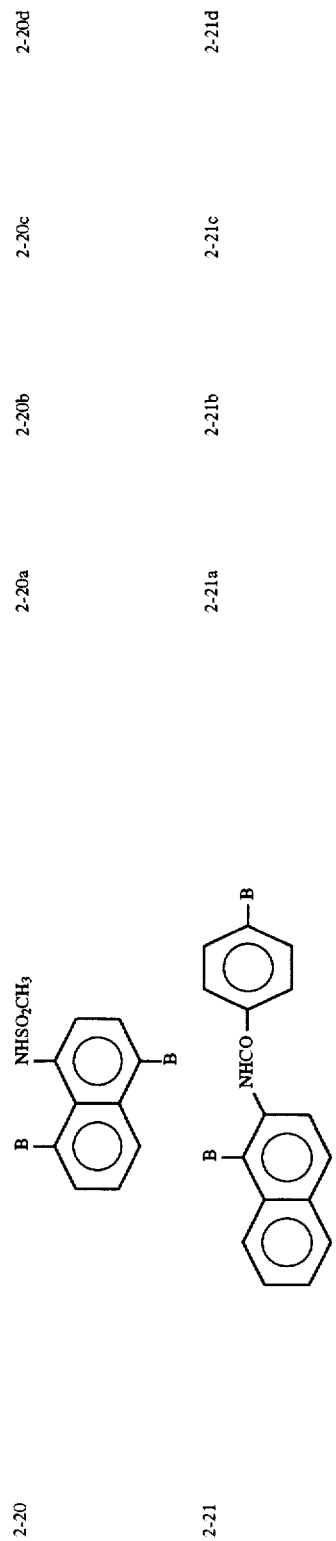
| | | | | | |
|---|---|---|---|---|---|
| 2-20 | | 2-20a | 2-20b | 2-20c | 2-20d |
| 2-21 | | 2-21a | 2-21b | 2-21c | 2-21d |
| 2-22 | | 2-22a | 2-22b | 2-22c | 2-22d |
| 2-23 | | 2-23a | 2-23b | 2-23c | 2-23d |
| 2-24 | | 2-24a | 2-24b | 2-24c | 2-24d |
| 2-25 | | 2-25a | 2-25b | 2-25c | 2-25d |

-continued
| | | | | | |
|---|---|---|---|---|---|
| 2-26 | 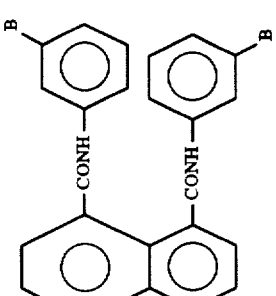 | 2-26a | 2-26b | 2-26c | 2-26d |
| 2-27 | 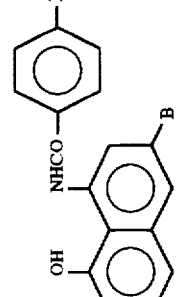 | 2-27a | 2-27b | 2-27c | 2-27d |
| 2-28 | 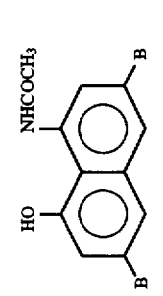 | 2-28a | 2-28b | 2-28c | 2-28d |
| 2-29 | 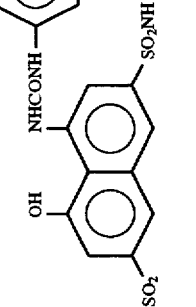 | 2-29a | 2-29b | 2-29c | 2-29d |
| 2-30 | 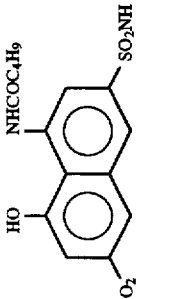 | 2-30a | 2-30b | 2-30c | 2-30d |

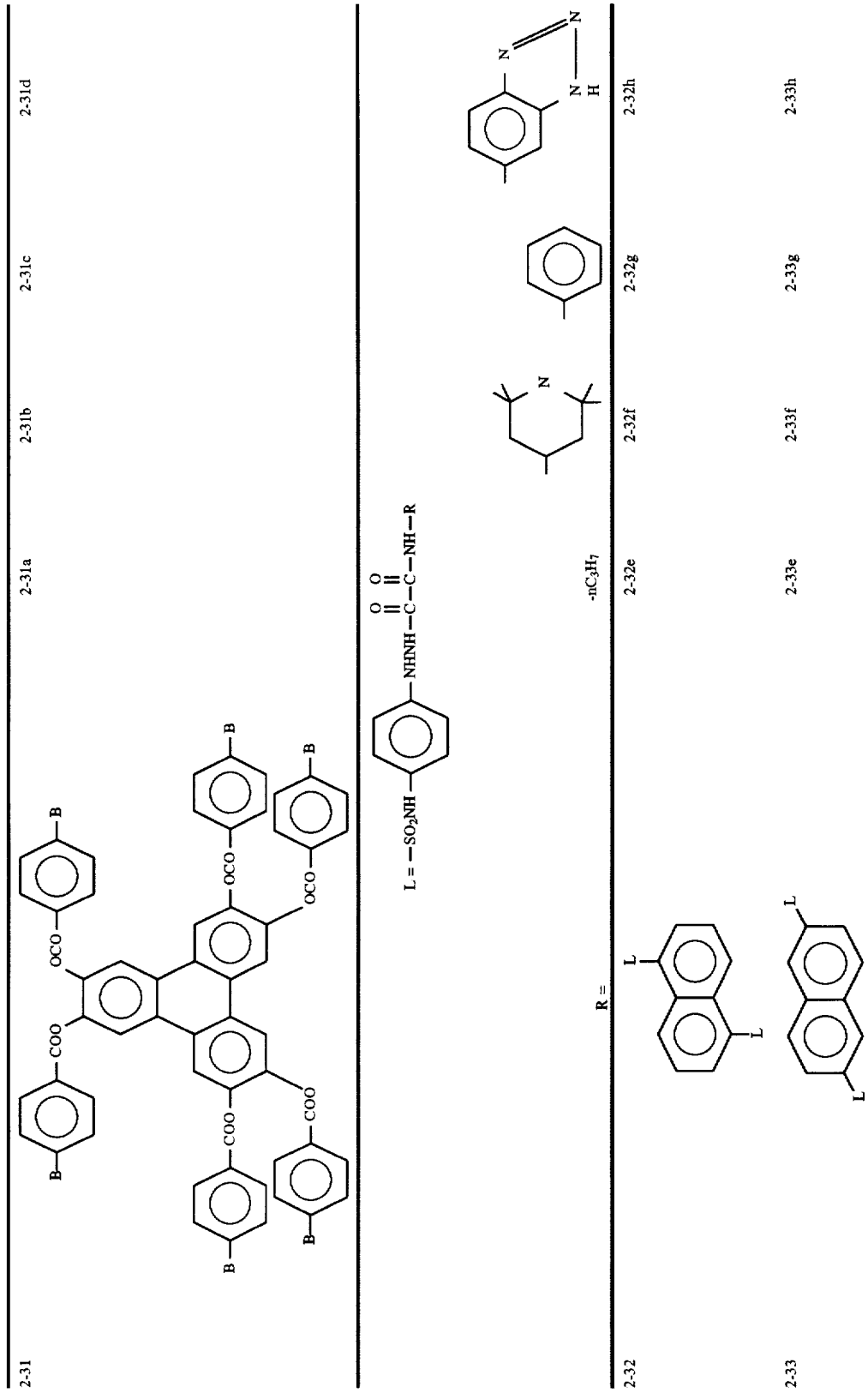

-continued

| | | | | | | |
|---|---|---|---|---|---|---|
| 2-34 | (structure: naphthalene with two SO₂NH-C₆H₄-L groups) | 2-34e | 2-34f | 2-34g | 2-34h | |
| 2-35 | (structure: naphthalene with two CONH-C₆H₄-L groups) | 2-35e | 2-35f | 2-35g | 2-35h | |
| 2-36 | (structure: naphthalene with OH and two L substituents) | 2-36e | 2-36f | 2-36g | 2-36h | |
| 2-37 | (structure: naphthalene-NHCO-C₆H₄-L with L) | 2-37e | 2-37f | 2-37g | 2-37h | |
| 2-38 | (structure: naphthalene with NHCOC₄H₉, SO₂NH-C₆H₄-L, and NHSO₂-C₆H₄-L) | 2-38e | 2-38f | 2-38g | 2-38h | |

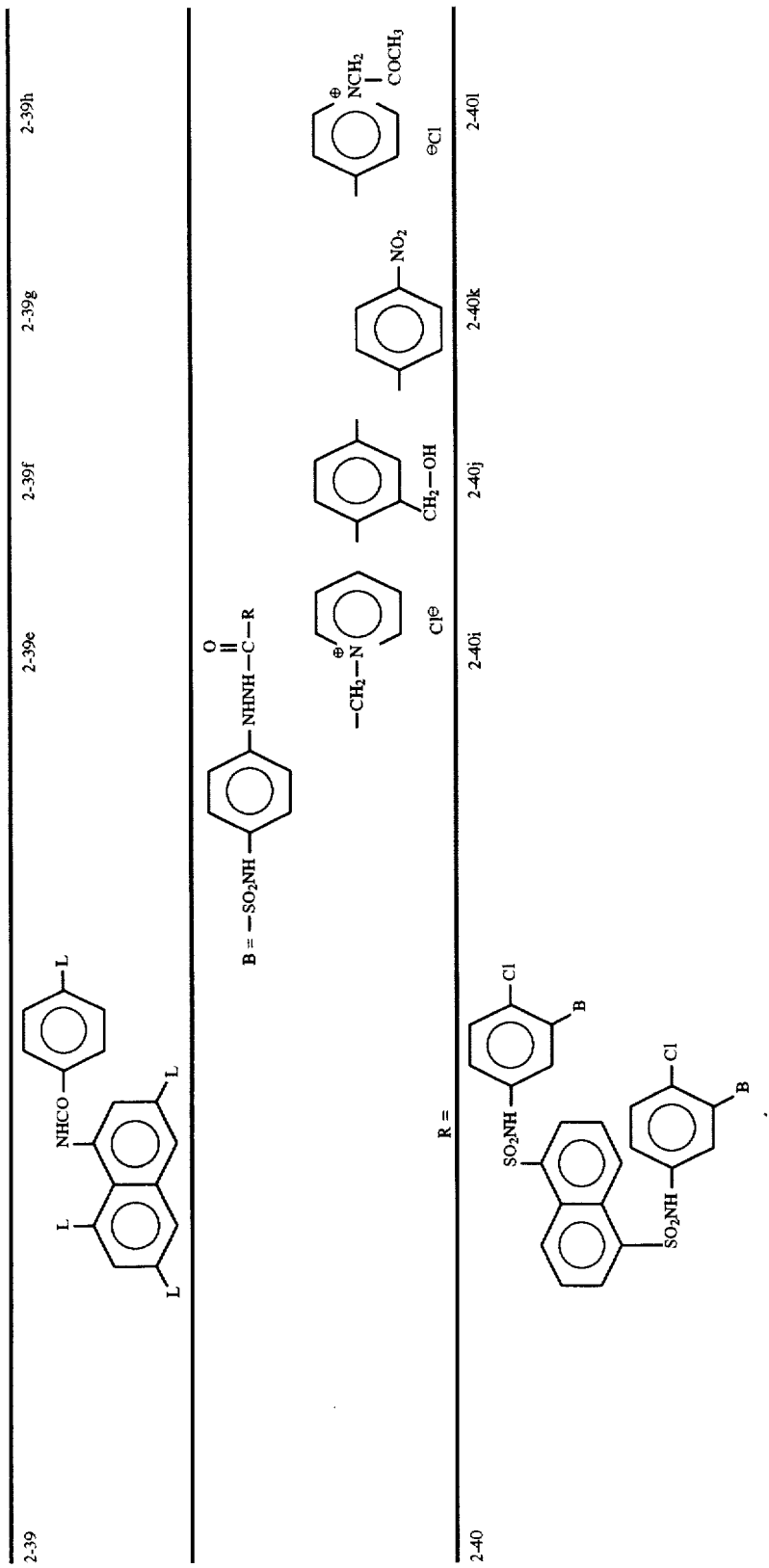

-continued
| | 2-41i | 2-41j | 2-41k | 2-41l |
|---|---|---|---|---|
| 2-41 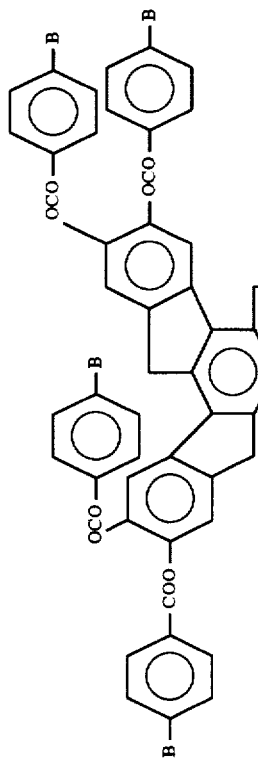 | | | | |
| 2-42 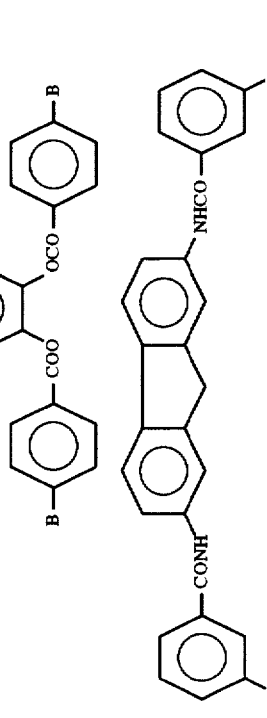 | 2-42i | 2-42j | 2-42k | 2-42l |
| 2-43 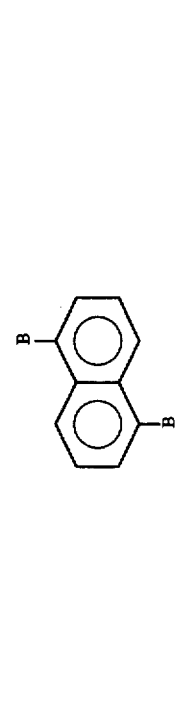 | 2-43i | 2-43j | 2-43k | 2-43l |
| 2-44 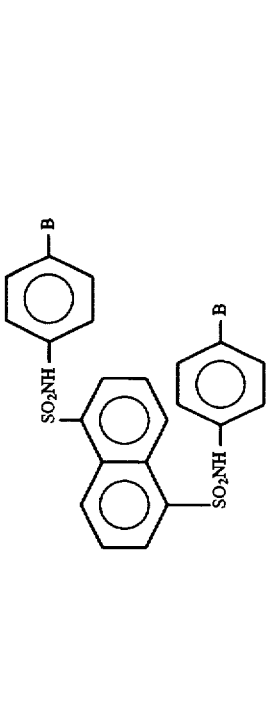 | 2-44i | 2-44j | 2-44k | 2-44l |

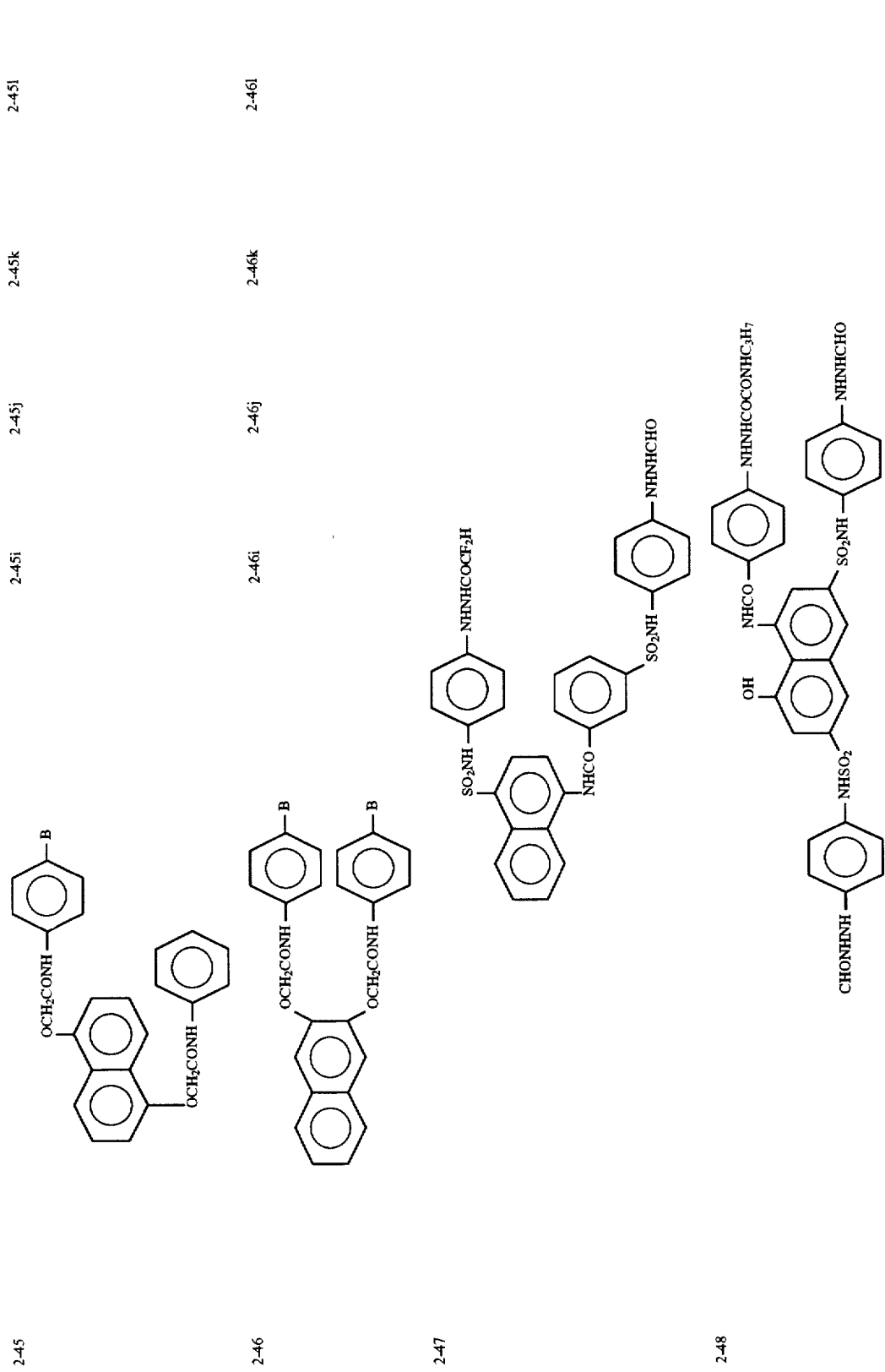

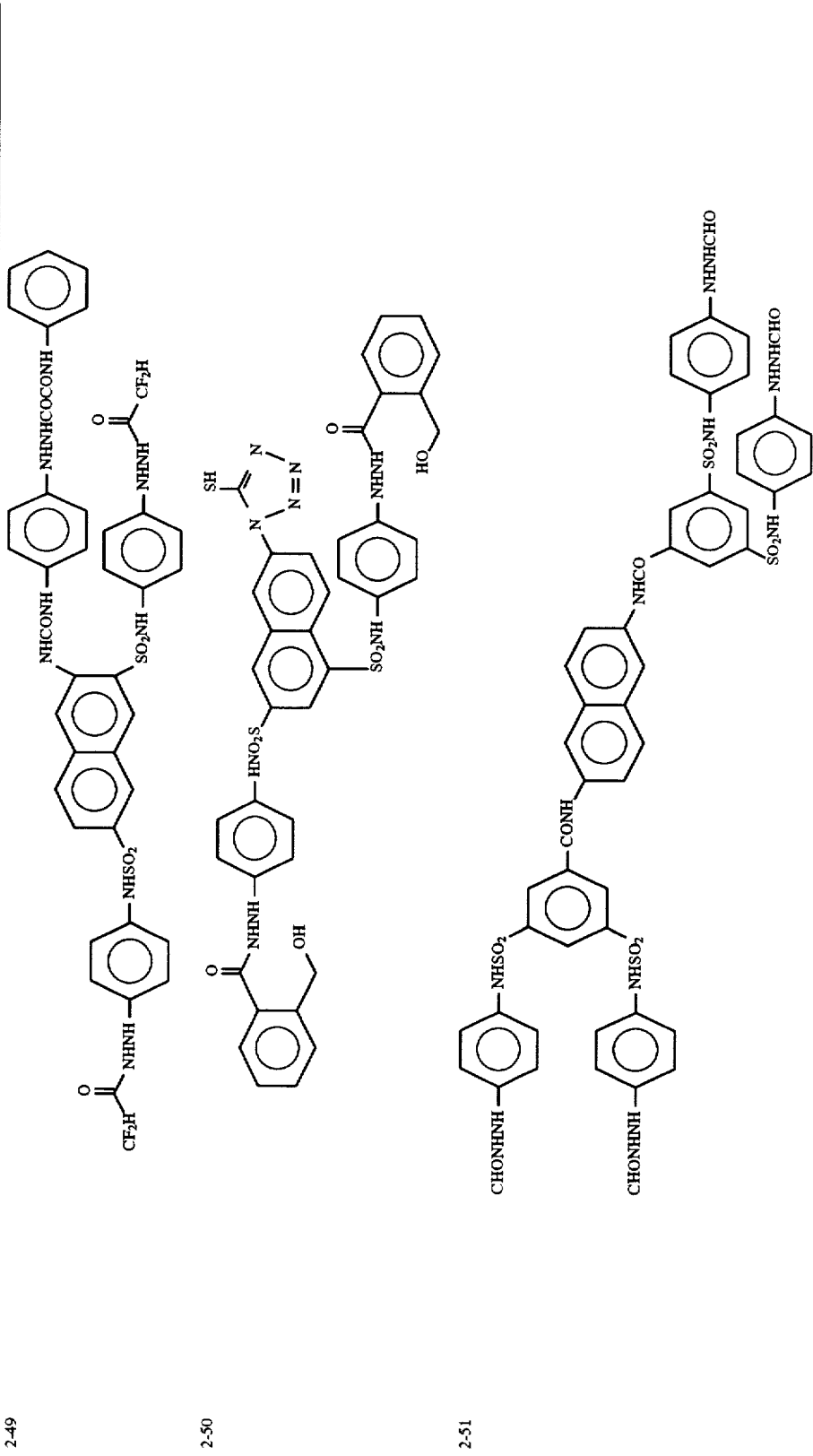

$B = -SO_2NH-\underset{\underset{O}{\|}}{\text{NHNH}-C-R}$

| R = | −H | −CF$_3$ | −CF$_2$H | −CF$_2$CF$_2$COOH |
|---|---|---|---|---|
| 3-1 | 3-1a | 3-1b | 3-1c | 3-1d |
| 3-2 | 3-2a | 3-2b | 3-2c | 3-2d |
| 3-3 | 3-3a | 3-3b | 3-3c | 3-3d |
| 3-4 | 3-4a | 3-4b | 3-4c | 3-4d |
| 3-5 | 3-5a | 3-5b | 3-5c | 3-5d |
| 3-6 | 3-6a | 3-6b | 3-6c | 3-6d |

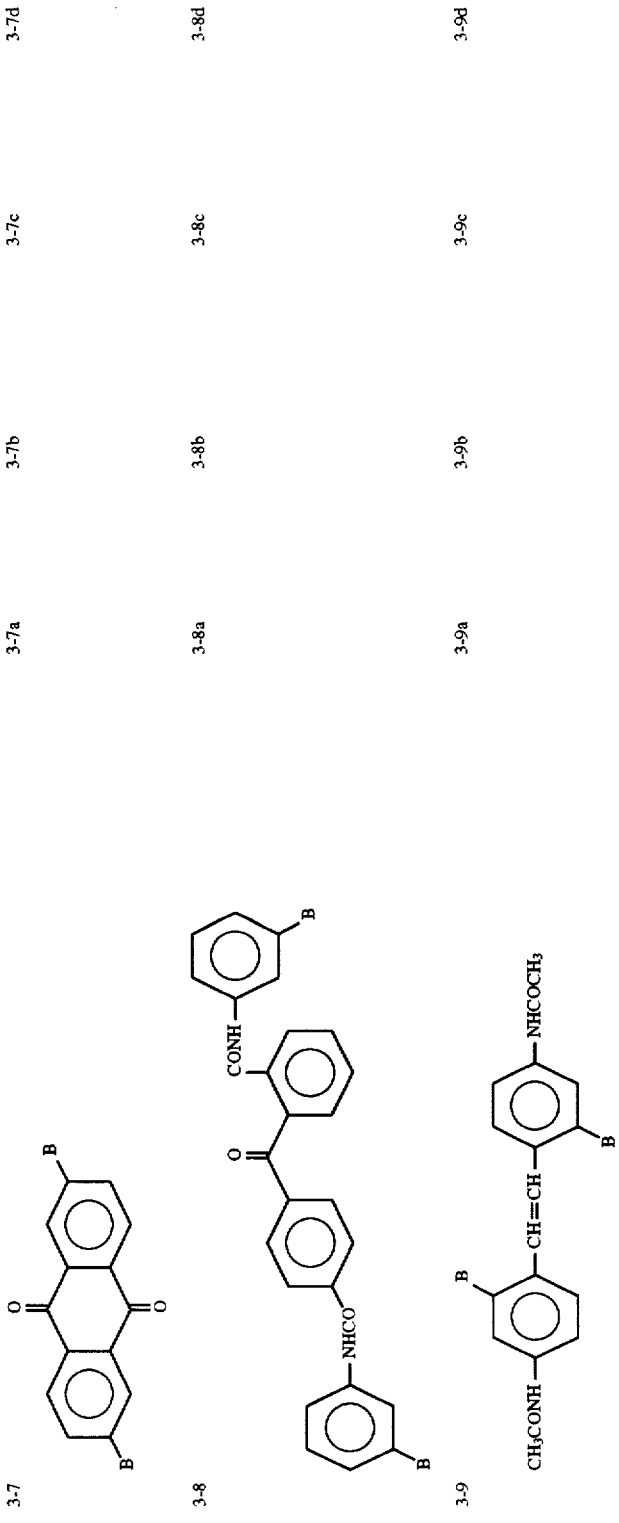

-continued

B = —SO₂NH—⟨C₆H₄⟩—NHNH—C(=O)—R

| | a | b | c | d |
|---|---|---|---|---|
| 3-10 | 3-10a | 3-10b | 3-10c | 3-10d |
| 3-11 | 3-11a | 3-11b | 3-11c | 3-11d |
| 3-12 | 3-12a | 3-12b | 3-12c | 3-12d |
| 3-13 | 3-13a | 3-13b | 3-13c | 3-13d |

-continued
| | B = —SO₂NH—⟨⟩—NHNH—C(=O)—R | | | |
|---|---|---|---|---|
| 3-14 | 3-14a | 3-14b | 3-14c | 3-14d |
| 3-15 | 3-15a | 3-15b | 3-15c | 3-15d |
| 3-16 | 3-16a | 3-16b | 3-16c | 3-16d |
| 3-17 | 3-17a | 3-17b | 3-17c | 3-17d |
| 3-18 | 3-18a | 3-18b | 3-18c | 3-18d |
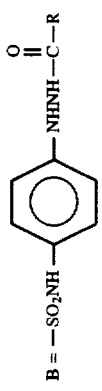
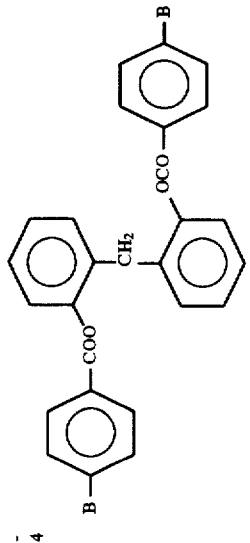
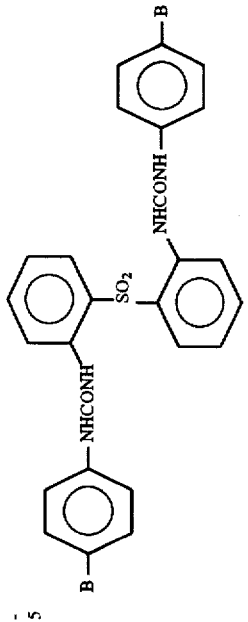
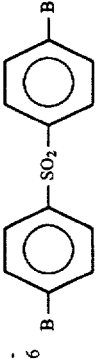
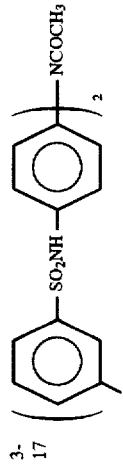
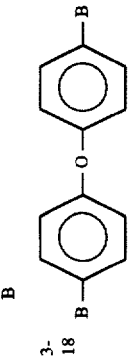

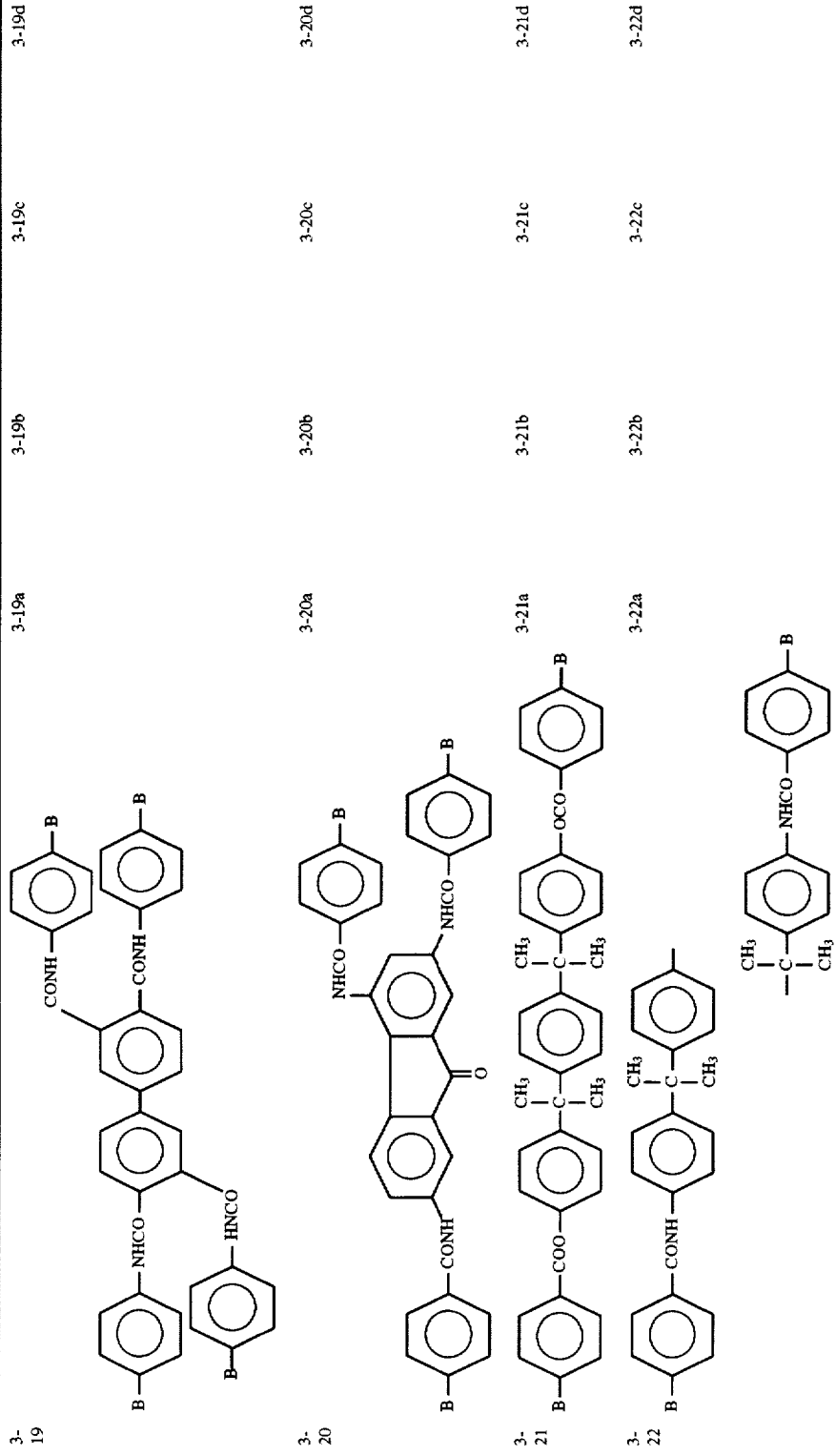

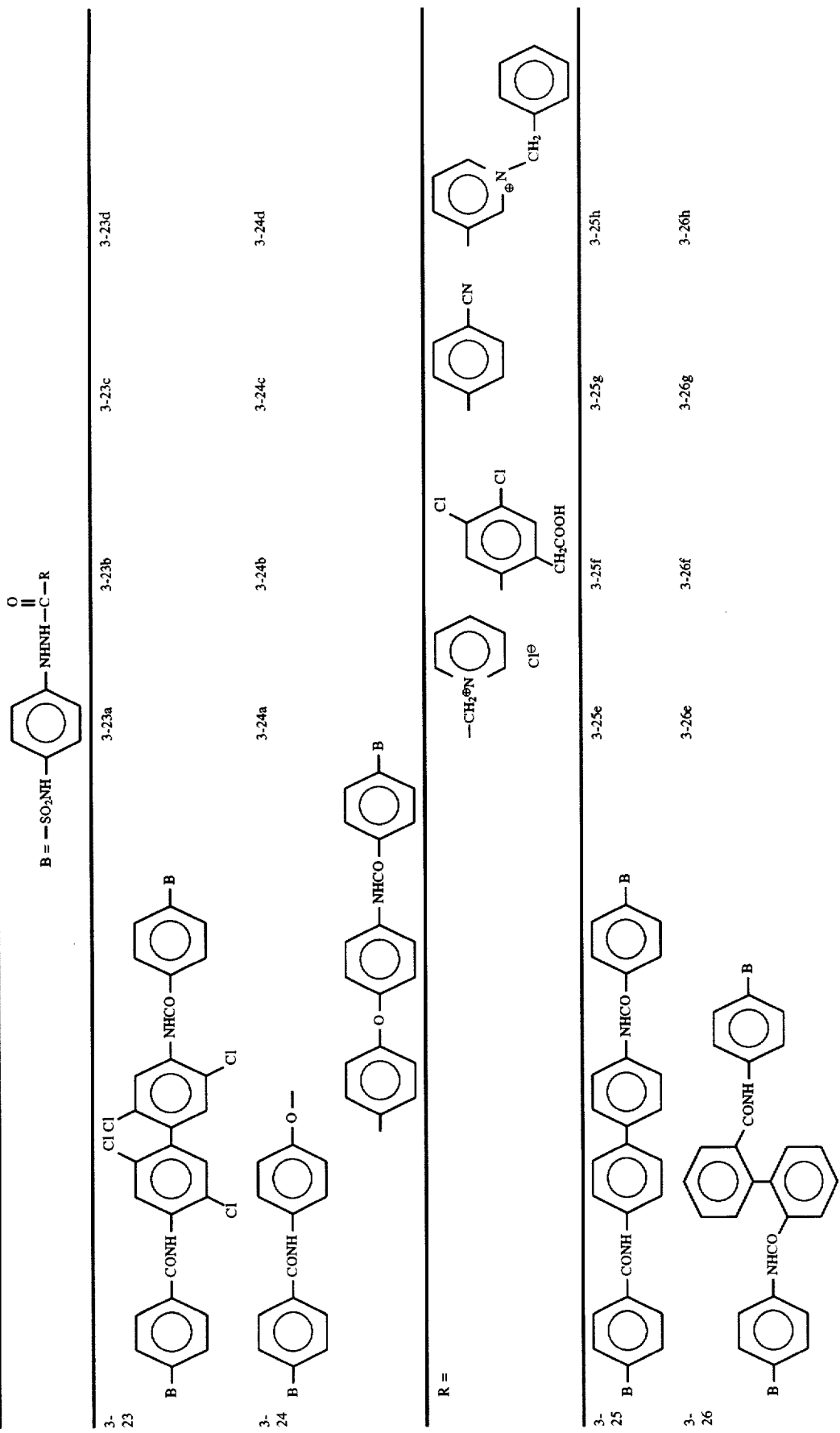

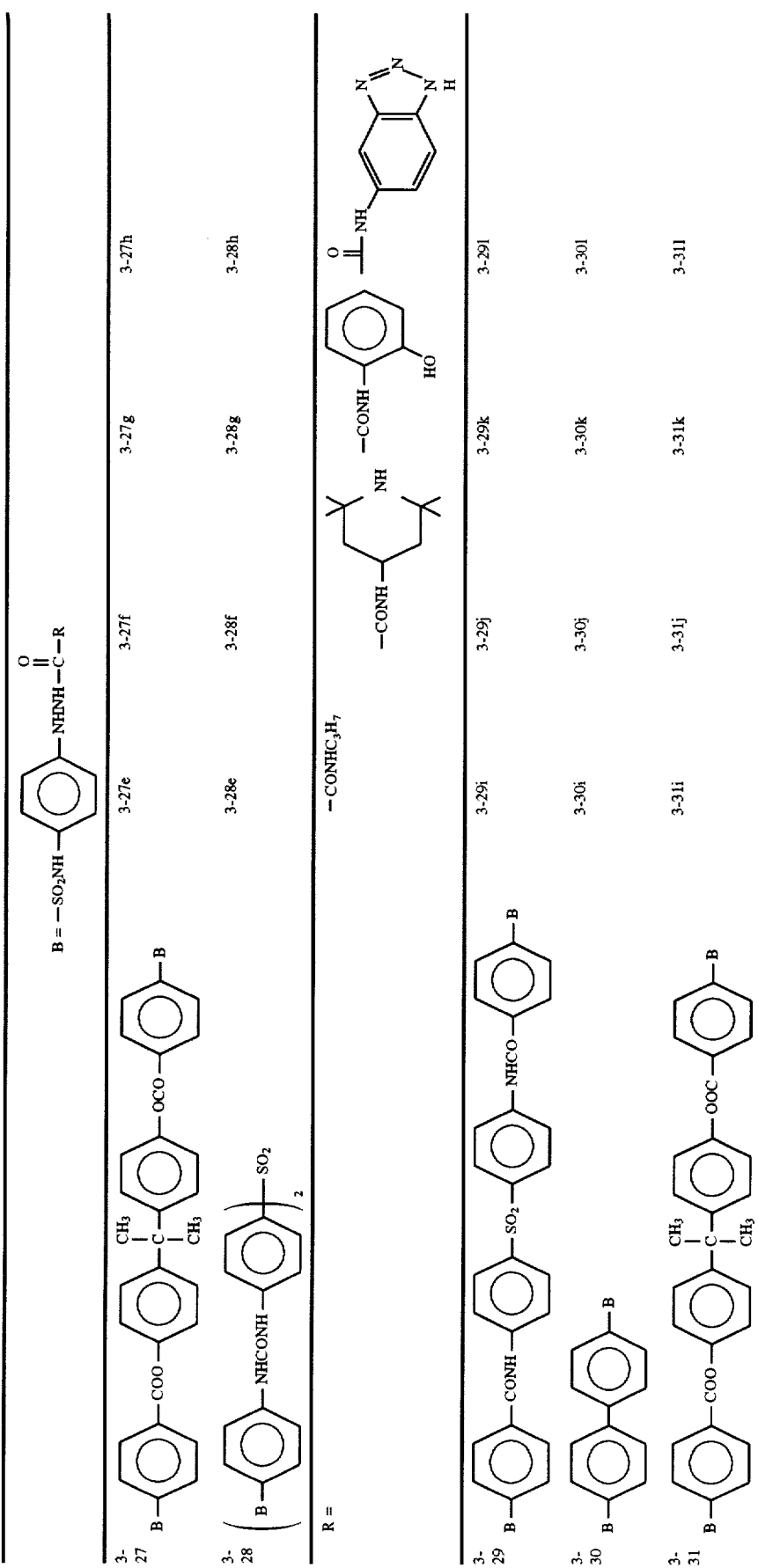

-continued
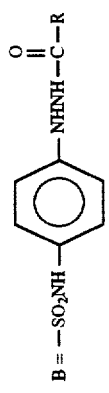
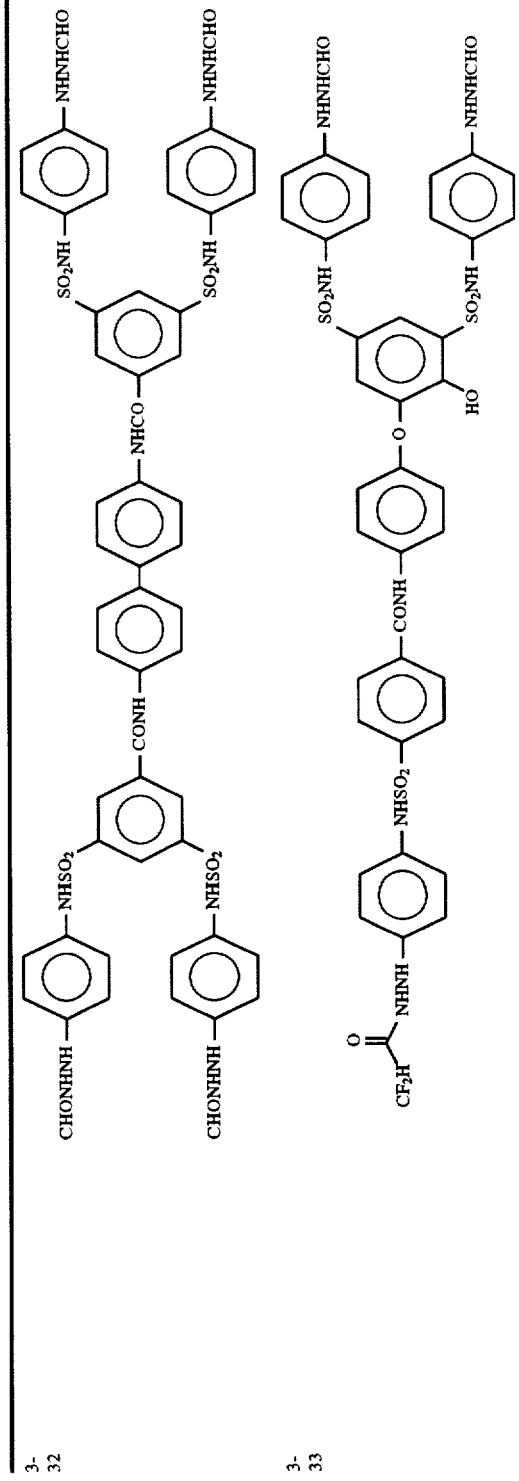

Synthesis Example 1-1

Synthesis of Compound 1-1a

The Compound 1-1a illustrated above was prepared in accordance with the following reaction Scheme 1-1:

resulting mixture was heated under reflux, and then admixed with an iron powder, followed by one-hour stirring. The insoluble matter was removed by Celite filtration, and the filtrate obtained was admixed with 3.7 ml of pyridine and a

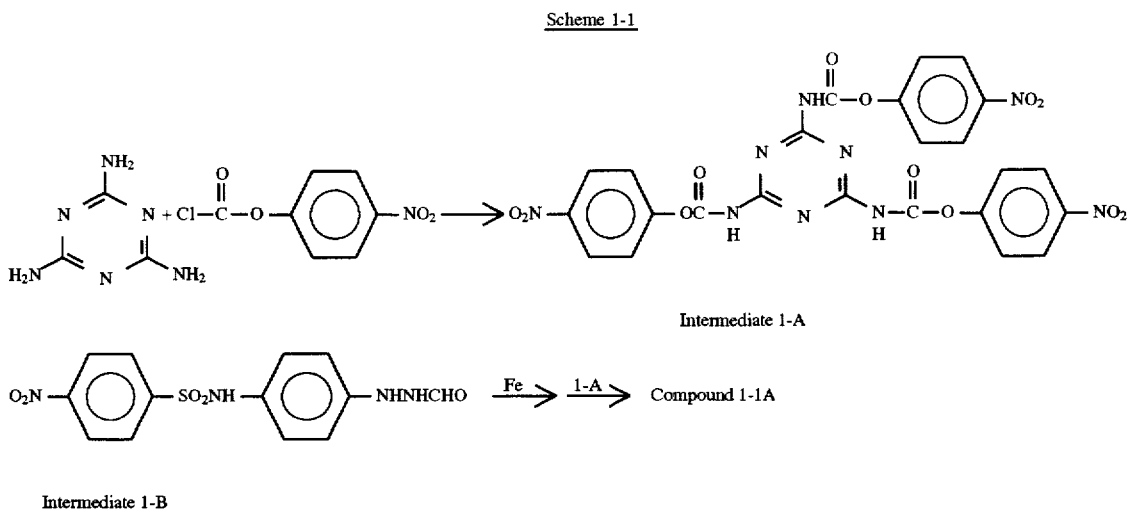

<Synthesis of Intermediate 1-A>

Triethylamine in a volume of 18 ml was added to a solution containing 5.33 g of melamine in 100 ml of acetonitrile, cooled in an ice bath, and then reacted with a solution containing 25.6 g of p-nitrochloroformyloxybenzene in 80 ml of acetonitrile. After one-hour stirring at room temperature, the insoluble matter was filtered out, and the filtrate was admixed with ethyl acetate and dilute hydrochloric acid. Therefrom, the product was extracted, dried and concentrated. Thus, 23.7 g of Intermediate 1-A was obtained.

<Synthesis of Compound 1-1a>

To a 100 ml of isopropyl alcohol solution containing 15.2 g of Intermediate 1-B prepared from p-nitrobenzenesulfonyl chloride and N-p-aminophenyl-N'-formylhydrazine were added 1 g of ammonium chloride and 10 ml of water. The solution containing 9.36 g of Intermediate 1-A in 30 ml of an acetonitrile/dimethylacetamide mixture. The resultant admixture was stirred for one hour. Therefrom, the product was extracted by the addition of ethyl acetate and dilute hydrochloric acid. After drying and concentration, the product was purified by column chromatography on silica gel. Thus, 8.56 g of Compound 1-1a (amorphous) was obtained.

Synthesis Example 1-2

Synthesis of Compound 1-1b

The Compound 1-1b illustrated above was prepared in accordance with the following reaction Scheme 1-2:

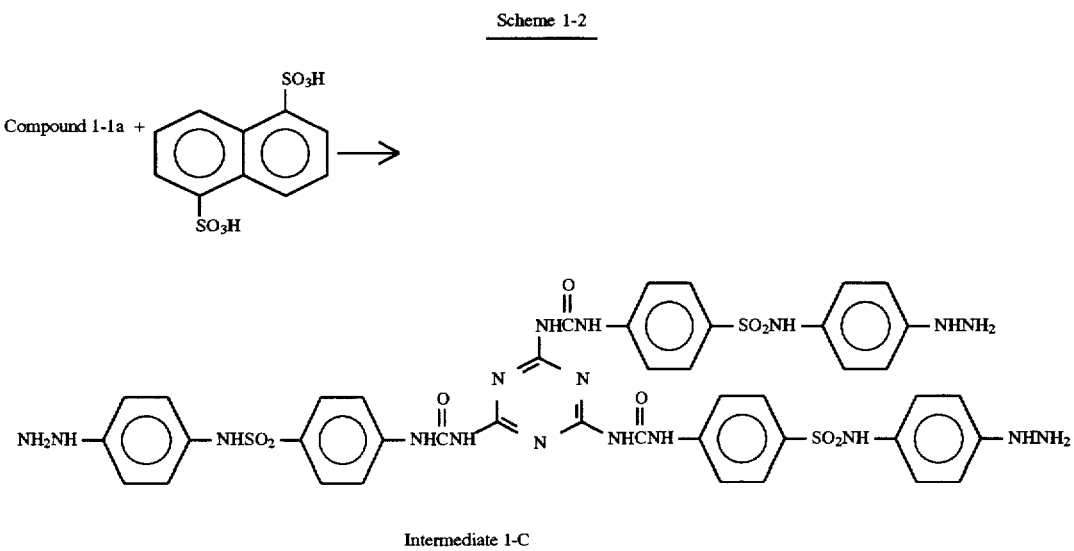

-continued
Scheme 1-2

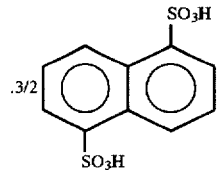

1-C + (CF₃CO)₂O ⟶ Compound 1-1b

<Synthesis of Intermediate 1-C>

A suspension containing 7.84 g of Compound 1-1a and 3.77 g of 1,5-naphthalenedisulfonic acid in 100 ml of a methanol/acetonitrile mixture was stirred for 2 hours at 50° C. Then, the insoluble matter was filtered out, and the residue in an amount of 9.41 g was obtained as Intermediate 1-C.

<Synthesis of Compound 1-1b>

A solution containing 9.41 g of Intermediate 1-C in 100 ml of an acetonitrile/dimethylacetamide mixture was cooled in an ice bath in an atmosphere of nitrogen, and admixed with 2.7 ml of triethylamine and 4.0 g of trifluoroacetic acid anhydride. The resultant mixture was stirred for 1 hour at room temperature, and therefrom the product was extracted by the addition of ethyl acetate and dilute hydrochloric acid. After drying and concentration, the product was purified by column chromatography on silica gel. Thus, 3.15 g of Compound 1-1b (amorphous) was obtained.

Synthesis Example 1-3
Synthesis of Compound 1-32f

A solution containing 4.43 g of imidazole in 100 ml of acetonitrile was cooled in an ice bath, and thereto 2.1 g of oxalyl chloride was added dropwise. The resultant solution was stirred for 1 hour at room temperature, and then the insoluble matter was filtered out. To the filtrate, 1 g of propylamine was added dropwise at room temperature. Further thereto, a solution containing 8.1 g of Intermediate 1-C in 50 ml of acetonitrile was added dropwise, followed by one-hour stirring. From this reaction mixture, the product was extracted by the addition of ethyl acetate and dilute hydrochloric acid. After drying and concentration, the product was purified by column chromatography on silica gel. Thus, 5.53 g of Compound 1-32f (amorphous) was obtained.

Synthesis Example 1-4
Synthesis of Compound 1-17d

The Compound 1-17d illustrated above was prepared in accordance with the following reaction Scheme 1-3:

Scheme 1-3

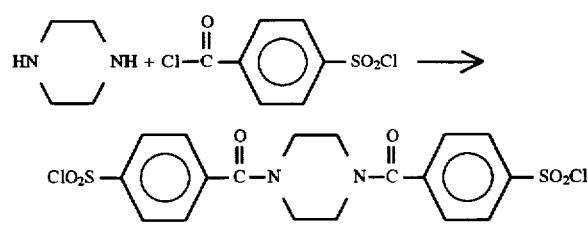

Intermediate 1-D

-continued
Scheme 1-3

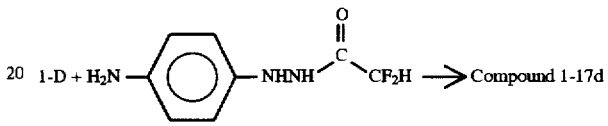

<Synthesis of Intermediate 1-D>

A solution containing 3.2 g of piperazine in 50 ml of an acetonitrile/dimethylacetamide mixture was admixed with 6 ml of pyridine, and thereto a solution containing 17.8 g of p-chlorosulfonylbenzoyl chloride in 50 ml of acetonitrile was added dropwise as it was cooled in an ice bath. From this reaction mixture, the product was extracted by the addition of ethyl acetate and dilute hydrochloric acid. After drying and concentration, the product was purified by column chromatography on silica gel. Thus, 15.6 g of Intermediate 1-D was obtained.

<Synthesis of Compound 1-17d>

To 60 ml of an isopropyl alcohol solution containing 2.9 g of N-p-aminophenyl-N'-difluoroacetylhydrazine obtained by the iron reduction of N-p-nitrophenyl-N'-difluoroacetylhydrazine, 2.9 ml of pyridine was added, and further a solution containing 8.72 g of Intermediate 1-D in 20 ml of an acetonitrile/dimethylacetamide mixture was added, followed by one-hour stirring. From this reaction mixture, the product was extracted by the addition of ethyl acetate and dilute hydrochloric acid. After drying and concentration, the product was purified by column chromatography on silica gel. Thus, 6.55 g of Compound 1-17d (amorphous) was obtained.

Synthesis Example 1-5
Synthesis of Compound 1-33e
<Synthesis of Intermediate 1-F>

An Intermediate 1-F was prepared in the same manner as Intermediate 1-C, except that an Intermediate 1-E prepared from Intermediate 1-D and N-p-aminophenyl-N'-formylhydrazine was used in place of Compound 1-1a.

<Synthesis of Compound 1-33e>

The Compound 1-33e illustrated hereinbefore was synthesized (in an amorphous state) in the same manner as Compound 1-32f, except that 4-amino-2,2,6,6,-tetramethylpiperidine was used in place of propylamine and Intermediate 1-F was used in place of Intermediate 1-C.

Synthesis Example 1-6
Synthesis of Compound 1-33g

The Compound 1-33g illustrated hereinbefore was synthesized in accordance with the following reaction Scheme 1-4:

Scheme 1-4

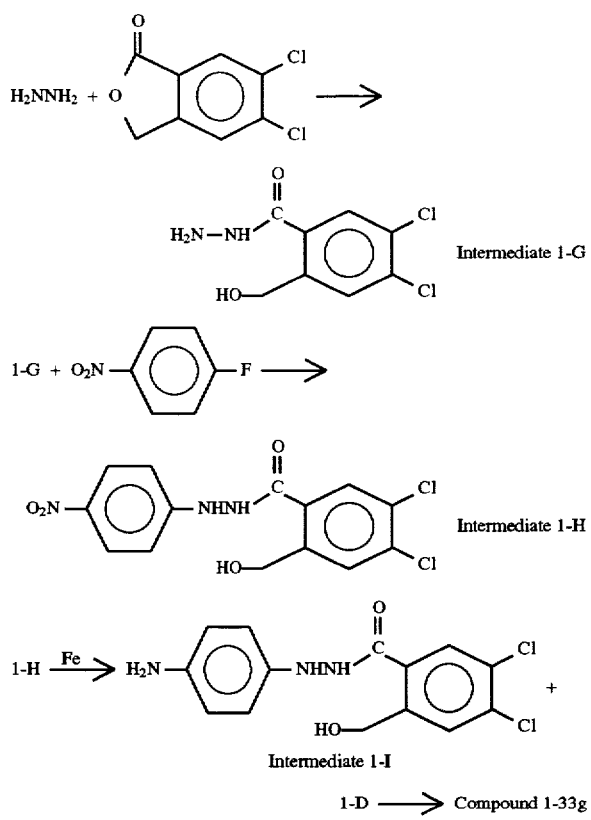

<Synthesis of Intermediate 1-G>

A Dichlorophthalide in an amount of 26.55 g was added little by little to 150 ml of hydrazine hydrate at room temperature, and stirred for 3 hours at room temperature to result in precipitation of a white solid. The white solid was filtered off to obtain 31.5 g of Intermediate 1-H.

<Synthesis of Intermediate 1-H>

To 200 ml of a dimethylformamide solution containing 28.5 g of Intermediate 1-G and 13 ml of p-fluoronitrobenzene, 20 g of potassium carbonate was added little by little in a stream of nitrogen. The resultant mixture was stirred for 2 hours at 80° C. The mixture was poured into water to result in precipitation of a solid. The solid was filtered off to obtain 31.5 g of Intermediate 1-H.

<Synthesis of Compound 1-33g>

To 50 ml of a dimethylacetamide solution containing 9.62 g of Intermediate 1-I obtained by the iron reduction of Intermediate 1-H, 4.1 ml of triethylamine was added and cooled in an ice bath. Thereto, 50 ml of an acetonitrile solution containing 7.25 g of Intermediate 1-D was added dropwise in a stream of nitrogen. The resultant mixture was stirred for 2 hours at room temperature. From this reaction mixture, the product was extracted by the addition of ethyl acetate and dilute hydrochloric acid. After drying and concentration, the product was purified by column chromatography on silica gel. Thus, 8.63 g of Compound 1-33g (amorphous) was obtained.

Synthesis Example 1-7

Synthesis of Compound 1-19d

The Compound 1-19d illustrated hereinbefore was synthesized in accordance with the following reaction Scheme 1-5:

Scheme 1-5

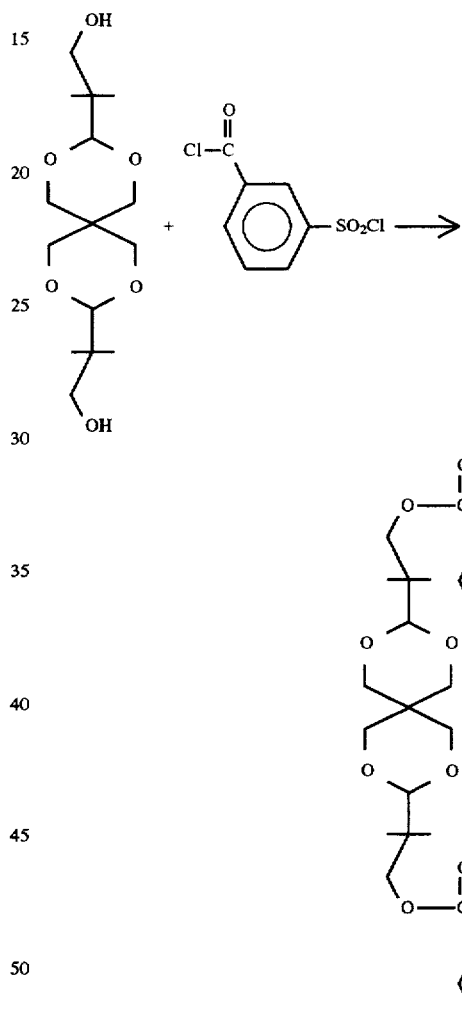

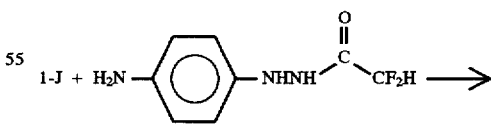

-continued
Scheme 1-5

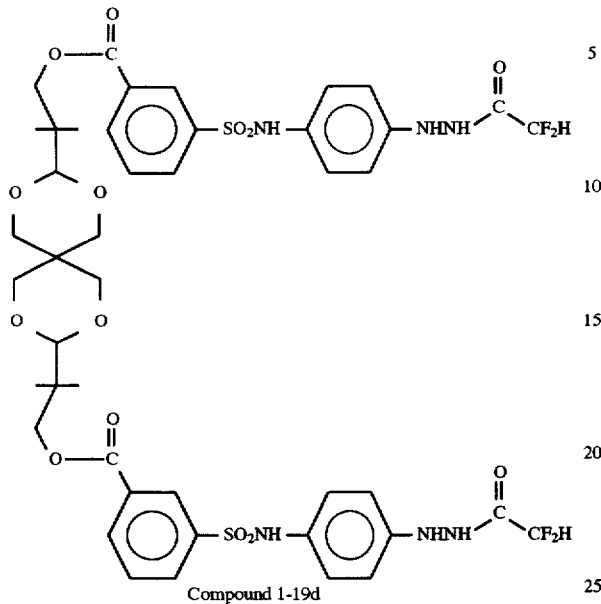

Compound 1-19d

<Synthesis of Intermediate 1-J>

A solution of 3,9-bis(1,1'-dimethyl-2-hydroxyethyl)-2,4,8,10-tetraoxaspiro-[5,5]-undecane in a mixture of acetonitrile with dimethylacetamide was allowed to react with a solution of m-chlorosulfonylbenzoyl chloride in acetonitrile to synthesize Intermediate 1-J.

<Synthesis of Compound 1-19d>

To 60 ml of an isopropyl alcohol solution containing 4.34 g of N-p-aminophenyl-N'-difluoroacetylhydrazine obtained by the iron reduction of N-p-nitrophenyl-N'-difluoroacetylhydrazine, 1.2 ml of pyridine was added, and further a solution containing 5.11 g of Intermediate 1-J in 20 ml of an acetonitrile/dimethylacetamide mixture was added, followed by one-hour stirring. From this reaction mixture, the product was extracted by the addition of ethyl acetate and dilute hydrochloric acid. After drying and concentration, the product was purified by column chromatography on silica gel. Thus, 3.22 g of Compound 1-19d (amorphous) was obtained.

Synthesis Example 1-8

Synthesis of Compound 1-19c

The Compound 1-19c illustrated hereinbefore was synthesized in accordance with the following reaction Scheme 1-6:

Scheme 1-6

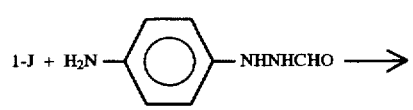

-continued
Scheme 1-6

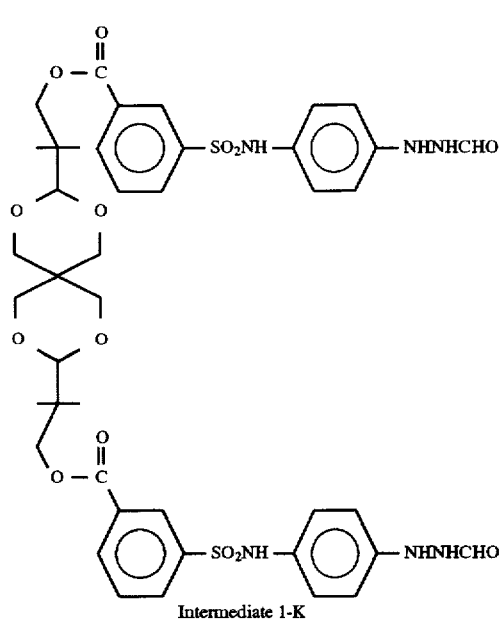

Intermediate 1-K

1-K + 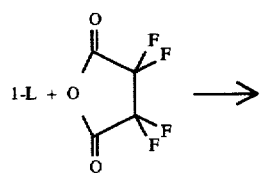 →

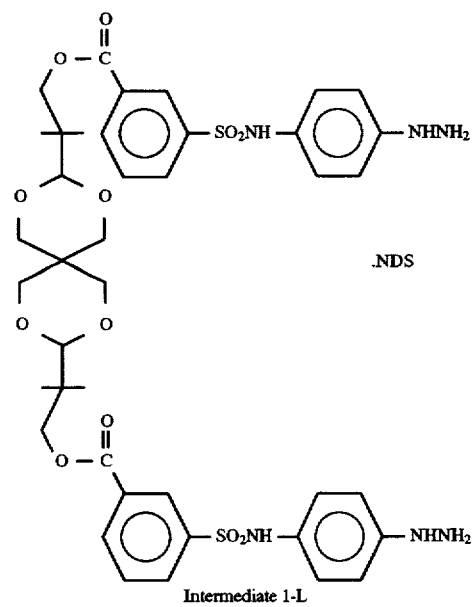

Intermediate 1-L

1-L + O=... →

Scheme 1-6 (continued)

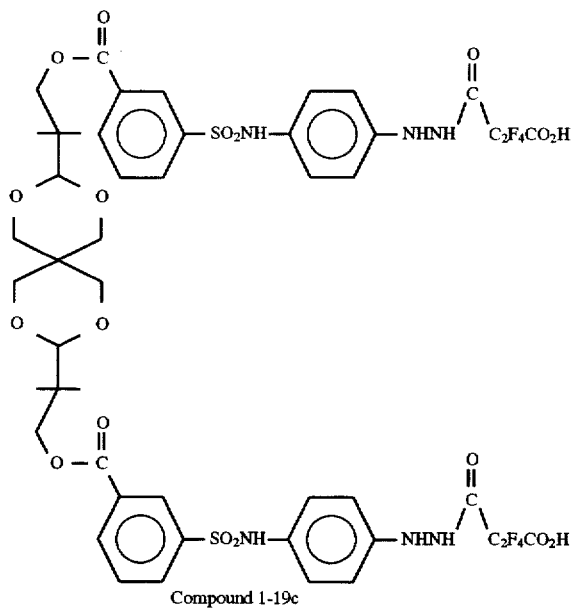

Compound 1-19c

<Synthesis of Intermediate 1-K>

To a dimethylacetamide solution containing 3.16 g of N-p-aminophenyl-N'-formylhydrazine, 6.74 g of Intermediate 1-J was added little by little in an atmosphere of nitrogen as the solution was cooled in an ice bath. Thereafter, the stirring was continued for 3 hours. From this reaction mixture, the product was extracted by the addition of ethyl acetate and dilute hydrochloric acid, and then dried and concentrated. The concentrate obtained was dissolved in dimethylacetamide, and thereto dilute hydrochloric acid was added to crystalize the product. Thus, 6.33 g of Intermediate 1-K was obtained.

<Synthesis of Intermediate 1-L>

A suspension containing 6.33 g of Intermediate 1-K and 2.77 g of 1,5-naphthalenedisulfonic acid in 58 ml of a methanol/acetonitrile mixture was stirred for 2 hours at 50° C. Then, the insoluble matter was filtered out, and the residue in an amount of 8.15 g was obtained as Intermediate 1-L.

<Synthesis of Compound 1-19c>

A solution containing 8.15 g of Intermediate 1-L in 40 ml of an acetonitrile/dimethylacetamide mixture was cooled in an ice bath under an atmosphere of nitrogen, and thereto 2 ml of triethylamine was added. Further thereto, 10 ml of an acetonitrile solution containing 1.6 ml of tetrafluorosuccinic acid anhydride was added dropwise. After conventional after-treatments, 3.15 g of Compound 1-19c (amorphous) was obtained by recrystallization from methylene chloride.

Synthesis Example 1-9
Synthesis of Compound 1-22d

The Compound 1-22d illustrated above was prepared (in an amorphous state) in the same manner as Compound 1-19d, except that 1,4-dioxane-2,3-diol was used in place of 3,9-bis (1,1'-dimethyl-2-hydroxyethyl)-2,4,8,10-tetraoxaspiro-|5.5|-undecane.

Synthesis Example 1-10
Synthesis of Compound 1-5d

The Compound 1-5d illustrated above was prepared (in an amorphous state) in the same manner as Compound 1-19d, except that 2,6-diaminopyridine was used in place of 3,9-bis(1,1'-dimethyl-2-hydroxyethyl)-2,4,8,10-tetraoxaspiro-|5,5|-undecane.

Synthesis Example 1-10
Synthesis of Compound 1-31d

The Compound 1-31d illustrated above was prepared (in an amorphous state) in the same manner as Compound 1-19d, except that 2,4-diamino-6-methoxy-1,3,5-triazine was used in place of 3,9-bis(1,1'-dimethyl-2-hydroxyethyl)-2,4,8,10-tetraoxaspiro-|5,5|-undecane.

Synthesis Example 2-1
Synthesis of Compound 2-1c The Compound 2-1c exemplified above was prepared in accordance with the following reaction Scheme 2-1:

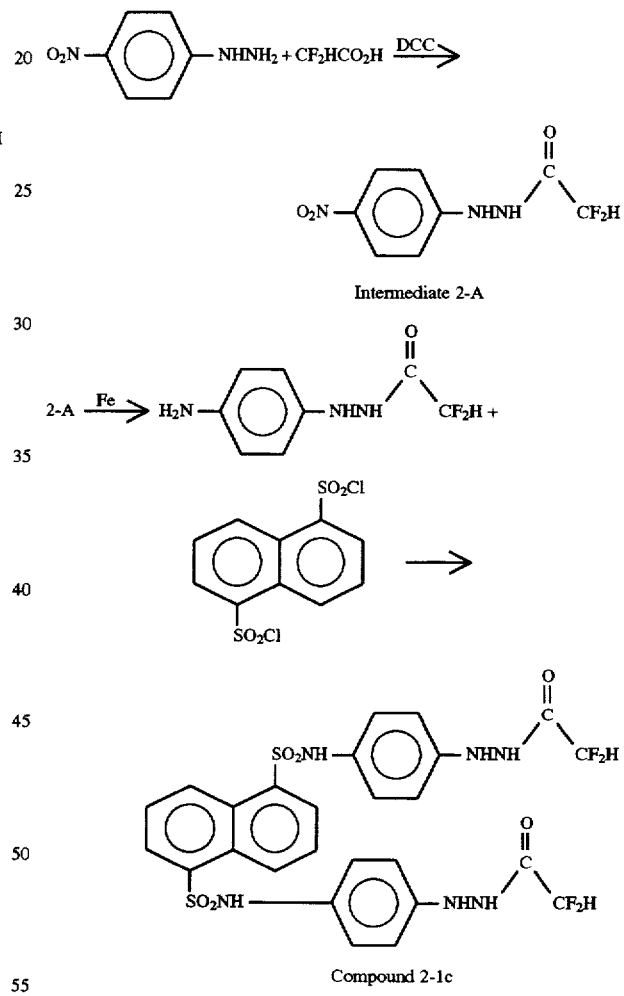

<Synthesis of Intermediate 2-A> p-Nitrophenylhydrazine and difluoroacetic acid were reacted with each other in the presence of dicyclohexylcarbodiimide while they were cooled in an ice bath, thereby preparing Intermediate 2-A.

<Synthesis of Compound 2-1c>

To 100 ml of an isopropyl alcohol solution containing 11.55 g of Intermediate 1-A were added 1 g of ammonium chloride and 10 ml of water. The resulting mixture was heated under reflux, and then admixed with an iron powder, followed by one-hour stirring. The insoluble matter was removed by Celite filtration, and the filtrate obtained was admixed with 2.5 ml of pyridine and a solution containing 5.00 g of 1,5-naphthalenedisulfonyl chloride in 30 ml of an acetonitrile/dimethylacetamide mixture. The resultant admixture was stirred for one hour. Therefrom, the product was extracted by the addition of ethyl acetate and dilute hydrochloric acid. After drying and concentration, the product was purified by column chromatography on silica gel. Thus, 2.27 g of Compound 2-1c (mp. 275°–277° C.) was obtained.

Synthesis Example 2-2

Synthesis of Compounds 2-1a and 2-1d

The Compounds 2-1a and 2-1d exemplified above were prepared in accordance with the following reaction Scheme 2-2:

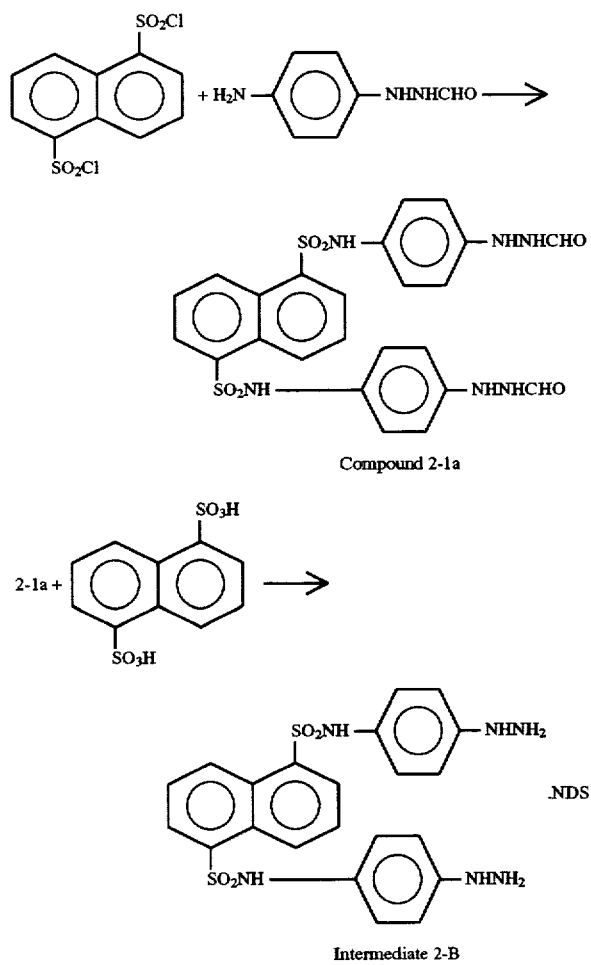

-continued
Scheme 2-2

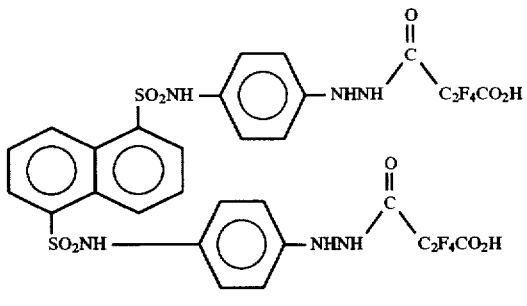

Compound 2-1d

<Synthesis of Compound 2-1a>

A dimethylacetamide solution containing 9.10 g of N-p-aminophenyl-N'-formylhydrazine was cooled in an ice bath in an atmosphere of nitrogen, and thereto 8.90 g of 1,5-naphthalenedisulfonyl chloride was added gradually, followed by 3-hour stirring. From the reaction mixture thus obtained, the product was extracted by the addition of ethyl acetate and dilute hydrochloric acid, dried, and then concentrated. The concentrate was dissolved in dimethylacetamide, and therefrom the product was crystallized by the addition of dilute hydrochloric acid. Thus, 10.10 g of Compound 2-1a (amorphous) was obtained.

<Synthesis of Intermediate 2-B>

58 ml of a suspension containing 10.10 g of Compound 1a and 7.30 g of 1,5-naphthalenedisulfonic acid in a methanol/acetonitrile mixture was stirred for 2 hours at 50° C. The insoluble matter generated therein was filtered off, thereby obtaining 10.21 g of Intermediate 2-B.

<Synthesis of Compound 2-1d>

A solution containing 6.71 g of Intermediate 2-B in 80 ml of an acetonitrile/dimethylacetamide mixture was cooled in an ice bath in an atmosphere of nitrogen, and thereto 3.2 ml of triethylamine was added. Further thereto, 10 ml of an acetonitrile solution containing 2.2 ml of trifluorosuccinic acid anhydride was added dropwise. After conventional operations as after-treatment, the product was recrystallized from methylene chloride. Thus, 2.52 g of Compound 2-1d (amorphous) was obtained.

Synthesis Example 2-3

Synthesis of Compound 2-9c

The Compound 2-9c exemplified above were prepared in accordance with the following reaction Scheme 2-3:

Scheme 2-3

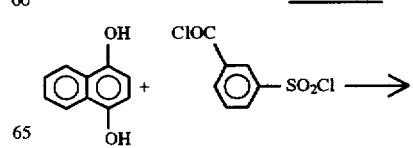

-continued
Scheme 2-3

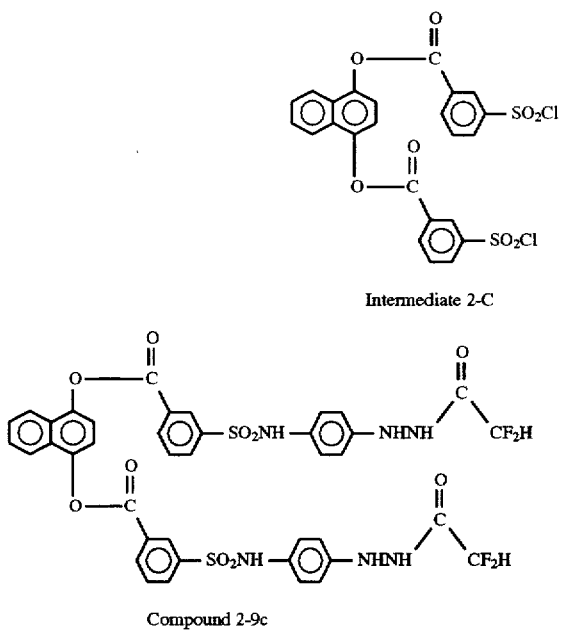

<Synthesis of Intermediate 2-C>

A solution containing 25 g of m-chlorosulfonylbenzoic acid chloride in 80 ml of acetonitrile was added dropwise to a solution containing 7.3 g of 1,4-dihydoxynaphthalene in 100 ml of acetonitrile, and stirred for 1 hour. Therefrom, the product was extracted by the addition of ethyl acetate and dilute hydrochloric acid. The extract obtained was dried, concentrated, and then recrystallized from a mixture of ethyl acetate with methylene chloride. Thus, 15 g of Intermediate 2-C was obtained.

<Synthesis of Compound 2-9c>

The exemplified Compound 2-9c was synthesized in the same manner as in Synthesis of Compound 2-1c, except that Intermediate 2-C was used in place of 1,5-naphthalenedisulfonyl chloride. (amorphous)

Synthesis Example 2-4

<Synthesis of Compound 2-11c>

The exemplified Compound 2-11c was synthesized in the same manner as in Synthesis of Compound 2-9c, except that 1,8-diaminonaphthalene was used in place of 1,4-dihydroxynaphthalene. (amorphous)

Synthesis Example 2-5

Synthesis of Compounds 2-15a and 2-15d

The exemplified Compounds 2-15a and 2-15d were prepared in accordance with the following reaction Scheme 2-4:

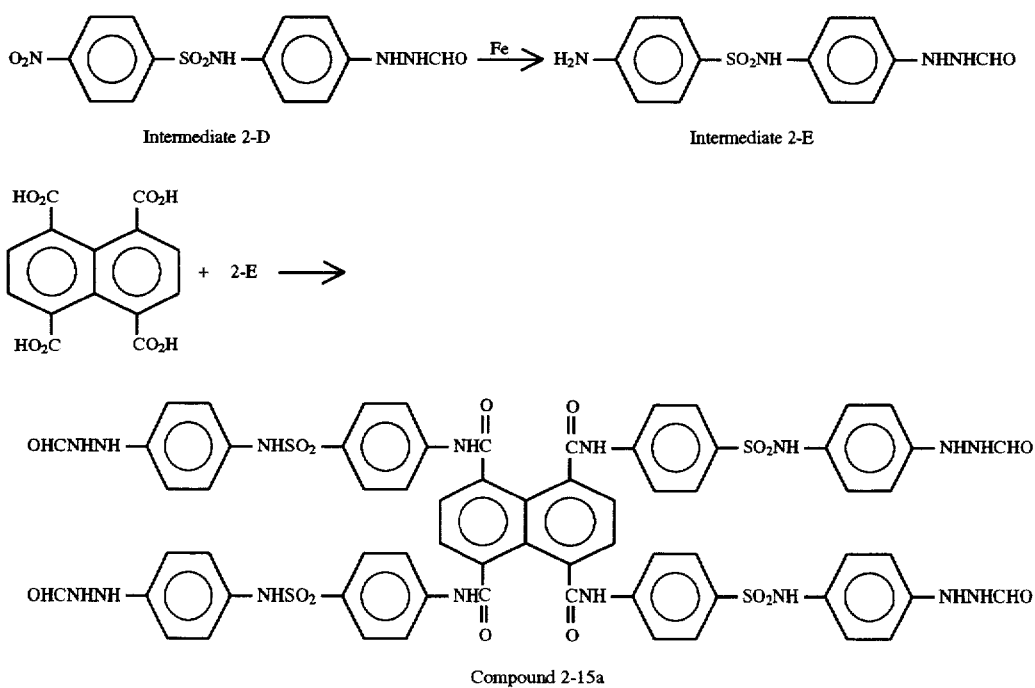

Synthesis of Intermediate 2-E

To 100 ml of an isopropyl alcohol solution containing 19.0 g of Intermediate 2-D prepared from p-nitrobenzenesulfonyl chloride and N-p-aminophenyl-N'-formylhydrazine were added 1 g of ammonium chloride and 10 ml of water. The resulting mixture was heated under reflux, and then admixed with an iron powder, followed by one-hour stirring. From the reaction mixture obtained, the insoluble matter was removed by Celite filtration, and the solvent was distilled away. The product thus obtained was recrystallized from methylene chloride, thereby obtaining 13.9 g of Intermediate 2-E.

Synthesis of Compound 2-15a

In the presence of 9.3 g of dicyclohexylcarbodiimide, a solution containing 13.9 g of Intermediate 2-E in 80 ml of acetonitrile was added dropwise to a solution containing 3.45 g of 1,4,5,8-naphthalenetetracarboxylic acid in 70 ml of acetonitrile, followed by one-hour stirring. The precipitated solid was filtered out, and then the product was extracted by the addition of ethyl acetate and dilute hydrochloric acid, dried and concentrated, followed by recrystallization from a mixture of ethyl acetate with methylene chloride. Thus, 12.2 g of Compound 2-15a (amorphous) was obtained.

Synthesis of Compound 2-15d

The exemplified Compound 2-15d was synthesized in the same manner as in Synthesis of Compound 2-1d, except that Compound 2-15a was used in place of Compound 2-1a. (amorphous)

Synthesis Example 3-1

Synthesis of Compound 3-1c

The Compound 3-1c exemplified above was prepared in accordance with the following reaction Scheme 3-1:

Scheme 3-1

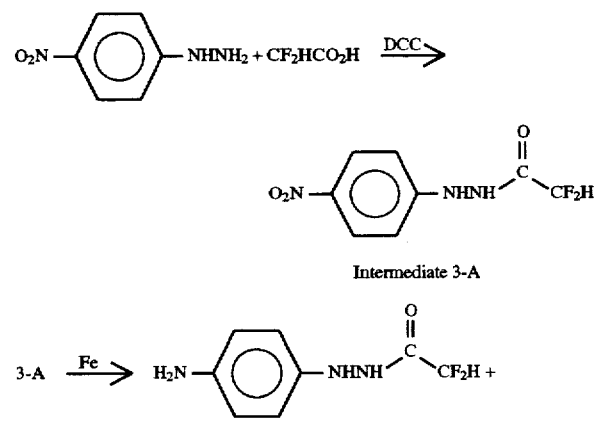

-continued
Scheme 3-1

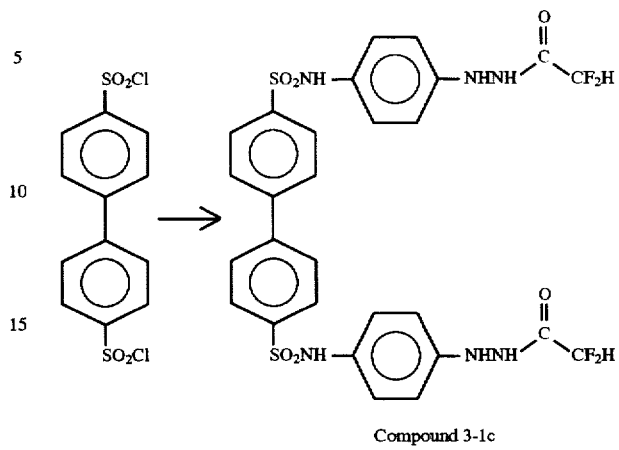

Compound 3-1c

Synthesis of Intermediate 3-A p-Nitrophenylhydrazine and difluoroacetic acid were reacted with each other in the presence of dicyclohexylcarbodiimide while they were cooled in an ice bath, thereby preparing Intermediate 3-A.

Synthesis of Compound 3-1c

To 100 ml of an isopropyl alcohol solution containing 10.32 g of Intermediate 3-A were added 1 g of ammonium chloride and 10 ml of water. The resulting mixture was heated under reflux, and then admixed with an iron powder, followed by one-hour stirring. The insoluble matter was removed by Celite filtration, and the filtrate obtained was admixed with 2.3 ml of pyridine and a solution containing 5.02 g of 4,4'-biphenyldisulfonyl chloride in 30 ml of an acetonitrile/dimethylacetamide mixture. The resultant admixture was stirred for one hour. Therefrom, the product was extracted by the addition of ethyl acetate and dilute hydrochloric acid. After drying and concentration, the product was purified by column chromatography on silica gel. Thus, 1.95 g of Compound 3-1c (mp. 288°–290° C.) was obtained.

Synthesis Example 3-2

Synthesis of Compounds 3-1a

The Compound 3-1a exemplified above was prepared in accordance with the following reaction Scheme 3-2:

Scheme 3-2

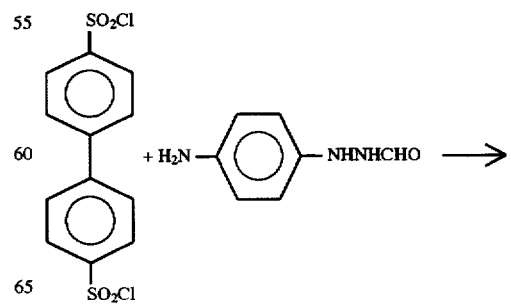

-continued
Scheme 3-2

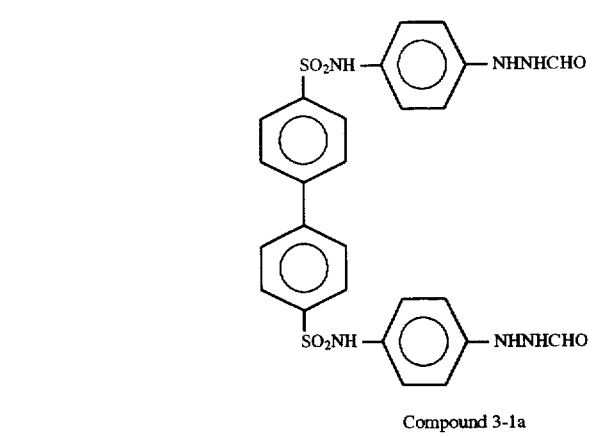

Compound 3-1a

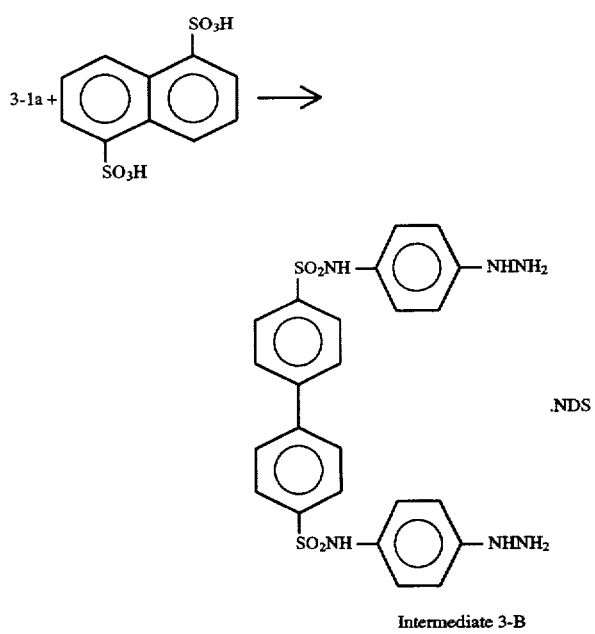

Intermediate 3-B

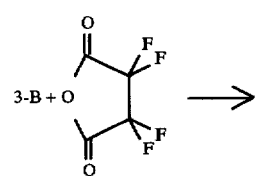

-continued
Scheme 3-2

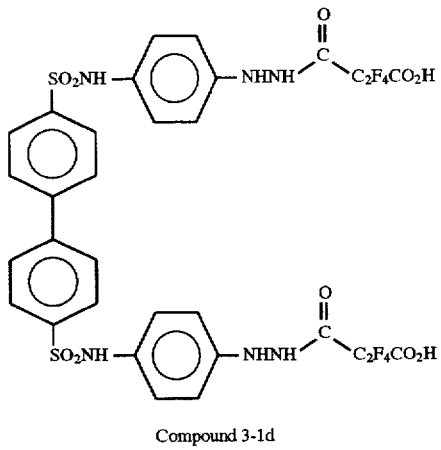

Compound 3-1d

<Synthesis of Compound 3-1a>

A dimethylacetamide solution containing 10.01 g of N-p-aminophenyl-N'-formylhydrazine was cooled in an ice bath in an atmosphere of nitrogen, and thereto 9.79 g of 4,4'-biphenyldisulfonyl chloride was added gradually, followed by 3-hour stirring. From the reaction mixture thus obtained, the product was extracted by the addition of ethyl acetate and dilute hydrochloric acid, dried, and then concentrated. The concentrate was dissolved in dimethylacetamide, and therefrom the product was crystallized by the addition of dilute hydrochloric acid. Thus, 11.11 g of Compound 3-1a (amorphous) was obtained.

Synthesis Example 3-3

Synthesis of Compound 3-1d

The Compound 3-1d exemplified above was prepared in accordance with the above reaction Scheme 3-2.

<Synthesis of Intermediate 3-B>

60 ml of a suspension containing 11.11 g of Compound 1a and 8.03 g of 1,5-naphthalenedisulfonic acid in a methanol/acetonitrile mixture was stirred for 2 hours at 50° C. The insoluble matter generated therein was filtered off, thereby obtaining 11.23 g of Intermediate 3-B.

<Synthesis of Compound 3-1d>

A solution containing 7.38 g of Intermediate 3-B in 80 ml of an acetonitrile/dimethylacetamide mixture was cooled in an ice bath in an atmosphere of nitrogen, and thereto 3.5 ml of triethylamine was added. Further thereto, 10 ml of an acetonitrile solution containing 2.4 ml of trifluorosuccinic acid anhydride was added dropwise. After conventional operations as after-treatment, the product was recrystallized from methylene chloride. Thus, 3.78 g of Compound 3-1d (amorphous) was obtained.

Synthesis Example 3-4
Synthesis of Compound 3-11c

The Compound 3-11c exemplified above were prepared in accordance with the following reaction Scheme 3-3:

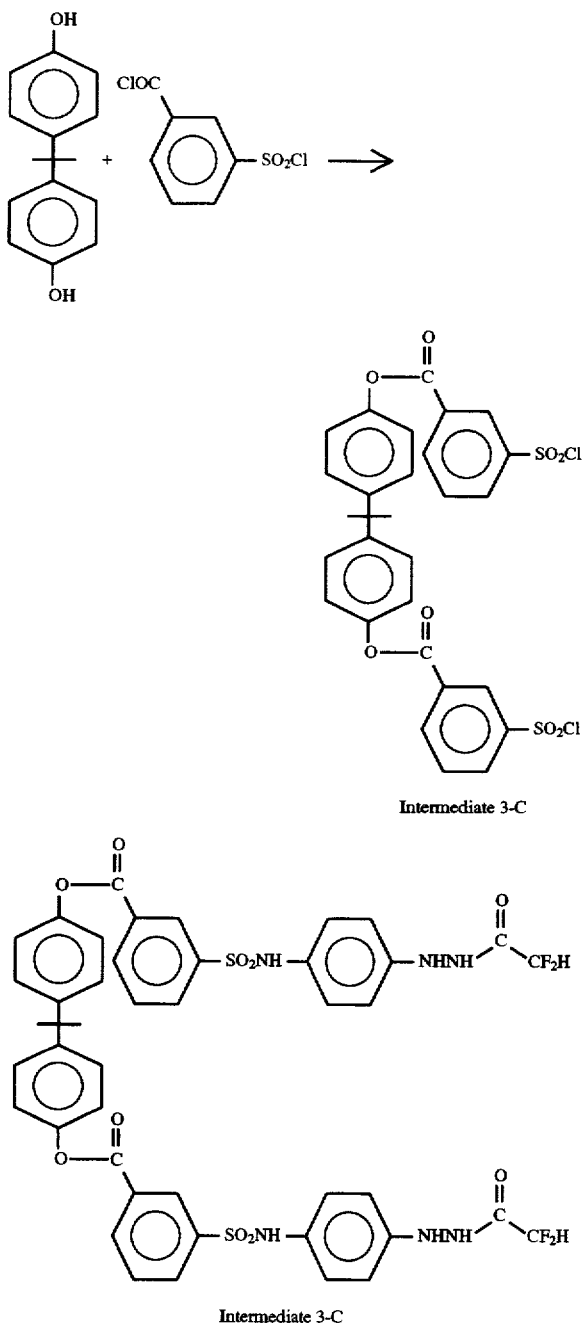

<Synthesis of Intermediate 3-C>

A solution containing 35.2 g of m-chlorosulfonylbenzoic acid chloride in 80 ml of acetonitrile was added dropwise to a solution containing 17.2 g of 2,2'-bis(4-hydroxyphenyl) propane in 70 ml of acetonitrile, and stirred for 1 hour. Therefrom, the product was extracted by the addition of ethyl acetate and dilute hydrochloric acid. The extract obtained was dried, concentrated, and then recrystallized from a mixture of ethyl acetate with methylene chloride. Thus, 28.2 g of Intermediate 3-C was obtained.

<Synthesis of Compound 3-11c>

The exemplified Compound 3-11c was synthesized in the same manner as in Synthesis of Compound 3-1c, except that Intermediate 3-C was used in place of 1,5-naphthalenedisulfonyl chloride. (amorphous)

Synthesis Example 5
<Synthesis of Compound 3-16c>

The exemplified Compound 3-16c was synthesized in the same manner as in Synthesis of Compound 3-11c, except that 4,4'-diaminodiphenylsulfide was used in place of 2,2'-bis(4-hydroxyphenyl)propane. (amorphous)

Synthesis Example 3-6
<Synthesis of Compound 3-5c>

The exemplified Compound 3-5c was synthesized in the same manner as in Synthesis of Compound 3-11c, except that 1,1'-bis-2-naphthol was used in place of 2,2'-bis(4-hydroxyphenyl)propane. (amorphous)

The hydrazide compounds according to the present invention (hydrazine nucleating agent) can be used in the form of solution in an appropriate water-miscible organic solvent, such as an alcohol (e.g., methanol, ethanol, propanol, fluorinated alcohols), a ketone (e.g., acetone, methyl ethyl ketone), dimethylformamide, dimethyl sulfoxide or methyl cellosolve.

Also, it is possible to use the present hydrazine nucleating agent in the form of emulsified dispersion, which is prepared according to a well-known emulsifying dispersion process. Specifically, the hydrazine nucleating agent is dissolved in a combination of an oil, such as dibutyl phthalate, tricresyl phosphate, glyceryl triacetate or diethyl phthalate, with an auxiliary solvent, such as ethyl acetate or cyclohexane, and then dispersed mechanically in the form of emulsion. In addition, it is also possible to use the present hydrazine nucleating agent in the form of solid dispersion, which is prepared according to a known solid dispersion process, specifically by dispersing the finely divided nucleating agent into water by means of a ball mill, a colloid mill or ultrasonic waves.

However, it is preferable for the present hydrazine nucleating agent to be used as a dispersion of finely divided solid (microcrystalline grains). The finely divided (crystalline) solid dispersion of hydrazine nucleating agent can be prepared mechanically using a known finely grinding means (e.g., a ball mill, a vibrational ball mill, a planetary ball mill, a sand mill, a colloid mill, a jet mill, a roller mill) in the presence of a dispersing agent and, if needed, an appropriate solvent (e.g., water, alcohol). Further, the fine grains (crystals) of hydrazine nucleating agent can be prepared in other manners. In one manner, for instance, the hydrazine nucleating agent is dissolved in an appropriate solvent with the aid of a surfactant for dispersion, and then added to a poor solvent for the hydrazine nucleating agent to precipitate as microcrystals. In another manner, the hydrazine nucleating agent is dissolved by controlling the pH, and then microcrystallized by changing the pH. The layer containing a fine powder of the hydrazine nucleating agent can be formed by coating an intended support with a solid dispersion comprising almost uniform grains prepared by dispersing the fine grains (crystals) of hydrazine nucleating agent obtained above into an appropriate binder. On the other hand, such a layer can also be formed by applying the hydrazine nucleating agent in the form of salt in a dissociated condition, and further applying thereon an acidic gelatin to fix the dispersed state.

Examples of a binder used therein include active methylene-containing polymers, and hydrophilic colloids and synthetic polymers usable in light-sensitive emulsion layers and light-insensitive layers. As to the hydrophilic colloids, though there is no particular restriction, gelatin is generally preferred.

With respect to the surfactant for dispersion, known surfactants, preferably anionic, nonionic and amphoteric ones, can be used. In particular, anionic and/or nonionic surfactants are used to advantage.

The fine grains of hydrazine nucleating agent in a solid dispersion have an average grain size of from 0.005 to 10 µm, preferably from 0.01 to 1 µm, more preferably from 0.01 to 0.5 µm.

The present hydrazine nucleating agent may be incorporated in any of layers arranged on the silver halide emulsion layer side of a support, including silver halide emulsion layers and other hydrophilic colloid layers. However, it is preferable for the present nucleating agent to be incorporated in a silver halide emulsion layer or a hydrophilic colloid layer adjacent to a silver halide emulsion layer.

The amount of the present nucleating agent added per mole of silver halide is preferably from b $1\times10^{-6}$ to $1\times10^{-2}$ mole, more preferably from $1\times10^{-5}$ to $1\times10^{-3}$ mole, and most preferably from $5\times10^{-5}$ to b $1\times10^{-3}$ mole.

In processing the silver halide photographic photosensitive material, in particular with a developer having a pH value of below 11, it is preferable that a nucleation accelerator, such as an amine derivative, an onium salt, a disulfide derivative or a benzyl alcohol derivative, be added to a silver halide emulsion layer or another hydrophilic colloid layer.

Examples of the nucleation accelerator for use in the present invention, amine derivatives, onium salts, disulfide derivatives and hydroxymethyl derivatives. More specifically, those derivatives are recited below:

- the compounds described in JP-A-07-77783 (page 48, lines 2–37), with the specific examples including Compounds A-1) to A-73) illustrated at pages 49 to 58;
- the compounds represented by formulae [Ka-21], [Ka-22] and [Ka-23] respectively in JP-A-07-84331, with specific examples including those illustrated at pages 6–8;
- the compounds represented by formulae [Na] and [Nb] respectively in JP-A-07-104426, with specific examples including Compounds Na-1 to Na-22 and Compounds Nb-1 to Nb-12 illustrated at pages 16–22; and
- Such a nucleation accelerator as recited above can be used in the form of solution in an appropriate water-miscible organic solvent, such as an alcohol (e.g., methanol, ethanol, propanol, fluorinated alcohols), a ketone (e.g., acetone, methyl ethyl ketone), dimethylformamide, dimethyl sulfoxide or methyl cellosolve.

Also, it is possible to use the nucleation accelerator in the form of emulsified dispersion, which is prepared according to a well-known emulsifying dispersion process. Specifically, the nucleation accelerator is dissolved in a combination of an oil, such as dibutyl phthalate, tricresyl phosphate, glyceryl triacetate or diethyl phthalate, with an auxiliary solvent, such as ethyl acetate or cyclohexane, and then dispersed mechanically in the form of emulsion. In addition, it is also possible to use the nucleation accelerator in the form of solid dispersion, which is prepared according to a known solid dispersion process, specifically by dispersing the finely divided nucleation accelerator into water by means of a ball mill, a colloid mill or ultrasonic waves.

The nucleation accelerator for use in the present invention may be incorporated in any of layers arranged on the silver halide emulsion layer side of a support, including silver halide emulsion layers and other hydrophilic colloid layers. However, it is preferable for the nucleation accelerator to be incorporated in a silver halide emulsion layer or a hydrophilic colloid layer adjacent to a silver halide emulsion layer.

In the present invention, the amount of a nucleation accelerator added per mole of silver halide is preferably from $1\times10^{-6}$ to $2\times10^{-2}$ mole, more preferably from $1\times10^{-5}$ to $2\times10^{-2}$ mole, and most preferably from $2\times10^{-5}$ to $1\times10^{-2}$ mole.

The silver halide emulsions for use in the present invention have no particular restrictions as to halide composition. In order to more effectively achieve the objects of the present invention, however, it is preferable for the halide composition to have a chloride content of at least 50 mole %. In other words, silver chloride, silver chlorobromide or silver chloroiodobromide having a chloride content of at least 50 mole % is advantageous to the present invention. The silver halides for use in the present invention have preferably an iodide content of below 5 mole %, particularly preferably below 2 mole %.

When the present photosensitive material is intended to be used as a photosensitive material for high illumination intensity exposure, such as scanner exposure, or a photosensitive material for photographing line originals, a rhodium compound is incorporated therein for the purpose of achieving high contrast and low fog.

As for the rhodium compound, water-soluble rhodium compounds can be used in the present invention. Examples such a rhodium compound include halogenated rhodium(III) compounds and rhodium complex salts having as ligands halogen atoms, amines, oxalato, etc., such as hexachlororhodium(III) complex salts, hexabromorhodium (III) complex salts, hexaamminerhodium(III) complex salts and trioxalatorhodium(III) complex salts. These rhodium compounds is used in the form of solution in water or an appropriate solvent. In order to stabilize the solution of a rhodium compound, a prevailing method which comprises adding an aqueous solution of hydrogen halide (e.g., hydrochloric acid, hydrobromic acid, hydrofluoric acid) or alkali halide (e.g., KCl, NaCl, KBr, NaBr)can be adopted. In stead of using a water-soluble rhodium compound, it is also possible to add other silver halide grains doped in advance by rhodium to a silver halide emulsion, and dissolving the grains therein.

The amount of a water-soluble rhodium compound added is from $1\times10^{-8}$ to $5\times10^{-6}$ mole, preferably from $5\times10^{-8}$ to $1\times10^{-6}$ mole, per mole of silver in a silver halide emulsion.

Such a compound can be properly added during the preparation of emulsion grains or at any stage before the coating of an emulsion. In particular, it is preferable to add the compound at the time of emulsion-making, thereby incorporating the compound into the grains of silver halide.

The photographic emulsions employed in the present invention can be prepared using various methods as described in, for example, P. Glafkides, *Chimie et Phisigue Photographigue*, Paul Montel (1967), G. F. Duffin, *Photographic Emulsion Chemistry*, The Focal Press (1966), and V. L. Zelikman et al., *Making and Coating Photographic Emulsion*, The Focal Press (1964).

Suitable methods for reacting a water-soluble silver salt with a water-soluble halide include, e.g., a single jet method, a double jet method or a combination thereof.

Also, a method in which silver halide grains are produced in the presence of excess silver ion (the so-called reverse mixing method) can be employed in the present invention. On the other hand, the so-called controlled double jet method, in which the pAg of the liquid phase in which silver halide grains are to be precipitated is maintained constant, may be also employed therein. Further, it is also preferable to form emulsion grains in the presence of the so-called silver halide solvent, such as ammonia, a thioether or a tetrasubstituted thiourea. Of the silver halide solvents, tetrasubstituted thiourea compounds are more preferred, which are described in JP-A-053-82408 and JP-A-55-77737. In particular, tetramethylthiourea and 1,3-dimethyl-2-imidazolidinethione are preferred over the others.

In accordance with the controlled double jet method or the method of forming emulsion grains in the presence of a silver halide solvent, it is easy to prepare a silver halide emulsion having a regular crystal form and a narrow grain-size distribution. Therefore, those methods are favorable for the preparation of silver halide emulsions used in the present invention.

In order to render the grain size uniform, it is preferable to grow the emulsion grains as fast as possible within the limit of critical saturation by using the method of varying the addition speeds of silver nitrate and alkali halides depending on the grain growth speed, as described in British Patent 1,535,016, JP-B-48-36890 and JP-B-52-16364, or the method of varying the concentrations of water solutions as described in British Patent 4,242,445 and JP-A-55-158124.

The emulsions for use in the present invention are preferably monodisperse emulsions having a variation coefficient of not greater than 20%, particularly preferably not greater than 15%, with respect to grain size.

The average size of grains in the monodisperse silver halide emulsion is not greater than 0.5 µm, particularly preferably from 0.1 to 0.4 µm.

It is preferred for the silver halide emulsions of the present invention to be chemically sensitized. For chemical sensitization, known methods, such as a sulfur sensitization method, a selenium sensitization method, a tellurium sensitization method and a precious metal sensitization method, can be used individually or in combination of two or more thereof. Suitable combinations of those methods are, e.g., a combination of sulfur and gold sensitization methods, a combination of sulfur, selenium and gold sensitization methods and a combination of sulfur, tellurium and gold sensitization methods.

The sulfur sensitization in the present invention is generally accomplished by adding a sulfur sensitizer to an emulsion and stirring the emulsion for a definite time at a high temperature of 40° C. or above. As for the sulfur sensitizer, known compounds can be used. Examples thereof include the sulfur compounds contained in gelatin and various sulfur compounds, such as thiosulfates, thioureas, thiazoles and rhodanines. Of these compounds, thiosulfates and thiourea compounds are preferred. The appropriate amount of a sulfur sensitizer added depends on the pH and the temperature during the chemical ripening, the grain size of silver halide and other various conditions. In general, however, the amount of a sulfur sensitizer added ranges from $10^{-7}$ to $10^{-2}$ mole, preferably from $10^{-5}$ to $10^{-3}$ mole, per mole of silver halide.

As for the selenium sensitizer, known selenium compounds can be used in the present invention. In general, selenium sensitization can be achieved by adding a labile and/or non-labile selenium compound to an emulsion and stirring the emulsion for a definite time at a high temperature of 40° C. or above. Specific examples of a labile selenium compound which can be used include those described in JP-B-44-15748, JP-B-43-13489, JP-A-4-25832, JP-A-4-109240, and JP-A-4-324855. In particular, the compounds represented by formulae (VIII) and (IX) in JP-A-324855 are preferably used.

The tellurium sensitizers for use in the present invention are compounds capable of producing silver telluride, which is presumed to become sensitization nuclei, on the surface or inside of the silver halide grains. The production speed of silver telluride in a silver halide emulsion can be examined using the method described in JP-A-5-313284.

Specific examples of such a compound as mentioned above include the compounds described in U.S. Pat. Nos. 1,623,499, 3,320,069 and 3,772,031, British Patents 235, 211, 1,121,496, 1,295,462 and 1,396,696, Canadian Patent 800,958, JP-A-4-204640, JP-A-4-271341, JP-A-4-333043, JP-A-5-303157, Journal of Chemical Society Chemical Communication, 635 (1980), ibid., 1102 (1979), ibid., 645 (1979), Journal of Chemical Society Perkin Transaction, 1, 2191 (1980), and *The Chemistry of Organic Selenium and Tellurium Compounds*, compiled by S. Patai, volume 1 (1986) and volume 2 (1987). In particular, the compounds represented by formulae (II), (III) and (IV) in JP-A-5-313284 are preferred.

The suitable amounts of selenium and tellurium sensitizers for use in the present invention depend on the silver halide grains used, chemical ripening conditions and so on. In general, however, they are of the order of $10^{-8}$ to $10^{-2}$ mole, preferably $10^{-7}$ to $10^{-3}$ mole, per mole of silver halide. Although the present invention has no particular restriction as to conditions of chemical sensitization, the pH is preferably from 5 to 8, the pAg is preferably from 6 to 11, more preferably from 7 to 11, and the temperature ranges preferably from 40° to 95° C., more preferably from 45° to 85° C.

As for the precious metal sensitization, gold, platinum, palladium or iridium sensitization can be employed in the present invention. In particular, gold sensitization is preferred. Specific examples of a gold sensitizer used therein include chloroauric acid, potassium chloroaurate, potassium aurithiocyanate and gold sulfide. Such a gold sensitizer can be used in an amount of from $10^{-7}$ to $10^{-2}$ mole per mole of silver halide.

In a process of producing silver halide grains or allowing the produced silver halide grains to ripen physically, a cadmium salt, a zinc salt, a lead salt, a thallium salt and/or the like may be present in the silver halide emulsions used in the present invention.

Also, reduction sensitization can be employed in the present invention. Suitable examples of a reducing sensitizer which can be used include stannous salts, amines, formamidine sulfinic acid and silane compounds.

To the silver halide emulsions for use in the present invention, thiosulfonic compounds may be added using the method described in EP-A-0293917.

The silver halide emulsions in the photographic photosensitive material for use in the present invention may be the same as one another, or two or more different kinds of emulsions (e.g., emulsions differing in average grain size, halide composition, crystal form or condition of chemical sensitization) may be used in combination.

The silver halide emulsions especially suitable for a photosensitive material for dot to dot work according to the present invention are silver chlorobromide or chloroiodobromide emulsions having a silver chloride content of at least 90 mole % and a silver bromide content of from 0 to 10 mole %, preferably those having a chloride content of at least 95 mole %. Emulsions in which silver bromide or iodide is present in a higher proportion are undesirable, because the safelight safety thereof in an illuminated room is unsatisfactory and their gamma values are low.

Further, it is desirable for the silver halide emulsions useful for the present photosensitive material for dot to dot work to contain transition metal complexes. Examples of the transition metals include Rh, Ru, Re, Os, Ir and Cr.

Examples of ligands which can constitute those complexes include nitrosyl and thionitrosyl bridging ligands, halide ligands (fluoride, chloride, bromide and iodide), a cyanide ligand, a cyanate ligand, a thiocyanate ligand, a selenocyanate ligand, a tellurocyanate ligand, an azide ligand and an aquo ligand. When an aquo ligand is present in such a complex as described above, the number of aquo ligand(s) in the complex is preferably 1 or 2.

Suitable examples of transition metal complexes as mentioned above include:

1. $[RU(NO)Cl_5]^{-2}$
2. $[Ru(NO)_2Cl_4]^{-1}$
3. $[Ru(NO)(H_2O)Cl_4]^{-1}$
4. $[Rh(NO)Cl_5]^{-2}$
5. $[Re(NO)CN_5]^{-2}$
6. $[Re(NO)ClCN_4]^{-2}$
7. $[Rh(NO)_2Cl_4]^{-1}$
8. $[Rh(NO)(H_2O)Cl_4]^{-1}$
9. $[Ru(NO)CN_5]^{-2}$
10. $[Ru(NO)Br_5]^{-2}$
11. $[Rh(NS)Cl_5]^{-2}$
12. $[Os(NO)Cl_5]^{-2}$
13. $[Cr(NO)Cl_5]^{-3}$
14. $[Re(NO)Cl_5]^{-1}$
15. $[Os(NS)Cl_4(TeCN)]^{-2}$
16. $[Ru(NS)I_5]^{-2}$
17. $[Re(NS)Cl_4(SeCN)]^{-2}$
18. $[Os(NS)Cl(SCN)_4]^{-2}$
19. $[Ir(NO)Cl_5]^{-2}$

On the other hand, rhodium can be added in the form of any salt, e.g., complex salt, during the preparation of emulsion grains.

Suitable examples of a rhodium salt include rhodium monochloride, rhodium dichloride, rhodium trichloride and ammonium hexachlororhodate. In particular, water-soluble complex compounds of trivalent rhodium and halides, such as hydrogen hexachlororhodate(III) and the salts thereof (ammonium salt, sodium salt, potassium salt) are used to advantage.

Those water-soluble rhodium salts are added in an amount ranging from $1.0\times10^{-6}$ mole to $1.0\times10^{31\ 3}$ mole, preferably from $1.0\times10^{-5}$ mole to $1.0\times10^{-3}$ mole, particularly preferably from $5.0\times10^{-5}$ mole to $5.0\times10^{-4}$ mole, per mole of silver halide.

As for the spectral sensitizing dyes for use in the present invention, they have no particular restrictions.

The amount of sensitizing dyes added depends, e.g., on the crystal form and the size of silver halide grains. In general, however, sensitizing dyes are used in an amount ranging from $4\times10^{-6}$ to $8\times10^{-3}$ mole per mole of silver halide. For instance, in cases where the sizes of silver halide grains are within the range of 0.2 to 1.3 μm, the amount of sensitizing dyes added is preferably within the range of $2\times10^{-7}$ to $3.5\times10^{-6}$ mole, particularly $6.5\times10^{-7}$ to $2.0\times10^{-6}$ mole, per m$^2$ of surface area of silver halide grains.

The light-sensitive silver halide emulsions for use in the present invention may be spectrally sensitized to blue light of relatively long wavelengths, green light, red light or infrared light by the use of sensitizing dyes. Suitable spectral sensitizing dyes which can be employed include cyanine dyes, merocyanine dyes, complex cyanine dyes, complex merocyanine dyes, holopolar cyanine dyes, styryl dyes, hemicyanine dyes, oxonol dyes and hemioxonol dyes.

Sensitizing dyes which can be advantageously used in the present invention are described, e.g., in *Research Disclosure*, No. 17643, Item IV-A (p. 23, December, 1978), ibid., No. 18431, Item X (p. 437, August, 1979), and the references cited therein. In particular, it is of advantage to the present invention to select therefrom sensitizing dyes having spectral sensitivities appropriate to the spectral characteristics of various scanner light sources.

For instance, A) for an argon laser light source, it is favorable to select the simple merocyanines described in JP-A-60-162247, JP-A-02-48653, U.S. Pat. No. 2,161,331, West German Patent 936,071 and JP-A-5-11389; B) for a helium-neon laser light source, it is favorable to select the trinuclear cyanine dyes described in JP-A-50-62425, JP-A-54-18726 and JP-A-59-102229; C) for an LED light source and a red semiconductor laser, it is favorable to select the thiacarbocyanines described in JP-B-48-42172, JP-B-51-9609, JP-B-55-39818, JP-A-62-284343 and JP-A-02-105135; and D) for an infrared semiconductor laser light source, it is favorable to select the tricarbocyanines described in JP-A-59-191032 and JP-A-60-80841 and the 4-quinoline nucleus-containing dicarbocyanines described in JP-A-59-192242 and JP-A-03-67242 (those represented by formulae (IIIa) and (IIIb)).

Those sensitizing dyes may be employed individually or in combination. Combinations of sensitizing dyes are often employed for the purpose of supersensitization. Materials which can exhibit a supersensitizing effect in a combination with a certain sensitizing dye although they themselves do not spectrally sensitize silver halide emulsions or do not substantially absorb light in the visible region may be incorporated in the silver halide emulsions.

Useful sensitizing dyes, supersensitizing combinations of dyes and materials exhibiting a supersensitizing effect are described in *Research Disclosure*, Vol. 176, No. 17643, p. 23, Item IV-J (December, 1978).

For an argon laser light source, Compounds (I)-1 to (I)-8 described in JP-A-60-162247, Compounds I-1 to I-28 described in JP-A-2-48653, Compounds I-1 to I-13 described in JP-A-4-330434, the compounds of Examples 1 to 14 described in U.S. Pat. No. 2,161,331 and Compounds 1 to 7 described in West German Patent 936,071 are useful.

For a helium-neon laser light source, Compounds I-1 to I-38 described in JP-A-54-18726, Compounds I-1 to I-35 described in JP-A-6-75322 and Compounds I-1 to I-34 described in JP-A-7-287338 are useful.

For an LED light source and a red semiconductor laser, Dyes 1 to 20 described in JP-B-55-39818, Compounds I-1 to I-37 described in JP-A-62-284343 and Compounds I-1 to I-34 described in JP-A-7-287338 are useful.

For an infrared semiconductor laser light source, Compounds I-1 to I-12 described in JP-A-59-191032, Compounds I-1 to I-22 described in JP-A-60-80841, Compounds I-1 to I-29 described in JP-A-4-335342 and Compounds I-1 to I-18 described in LTP-A-59-192242 are useful.

For a white light source, e.g., a tungsten light source and a xenon light source for a plate making camera, Compound (1) to (19) represented by formula (I) described in JP-A-55-45015, Compounds 4-A to 4-S, 5-A to 5-Q and 6-A to 6-T described in JP-A-6-242547 are useful.

The developer used for development-processing of the present photosensitive material can contain generally used additives (e.g., a developing agent, an alkali agent, a pH buffer, a preservative, a chelating agent). The photographic processing of the present photosensitive material can be performed using any of known methods, and any of known processing solutions can be used therein.

The developer for use in the present invention has no particular restriction as to a developing agent contained therein. However, it is preferable for the developing agent to comprise a dihydroxybenzene or an ascorbic acid derivative. From the viewpoint of high developing capacity, the combined use of a dihydroxybenzene and a 1-phenyl-3-pyrazolidone, that of a dihydroxybenzene and a p-aminophenol, that of an ascorbic acid derivative and a 1-phenyl-3-pyrazolidone or that of an ascorbic acid derivative and a p-aminophenol is preferred as the developing agent used in the present invention.

Examples of a dihydroxybenzene developing agent suitable for the present invention include hydroquinone, chlorohydroquinone, isopropylhydroquinone, methylhydroquinone and hydroquinone monosulfonate. In particular, hydroquinone is preferred.

Examples of an ascorbic acid derivative developing agent suitable for the present invention include ascorbic acid, the steric isomer thereof, namely erythorbic acid, and the alkali metal salts thereof (sodium salts and potassium salts).

Examples of the 1-phenyl-3-pyrazolidone developing agent for use in the present invention include 1-phenyl-3-pyrazolidone, 1-phenyl-4,4-dimethyl-3-pyrazolidone and 1-phenyl-4-methyl-4-hydroxymethyl-3-pyrazolidone.

Examples of-the p-aminophenol developing agent for use in the present invention include N-methyl-p-aminophenol, p-aminophenol, N-(β-hydroxyethyl)-p-aminophenol and N-(4-hydroxyphenyl) glycine. Of these, N-methyl-p-aminophenol is particularly preferred.

In general, the dihydroxybenzene developing agent is used preferably in an amount of from 0.05 to 0.8 mole/l, particularly preferably 0.2 to 0.6 mole/l. When the combination of a dihydroxybenzene with a 1-phenyl-3-pyrazolidone or p-aminophenol is used, the former is used preferably in an amount of from 0.05 to 0.6 mole/l, more preferably from 0.2 to 0.5 mole/l, and the latter is used preferably in an amount of not greater than 0.06 mole/l, more preferably not greater than 0.03 mole/l.

The suitable amount of an ascorbic acid derivative developing agent used is generally preferably from 0.05 to 0.8 mole/l, particularly preferably 0.2 to 0.6 mole/l. When the combination of an ascorbic acid derivative with a 1-phenyl-3-pyrazolidone or p-aminophenol is used, the former is used preferably in an amount of from 0.05 to 0.6 mole/l, more preferably from 0.2 to 0.5 mole/l, and the latter is used preferably in an amount of not greater than 0.06 mole/l, more preferably not greater than 0.03 mole/l.

Examples of a preservative suitable for the present invention include sodium sulfite, potassium sulfite, lithium sulfite, ammonium sulfite, sodium bisulfite, potassium metabisulfite and sodium formaldehyde bisulfite. These preservatives are used in an amount of not smaller than 0.20 mole/l, particularly preferably not smaller than 0.3 mole/l. However, the addition thereof in a too large amount causes silver stain in the developer. Therefore, the upper limit thereof is preferably 1.2 mole/l, and the particularly preferred amount of the preservative added is from 0.35 to 0.7 mole/l.

As the preservative for a dihydroxybenzene developing agent, a small amount of ascorbic acid derivative may be used in combination with a sulfite. Suitable examples of such an ascorbic acid derivative include ascorbic acid, erythorbic acid, which the steric isomer of ascorbic acid, and alkali metal salts of these acids (sodium and potassium salts). Among these, sodium erythorbate is particularly preferred with respect to the material cost. The proportion of an ascorbic acid derivative as a preservative to a dihydroxybenzene developing agent is preferably in the range of $3/100$ to $12/100$ by mole, particularly preferably $5/100$ to $10/100$ by mole. When an ascorbic acid derivative is used as a preservative, it is preferable that no boron compound be present in the developer.

As an alkali agent for pH adjustment, a water-soluble inorganic alkali metal salt (e.g., sodium hydroxide, potassium hydroxide, sodium carbonate, potassium carbonate) can be generally used. The pH of the developer is preferably from 9.0 to 12.0. More preferably, the developer is adjusted to pH 9.0–11.0, thereby building a stable processing system.

In addition to the aforementioned additives, the developer may contain a development inhibitor, such as sodium bromide or potassium bromide; an organic solvent, such as ethylene glycol, diethylene glycol, triethylene glycol or dimethylformamide; a development accelerator, such as an alkanol amine (e.g., diethanolamine, triethanolamine), imidazole or a derivative thereof; and an antifoggant or a black pepper inhibitor, such as a mercapto compound, an indazole compound, a benzotriazole compound or a bezimidazole compound. Specific examples of such an antifoggant include 5-nitroindazole, 5-p-nitrobenzoylaminoindazole, 1-methyl-5-nitroindazole, 6-nitroindazole, 3-methyl-5-nitroindazole, 5-nitrobenzimidazole, 2-isopropyl-5-nitrobenzimidazole, 5-nitrobenzotriazole, sodium 4-[(2-mercapto-1,3,4-thiadiazole-2-yl)thio]butanesulfonate, 5-amino-1,3,4-thiadiazole-2-thiol, methylbenzotriazole, 5-methylbenzotriazole and 2-mercaptobenzotriazole. These antifoggants are generally used in an amount of 0.01 to 10 mmol, preferably 0.1 to 2 mmol, per liter of the developer.

To the developer for use in the present invention, various kinds of organic and inorganic chelating agents can be added. Examples of the inorganic chelating agents include sodium tetrapolyphosphate and sodium hexametaphosphate.

Examples of the organic chelating agents, on the other hand, include an organic carboxylic acid, an aminopolycarboxylic acid, an organic phosphonic acid, an aminophosphonic acid and an organic phosphonocarboxylic acid.

Specific examples of an organic carboxylic acid include acrylic acid, oxalic acid, malonic acid, succinic acid, glutaric acid, adipic acid, pimelic acid, azelaic acid, sebacic acid, nonanedicarboxylic acid, decanedicarboxylic acid, undecanedicarboxylic acid, maleic acid, itaconic acid, malic acid, citric acid and tartaric acid. However, the organic carboxylic acids usable in the invention should not be construed as being limited to those examples.

Specific examples of an aminopolycarboxylic acid include iminodiacetic acid, nitrilotriacetic acid, nitrilotripropionic acid, ethylenediaminemonohydroxyethyltriacetic acid, ethylenediaminetetraacetic acid, glycolethertetraacetic acid, 1,2-diaminopropanetetraacetic acid, diethylenetriamine-pentaacetic acid, triethylenetetraminehexaacetic acid, 1,3-diamino-2-propanoltetraacetic acid, glycoletherdiaminetetra-acetic acid and the compounds described in JP-A-52-25632, JP-A-55-67747, JP-A-57-102624 and JP-B-53-40900.

Specific examples of an organic phosphonic acid include the hydroxyalkylidenediphosphonic acids described, e.g., in U.S. Pat. Nos. 3,214,454 and 3,794,591, and West German Patent (OLS) 2,227,639, and the compounds described in Research Disclosure, Vol. 181, No. 18170 (May, 1979).

Examples of the aminophosphonic acid include aminotris (methylenesulfonic acid), ethylenediaminetetramethylenephosphonic acid and aminotrimethylenephosphonic acid. In addition, the compounds described in Research Disclosure, No. 18170, JP-A-57-208554, JP-A-54-61125, JP-A-55-29883 and JP-A-56-97347 can also be examples thereof.

Examples of an organic phosphonocarboxylic acid include the compounds described in JP-A-52-102726, JP-A-53-42730, JP-A-54-121127, JP-A-55-4024, JP-A-55-4025, JP-A-55-126241, JP-A-55-65955, JP-A-55-65956 and Research Disclosure, No. 18170.

The above-recited chelating agents may be used in the form of alkali metal salt or ammonium salt. The amount of those chelating agents added is preferably from $1\times10^{-4}$ to $1\times10^{-1}$ mole, more preferably from $1\times10^{-3}$ to $1\times10^{-2}$ mole, per liter of the developer.

Further, the compounds described in JP-A-56-24347, JP-B-56-46585, JP-B-62-2849 and JP-A-04-362942 can be used as silver stain inhibitor in the developer.

In addition, the compounds described in JP-A-62-212651 can be used as uneven development inhibitor, and the compounds described in JP-A-61-267759 can be used as dissolution aids.

Furthermore, the developer may contain a toning agent, a surfactant, a defoaming agent, a hardener and so on, if desired.

Examples of buffers suitable for the developer for use in the present invention include carbonates, boric acid described in JP-A-62-186259, the sugars described in JP-A-60-93433 (e.g., saccharose), oximes (e.g., acetoxime), phenols (e.g., 5-sulfosalicylic acid) and tertiary phosphates (e.g., the sodium and potassium thereof). Preferably, a carbonate and boric acid are used as buffers.

The temperature and the time of development-processing correlate with each other, and they are determined depending on the total processing time. In general, the development temperature is from about 20° C. to about 50° C., preferably from 25° C. to 45° C.; while the development time is from 5 seconds to 2 minutes, preferably 7 seconds to 1.5 minutes.

In the development-processing of 1 m² of silver halide black-and-white photographic photosensitive material, the volume of a replenisher used is controlled to 500 ml or less, preferably 400 ml or less.

For the purposes of reducing the costs of packing and conveying processing solutions, and economizing in space, it is advantageous to prepare concentrated processing solutions and to dilute them when they are used. In concentrating a developer, it is effective to convert in advance the salt-form constituents of the developer into potassium salts.

The fixer used in the fixation step of the present invention is an aqueous solution containing sodium thiosulfate or ammonium thiosulfate, and optionally tartaric acid, citric acid, gluconic acid, boric acid, iminodiacetic acid, 5-sulfosalicylic acid, glucoheptanoic acid, Tiron, ethylenediaminetetraacetic acid, diethylenetriaminepentaacetic acid, nitrilotriacetic acid or/and salts thereof. From the recent viewpoint of environmental conservation, it is preferable for the fixer to be free from boric acid.

The fixing agent for the fixer used in the present invention is sodium thiosulfate, ammonium thiosulfate or the like. Although ammonium thiosulfate is preferred with respect to the fixing speed, sodium thiosulfate may be used from the recent viewpoint of environmental conservation. Such a known fixing agent can be used in a proper amount. In general, the amount used is from about 0.1 to about 2 mole/l, particularly preferably from 0.2 to 1.5 mole/l.

The fixer may optionally contain a hardener (e.g., a water-soluble aluminum compound), a preservative (e.g., a sulfite, a bisulfite), a pH buffer (e.g., acetic acid), a pH modifier (e.g., ammonia, sulfuric acid), a chelating agent, a surfactant, a wetting agent and a fixation accelerator.

Examples of the surfactant include anionic surfactants such as sulfated compounds and sulfonated compounds, polyethylene surfactants and the amphoteric surfactants described in JP-A-57-6740. Also, known defoaming agents may be added. Examples of the wetting agent include alkanolamines and alkylene glycols. Examples of the fixation accelerator include the thiourea derivatives described, e.g., in JP-B-45-35754, JP-A-58-122535 and JP-B-58-122536, alcohols having a triple bond in the molecule, the thioether compounds described in U.S. Pat. No. 4,126,459 and the meso ion compounds described in JP-A-04-229860. In addition, the compounds described in JP-A-02-44355 may be used as the fixation accelerator.

Examples of a pH buffer suitable for the fixer include organic acids, such as acetic acid, malic acid, succinic acid, tartaric acid, citric acid, oxalic acid, maleic acid, glycolic acid and adipic acid, and inorganic pH buffers, such as boric acid, phosphates and sulfites. Preferably, acetic acid, tartaric acid and sulfites are used as pH buffers.

These pH buffers are used for the purpose of protecting the pH of the fixer from rising by the developer brought into the fixer, and the amount of pH buffers used is preferably 0.01–1.0 mole/l, more preferably 0.02–0.6 mole/l.

In addition, the compounds described in JP-A-64-4739 can be used as dye elution accelerator.

The hardener in the fixer of the present invention includes water-soluble aluminum salts and chromium salts. However, preferred hardeners are water-soluble aluminum salts. Specific examples thereof include aluminum chloride, aluminum sulfate and potassium alum. The suitable amount of a hardener added is preferably from 0.01 to 0.2 mole/l, more preferably from 0.03 to 0.08 mole/l.

The fixation temperature ranges from about 20° C. to about 50° C., preferably from 25° C. to 45° C., and the fixation time is from 5 seconds to 1 minute, preferably from 7 seconds to 50 seconds.

The volume of a replenisher for the fixer is 600 ml or below, particularly preferably 500 ml or below, per m² of photosensitive material processed by the fixer.

The photosensitive material which has undergone development and subsequent fixation processing is subjected to washing or stabilization processing.

The wash or stabilization processing is generally carried out using washing water in a volume of 20 liter or less per m² of silver halide photosensitive material, or it may also be performed using a replenisher in a volume of 3 liter or less (including 0 liter, namely washing in reserved water) per m² of silver halide photosensitive material. In other words, a saving of water in the processing becomes possible and, what is more, the pipe arrangement upon installation of an automatic processor can be made unnecessary.

As a method of reducing a replenishment rate of washing water, a multistage counter current method (e.g., two-stage, three-stage) has been known for long. When this multistage counter current method is adopted in the present invention, the photosensitive material after fixation is processed gradually in a normal direction, that is, processed as it is brought into contact successively with processing solutions which are arranged in an ascending order of less contamination with a fixer, thereby improving the efficiency of washing.

For the purpose of achieving the washing in a small amount of water, it is preferable to employ washing tanks equipped with squeegee rollers and crossover rollers described, e.g., in JP-A-63-18350 and JP-A-62-28725. As another measure to solve a problem arising from the washing with a small amount of water, namely to reduce pollution loads, the washing may be carried out in combination with the addition of various oxidizing agents and filtration.

Further, as described in JP-A-60-235133, a part or all of the overflow of a washing or stabilizing bath, which is generated by replenishing the bath with antimold means-taken water according to the progress of the processing, can be employed in the prior processing step, in other words, for a processing solution having fixability.

To the washing bath, a water-soluble surfactant and a defoaming agent may also be added in order to prevent generation of water form unevenness and/or adhesion of processing chemicals to squeegee rollers from transferring onto the films processed since these troubles tend to occur upon washing with a small amount of water.

In addition, the dye adsorbent described in JP-A-63-163456 may be placed in a washing tank for the purpose of preventing the contamination with dyes eluted from the photosensitive material.

Subsequently to the washing processing, stabilization processing may also be carried out. For instance, the baths containing the compounds described in JP-A-02-201357, JP-A-02-132435, JP-A-01-102553 and JP-A-46-44446 may be used as the final bath for the photosensitive material.

To such a stabilizing bath also, various additives, including an ammonium compound, a metal compound containing Bi, Al or the like, a brightening agent, various chelating agents, film pH modifier, a hardener, a bactericide, an antimold, an alkanolamine and a surfactant, can be added, if desired. As the water used in the washing or stabilization processing step, not only service water but also deionized water or the water sterilized with halogen, an ultraviolet sterilizer lamp, an oxidizing agent (e.g., ozone, hydrogen peroxide, chlorate) or so on may be preferably used. In addition, the washing water containing the compounds described in JP-A-04-39652 and JP-A-05-241309 may be employed.

The suitable temperature and time for washing or stabilization processing are from 0 to 50° C. and from 5 seconds to 2 minutes, respectively.

The processing solutions for use in the present invention are preferably stored using the packing material described in JP-A-61-73147, which is slightly pervious to oxygen.

The processing solutions for use in the present invention may be powdered or solidified. For this purpose, the methods described in JP-A-61-259921, JP-A-04-85533 and JP-A-04-16841 are favorable, although any of known methods can be employed. In particular, the method described in JP-A-61-259921 is preferred over the others.

In a case where the replenishment rate is reduced, it is preferable for the processing solution to be prevented from evaporating and undergoing aerial oxidation by diminishing the area open to the air in the processing tank. U.S. Pat. Nos. 3,025,779 and 3,545,971 disclose the roller conveyance type automatic developing machine. In the present invention, such a developing machine is simply referred to as a roller auto processor. The roller auto processor is constructed of development, fixation, washing and drying sections. In the photographin processing of the present photosensitive material, it is most desirable to follow the process constituted of those four steps, although other steps (e.g., a stop step) are not excluded therefrom. It doesn't matter if the washing step is replaced by a stabilizing step in the photographic processing employed in the present invention.

The present hydrazine nucleating agent can also be applied to the method of forming a direct positive image by subjecting an internal latent-image type silver halide photographic emulsion to surface development in the presence of a nucleating agent, and to the photographic emulsions or photosensitive materials used for the aforesaid method (e.g., those described in U.S. Pat. Nos. 2,456,953, 2,497,875, 2,497,876, 2,588,982, 2,592,250, 2,675,318, 3,227,552 and 3,317,322, British Patents 1,011,062, 1,151,363, 1,269,640 and 2,011,391, JP-B-43-29405, JP-B-49-38164, JP-A-53-16623, JP-A-53-137133, JP-A-54-37732, JP-A-54-40629, JP-A-54-74536, JP-A-54-74729, JP-A-55-52055 and JP-A-55-90940).

In the foregoing method of forming a direct positive image, the nucleating agent may be added to a developing solution, but it is rather general to incorporate the nucleating agent in a photographic emulsion layer or another appropriate layer of the photosensitive material.

The present photosensitive material has no particular restrictions as to additives and a photographic processing method applied thereto. For instance, those described in the following references can be employed to advantage.

| Items | References |
|---|---|
| 1) Surfactants | JP-A-02-12236 (p. 9, from 7th line on right upper column to 7th line on right lower column), and JP-A-02-18542 (p. 2, from 13th line on left lower column to p. 4, 18th line on right lower column). |
| 2) Antifoggants | JP-A-02-103536 (from p. 17, 19th line on right lower column, to p. 18, 4th line on right upper column, and p. 18, from 1st line to 5th line on right lower column), and JP-A-01-237538 (thiosulfinic acid compounds). |
| 3) Polymer latexes | JP-A-02-103536 (p. 18, left lower column, lines 12–20). |
| 4) Acid group containing compounds | JP-A-02-103536 (from p. 18, 6th line on right lower column, to p. 19, 1st line on left upper column). |
| 5) Matting agents, lubricants and plasticizers | JP-A-02-103536 (p. 19, from 15th line on left upper column to 15th line on right upper column). |
| 6) Hardeners | JP-A-02-103536 (p. 18, right upper column, lines 5–17). |
| 7) Dyes | Dyes described in JP-A-02-103536, p. 17, right lower column, lines 1–18, and Solid dyes described in JP-A-02-294638 and JP-A-5-11382. |
| 8) Binders | JP-A-02-18542 (p. 3, right lower column, lines 1–20). |
| 9) Black pepper inhibitors | Compounds described in U.S. Pat. No. 4,956,257 and JP-A-01-118832. |
| 10) Redox compounds | Compounds represented by formula (I) in JP-A-02-301743 (especially Compound Examples 1–50), Compounds represented by formulae (R-1), (R-2) and (R-3), Compounds 1 to 75 in JP-A-03-174143 (pp. 3–20), and Compounds described in JP-A-5-257239. |
| 11) Monomethine compounds | Compounds of formula (II) in JP-A-02-287532 (especially Compound Examples II-1 to II-26). |
| 12) Dihydroxybenzenes | Compounds described in JP-A-03-39948 (p. 11, left upper column, to p. 12, left lower column) and EP-A-0452772. |

The present invention is illustrated in more detail by reference to the following examples. However, the invention should not be construed as being limited to these examples.

EXAMPLE 1

<Preparation of Solid Dispersions of Hydrazide Compounds>

A 25% water solution of Demol SNB (trade name, a product of Kao Corporation) was prepared. Each of the hydrazide compounds set forth in Table 11 in an amount of 0.5 g was admixed with a 0.6 g portion of the foregoing water solution of Demol SNB and 59 of water to prepare a slurry. This slurry was placed in a dispersing machine (1/16 gallon, a sand grinder mill (made by AIMEX Co., Ltd.)), and dispersed for 15 hours using as media glass beads having their diameters in the range of 0.8–1.2 mm. The dispersion thus obtained was admixed with a water solution of gelatin so that the resultant dispersion had a hydrazide compound concentration of 0.5% and a gelatin concentration of 5%, and thereto Proxel as an antiseptic was added in a proportion of 2,000 ppm to gelatin. Finally, the dispersion was adjusted to pH 5.0 by the addition of ascorbic acid. The average grain sizes of the thus prepared solid dispersions of hydrazide compounds are shown in Table 1.

For the comparison with the present hydrazide compounds, the following hydrazide compounds were employed.

Comparative Compound 1-1

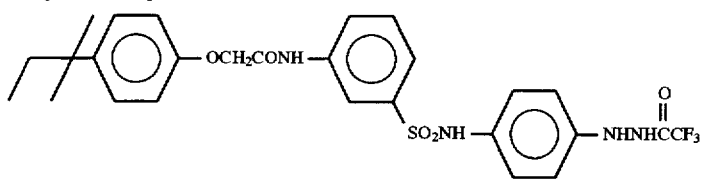

Comparative Compound 1-2

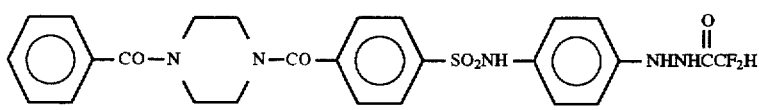

Comparative Compound 1-3

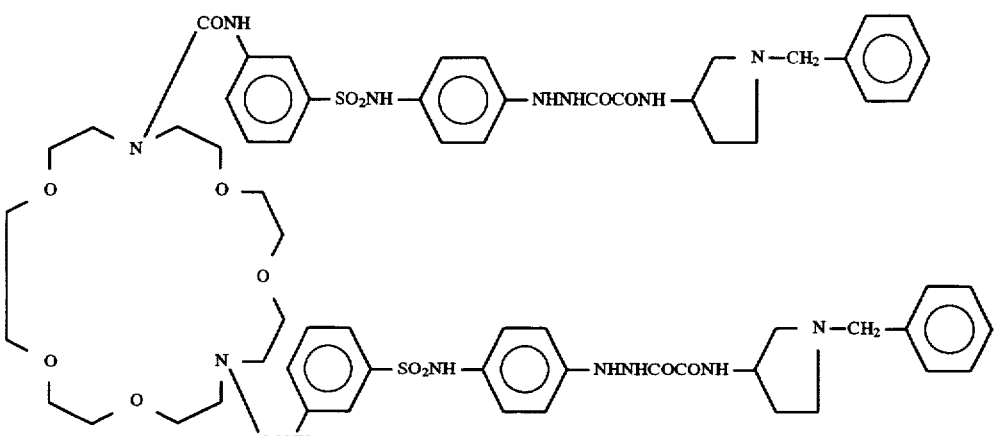

(Compound I-34 described in JP-A-05-127287)

Comparative Compound 1-4

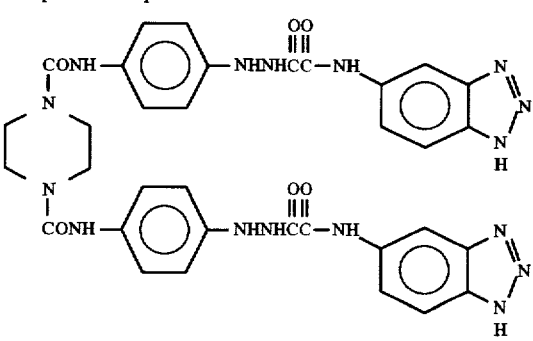

(Compound (3) described in JP-A-04-16938)

Comparative Compound 1-5
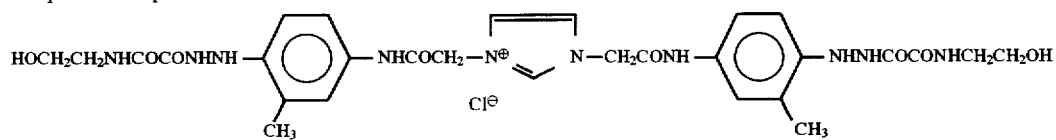
(Compound described in WO 95/32453)
Comparative Compound 1-6
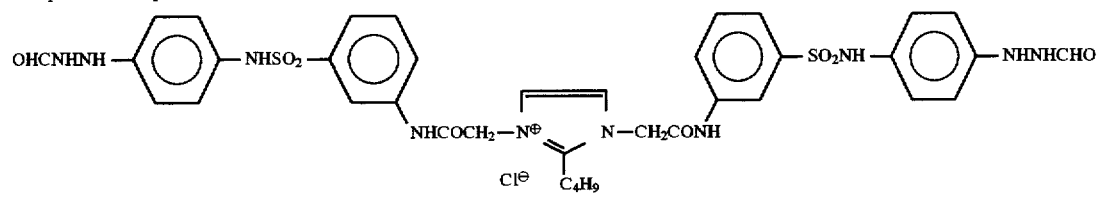
(Compound described in WO 95/32453)
Comparative Compound 1-7
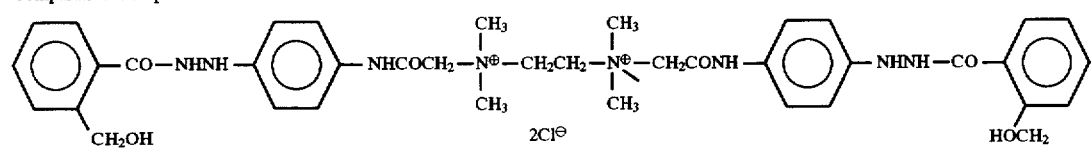
(Compound described in WO 95/32453)
Comparative Compound 2-2
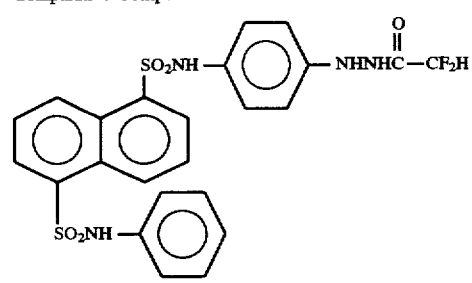
Comparative Compound 2-3
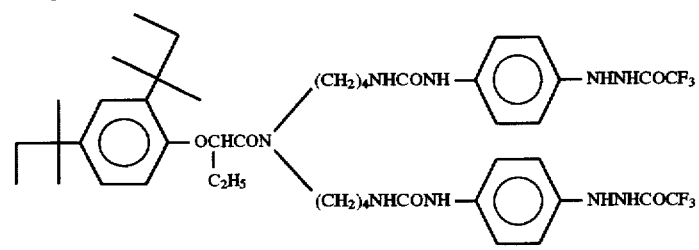
(Compound (ka19) described in JP-A-05-197071)
Comparative Compound 2-4
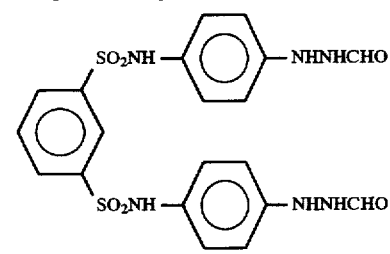
(Compound (ka17) described in JP-A-05-197091)

Comparative Compound 3-2

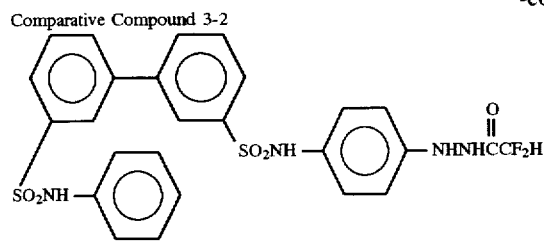

Comparative Compound 3-3

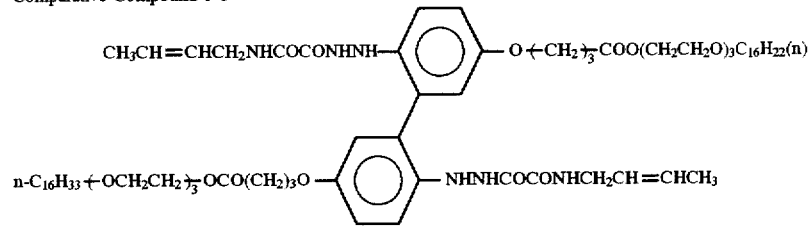

(Compound I-24 described in JP-A-05-127287)

Comparative Compound 3-4

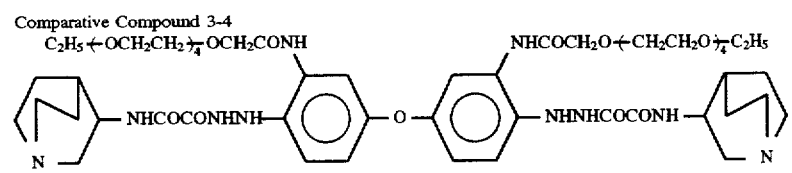

(Compound I-40 described in JP-A-05-127287)

Comparative Compound 3-5

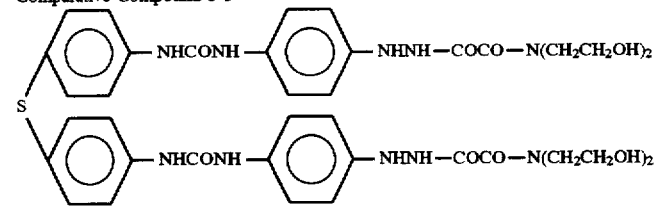

(Compound (4) described in JP-A-04-16938)

TABLE 1

| Solid Dispersion | Hydrazide Compound | Average Grain Size (μm) |
|---|---|---|
| K-1 | Compar. Compound 1-1 | 0.21 |
| K-2 | Compar. Compound 1-2 | 0.40 |
| K-3 | Compar. Compound 1-3 | 0.46 |
| K-4 | Compar. Compound 1-4 | 0.36 |
| K-5 | Compar. Compound 1-5 | 0.38 |
| K-6 | Compar. Compound 1-6 | 0.40 |
| K-7 | Compar. Compound 1-7 | 0.39 |
| K-8 | Compar. Compound 2-2 | 0.44 |
| K-9 | Compar. Compound 2-3 | 0.45 |
| K-10 | Compar. Compound 2-4 | 0.49 |
| K-11 | Compar. Compound 3-2 | 0.39 |
| K-12 | Compar. Compound 3-3 | 0.46 |
| K-13 | Compar. Compound 3-4 | 0.38 |
| K-14 | Compar. Compound 3-5 | 0.47 |
| K-15 | 1-1c | 0.40 |
| K-16 | 1-2c | 0.50 |
| K-17 | 1-3c | 0.39 |
| K-18 | 1-4c | 0.42 |
| K-19 | 1-12c | 0.48 |
| K-20 | 1-13c | 0.43 |
| K-21 | 1-15c | 0.44 |
| K-22 | 1-16c | 0.50 |
| K-23 | 1-17c | 0.39 |
| K-24 | 1-18c | 0.47 |
| K-25 | 1-19c | 0.49 |

TABLE 1-continued

| Solid Dispersion | Hydrazide Compound | Average Grain Size (μm) |
|---|---|---|
| K-26 | 1-31c | 0.41 |
| K-27 | 1-1d | 0.42 |
| K-28 | 1-2d | 0.36 |
| K-29 | 1-3d | 0.50 |
| K-30 | 1-4d | 0.49 |
| K-31 | 1-12d | 0.41 |
| K-32 | 1-13d | 0.42 |
| K-33 | 1-15d | 0.38 |
| K-34 | 1-16d | 0.36 |
| K-35 | 1-17d | 0.40 |
| K-36 | 1-18d | 0.46 |
| K-37 | 1-19d | 0.50 |
| K-38 | 1-31d | 0.40 |
| K-39 | 2-1c | 0.44 |
| K-40 | 2-2c | 0.40 |
| K-41 | 2-3c | 0.39 |
| K-42 | 2-4c | 0.46 |
| K-43 | 2-5c | 0.38 |
| K-44 | 2-6c | 0.44 |
| K-45 | 2-14c | 0.49 |
| K-46 | 2-16c | 0.35 |
| K-47 | 2-18c | 0.40 |
| K-48 | 2-1b | 0.39 |
| K-49 | 2-2b | 0.34 |
| K-50 | 2-3b | 0.50 |

TABLE 1-continued

| Solid Dispersion | Hydrazide Compound | Average Grain Size (μm) |
|---|---|---|
| K-51 | 2-4b | 0.41 |
| K-52 | 2-5b | 0.44 |
| K-53 | 2-6b | 0.48 |
| K-54 | 2-14b | 0.47 |
| K-55 | 2-16b | 0.42 |
| K-56 | 2-18b | 0.41 |
| K-57 | 3-1c | 0.40 |
| K-58 | 3-2c | 0.42 |
| K-59 | 3-3c | 0.50 |
| K-60 | 3-4c | 0.41 |
| K-61 | 3-7c | 0.37 |
| K-62 | 3-9c | 0.50 |
| K-63 | 3-10c | 0.41 |
| K-64 | 3-11c | 0.43 |
| K-65 | 3-12c | 0.40 |
| K-66 | 3-13c | 0.49 |
| K-67 | 3-15c | 0.48 |
| K-68 | 3-18c | 0.46 |
| K-69 | 3-21c | 0.42 |
| K-70 | 3-22c | 0.45 |
| K-71 | 3-1b | 0.35 |
| K-72 | 3-2b | 0.47 |
| K-73 | 3-3b | 0.42 |
| K-74 | 3-4b | 0.43 |
| K-75 | 3-7b | 0.45 |
| K-76 | 3-9b | 0.34 |
| K-77 | 3-10b | 0.50 |
| K-78 | 3-11b | 0.43 |
| K-79 | 3-12b | 0.39 |
| k-80 | 3-13b | 0.40 |
| K-81 | 3-15b | 0.47 |
| K-82 | 3-18b | 0.45 |
| K-83 | 3-21b | 0.46 |
| K-84 | 3-22b | 0.48 |

EXAMPLE 2

<Production of Silver Halide Photosensitive Materials> i) Preparation of Emulsion A

An aqueous silver nitrate solution and an aqueous halide solution containing potassium bromide, sodium chloride, $K_3IrCl_6$ in an amount of $3.5\times10^{-7}$ mole/mole of silver and $K_2Rh(H_2O)Cl_5$ in an amount of $2.0\times10^{-7}$ mole/mole of silver were added to an aqueous gelatin solution containing sodium chloride and 1,3-dimethyl-2-imidazolidinethione with stirring in accordance with a double jet method, thereby preparing silver chlorobromide grains having a silver chloride content of 70 mole % and an average grain size of 0.25 μm.

Then, these grains were washed with water according to a conventional flocculation method, and thereto 40 g of gelatin per mole of silver, 7 mg of sodium benzenethiosulfonate per mole of silver and 2 mg of benzenesulfinic acid per mole of silver were added. The emulsion thus prepared was adjusted to pH 6.0 and pAg 7.5, and chemically sensitized at 60° C. with 2 mg of sodium thiosulfate per mole of silver and 4 mg of chloroauric acid per mole of silver so as to acquire the optimum sensitivity. Thereafter, the resulting emulsion was admixed with 150 mg of 4-hydroxy-6-methyl-1,3,3a,7-tetrazaindene as a stabilizer and 100 mg of Proxel as an antiseptic. The thus obtained emulsion grains were cubic silver chlorobromide grains having an average grains size of 0.25 μm and a silver chloride content of 70 mole % (variation coefficient: 10%).

ii) Production of Coating Samples:

The surface of a polyethylene terephthalate film support was provided with a moistureproofing undercoat containing polyvinylidene chloride, and further coated successively with photographic constituent layers so as to have a layer structure such that UL, EM, PC and OC layers were arranged from the support-side in the order of description, thereby producing a sample.

The way of preparing a coating composition for each layer and the coverage of each layer are described below:

(UL Layer)

A polyethylacrylate dispersion was added to an aqueous gelatin solution so that the proportion of polyethylacrylate to gelatin was 30wt %, and the resultant dispersion was coated at a gelatin coverage of 0.5 g/m².

(EM Layer)

To the above-mentioned Emulsion A were added $5\times10^{-4}$ mole of Compound (S-1) illustrated below per mole of silver and $5\times10^{-4}$ mole/mole silver of Compound (S-2) illustrated below as sensitizing dyes, and further $3\times10^{-4}$ mole/mole silver of mercapto compound shown below as (a), $4\times10^{-4}$ mole/mole silver of mercapto compound shown below as (b), $4\times10^{-4}$ mole/mole silver of triazine compound shown below as (c), $2\times10^{-3}$ mole/mole silver of 5-chloro-8-hydroxyquinoline, $5\times10^{-4}$ mole/mole of a nucleation accelerator shown below as at (A), and $5\times10^{-4}$ mole/mole silver of a surfactant shown below as (p). Thereto were furthermore added hydroquinone and sodium salt of N-oleyl-N-methyltaurine so as to have coverage rates of 100 mg/m² and 30 mg/m², respectively. Then, the resultant emulsion was admixed with $5\times10^{-4}$ mole/mole silver of a nucleating agent, i.e., a hydrazide compound in the form of solid dispersion prepared in Example 1, as it was shown in Table 2. Further, thereto were added 200 mg/m² of a water-soluble latex shown below as (d), 200 mg/m² of a polyethylacrylate dispersion, 200 mg/m² of a methylacrylate/sodium 2-acrylamido-2-methylpropanesulfonate/2-acetacetoxyethylmethacrylate (88/5/7 by weight) terpolymer latex, 200 mg/m² of colloidal silica having an average particle size of 0.02 μm, 200 mg/m² of 1,3-divinylsulfonyl-2-propanol as a hardener, and 30 mg/m² of sodium polystyrenesulfonate as a thickening agent. The thus prepared emulsion was adjusted to pH 5.65 with acetic acid, and applied on the UL layer at a coverage rate of 2.8 g/m², in terms of silver.

(PC Layer)

An polyethylacrylate dispersion was added to an aqueous gelatin solution in a proportion of 50wt % to the gelatin, and thereto were added 5 mg/m² of the following surfactant (w) and 10 mg/m² of 1,5-dihydroxy-2-benzaldoxime. The resultant dispersion was applied at a coverage rate of 0.5 g/m², in terms of gelatin.

(OC Layer)

A coating composition containing 0.5 g/m² of gelatin, 40 mg/m² of amorphous $SiO_2$ having an average particle size of about 3.5 μm as a matting agent, 0.1 g/m² of methanol silica, 100 mg/m² of polyacrylamide, 20 mg/m² of silicone oil and, as coating aids, 5 mg/m² of a fluorine-containing surfactant shown below as (e) and 10 mg/m² of sodium dodecylbenzenesulfonate was applied in a layer.

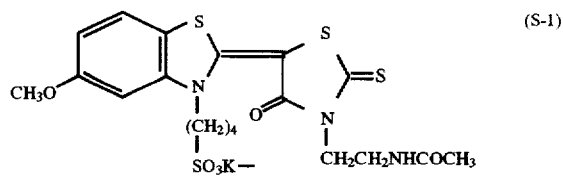

(S-1)

Each of the thus produced coating samples was provided with backing and back protecting layers having the following compositions respectively.

| [Formula of Backing Layer] | |
|---|---|
| Gelatin | 3 g/m² |
| Latex (polyethylacrylate) | 2 g/m² |
| Surfactant (sodium p-dodecylbenzenesulfonate) | 40 mg/m² |
| CH₂=CHSO₂CH₂CONH—(CH₂)₂—NHCOCH₂SO₂CH=CH₂ | 100 mg/m² |
| SnO₂/Sb (90/10 by weight; average grain size of 0.20 μm) | 200 mg/m² |
| Dyes (mixture of Dye [a], Dye [b] and Dye [c]) | |
| Dye [a] | 70 mg/m² |
| Dye [b] | 70 mg/m² |

-continued

Dye [c]      90 mg/m²

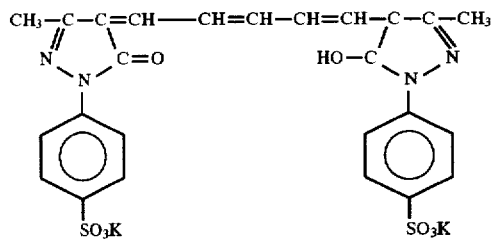

[Formula of Back Protecting Layer]

| | |
|---|---|
| Gelatin | 0.8 g/m² |
| Fine particles of polymethylmethacrylate (average particle size: 4.5 μm) | 30 mg/m² |
| Sodium dihexyl-α-sulfosuccinate | 15 mg/m² |
| Sodium p-dodecylbenzenesulfonate | 15 mg/m² |
| Sodium acetate | 40 mg/m² |

In the above-mentioned manner, samples as shown in Table 2 were produced.

TABLE 2

| Sample No. | Solid Dispersion of Hydrazide Compound | Remark |
|---|---|---|
| 1-1 | K - 1 | comparison |
| 1-2 | K - 2 | comparison |
| 1-3 | K - 3 | comparison |
| 1-4 | K - 4 | comparison |
| 1-5 | K - 5 | comparison |
| 1-6 | K - 6 | comparison |
| 1-7 | K - 7 | comparison |
| 1-8 | K - 8 | comparison |
| 1-9 | K - 9 | comparison |
| 1-10 | K - 10 | comparison |
| 1-11 | K - 11 | comparison |
| 1-12 | K - 12 | comparison |
| 1-13 | K - 13 | comparison |
| 1-14 | K - 14 | comparison |
| 1-15 | K - 15 | invention |
| 1-16 | K - 16 | invention |
| 1-17 | K - 17 | invention |
| 1-18 | K - 18 | invention |
| 1-19 | K - 19 | invention |
| 1-20 | K - 20 | invention |
| 1-21 | K - 21 | invention |
| 1-22 | K - 22 | invention |
| 1-23 | K - 23 | invention |
| 1-24 | K - 24 | invention |
| 1-25 | K - 25 | invention |
| 1-26 | K - 26 | invention |
| 1-27 | K - 48 | invention |
| 1-28 | K - 49 | invention |
| 1-29 | K - 50 | invention |
| 1-30 | K - 51 | invention |
| 1-31 | K - 52 | invention |
| 1-32 | K - 53 | invention |
| 1-33 | K - 54 | invention |
| 1-34 | K - 55 | invention |
| 1-35 | K - 56 | invention |
| 1-36 | K - 71 | invention |
| 1-37 | K - 72 | invention |
| 1-38 | K - 73 | invention |
| 1-39 | K - 74 | invention |
| 1-40 | K - 75 | invention |
| 1-41 | K - 76 | invention |
| 1-42 | K - 77 | invention |
| 1-43 | K - 78 | invention |
| 1-44 | K - 79 | invention |
| 1-45 | K - 80 | invention |
| 1-46 | K - 81 | invention |
| 1-47 | K - 82 | invention |

TABLE 2-continued

| Sample No. | Solid Dispersion of Hydrazide Compound | Remark |
|---|---|---|
| 1-48 | K - 83 | invention |
| 1-49 | K - 84 | invention |

<Preparation of Developer>

A developer having the following composition (Developer A) was prepared.

| Composition of Developer A: | |
|---|---|
| Sodium hydroxide | 1.71 g |
| Diethylenetriaminepentaacetic acid | 4 g |
| Potassium carbonate | 27.5 g |
| Sodium carbonate | 25.5 g |
| Sodium erythorbate | 30 g |
| N-Methyl-p-aminophenol | 7.5 g |
| KBr | 2 g |
| 5-Methylbenzotriazole | 0.1 g |
| 1-Phenyl-5-mercaptotetrazole | 0.02 g |
| Sodium sulfite | 5 g |
| Glacial acetic acid | 9 g |
| Water to make | 1 l |
| pH adjusted to | 9.7 |

In addition, Developer B was prepared by adding acetic acid to Developer A so that the pH was adjusted to 9.4, and Developer C was prepared by adding sodium hydroxide to Developer A so that the pH was adjusted to 10.0.

<Evaluation>

(1) Exposure and Development Processing

Each of the samples produced above was exposed to a xenon flash lamp having an emission time of $10^{-5}$ sec. through a step wedge via an interference filter having a peak at 488 nm, developed for 20 sec. at 35° C. with each of Developers A, B and C, and further subjected to successive fixation, washing and drying operations. Herein, an auto processor, FG-680 AG, made by Fuji Photo Film Co., Ltd., was used. During the photographic processing, the replenisher volumes for each Developer and a fixer were controlled to 100 ml and 150 ml respectively per m² of sample.

The fixer used therein was Fixer A having the following composition.

| Composition of Fixer A: | |
|---|---|
| Ammonium thiosulfate | 119.7 g |
| Disodium ethylenediaminetetraacetate dihydrate | 0.03 g |
| Sodium thiosulfate pentahydrate | 10.9 g |
| Sodium sulfite | 25.0 g |
| NaOH (neat) | 12.4 g |
| Glacial acetic acid | 29.1 g |
| Tartaric acid | 2.92 g |
| Sodium gluconate | 1.74 g |
| Aluminum sulfate | 8.4 g |
| pH (adjusted with sulfuric acid or sodium hydroxide) | 4.8 |
| Water to make | 1 l |

(2) High contrast characteristics

High contrast characteristics under development with Developer A were expressed as follows: As for the indication of image contrast (i.e., gamma), the inclination of a straight line connecting two points on a characteristic curve corresponding to the optical density of fog+0.1 and the optical density of fog+3.0 was defined as the value of gamma. That is, the gamma is represented by the relation, $\gamma=|3.0-0.1|/|\log(\text{the amount of exposure providing the optical density } 3.0)-\log(\text{the amount of exposure providing the optical density } 0.1)|$, and the greater the gamma value, the more contrasty the photographic characteristics.

(3) Sensitivity

The sensitivity was expressed in terms of the reciprocal of the amount of exposure providing the optical density of 1.5, and the sensitivity value of each sample was calculated as the relative value, with a standard sample being taken as 100. Accordingly, the greater the value obtained, the higher the sensitivity.

(4) Dependence of Sensitivity on pH of Developer

The dependence of sensitivity on pH of the developer was estimated by the following equation using the sensitivity values obtained under development with Developers B and C respectively;

pH dependence of sensitivity $(\Delta S_{1.5})=S_{1.5}$ (Developer C)$-S_{1.5}$ (Developer B)

Accordingly, the smaller the value obtained, the less the dependence of sensitivity on pH of the developer, in other words, the higher the processing consistency.

(5) Aging Stability of Sensitive Material

Each sample was stored for 3 days under the condition of 60° C.–65% RH, subjected to the same exposure and photographic processing operations as described hereinbefore, except that the development was carried out using Developer A alone, and then examined for the sensitivity. Separately, each sample was stored for 3 days at ordinary temperature and humidity, and then subjected to the sensitivity evaluation in the same manner as mentioned above. The variation in sensitivity due to aging was defined by a sensitivity difference between these two cases. Namely, it is represented by the following equation;

Variation in sensitivity due to aging $(\Delta S_{1.5})=S_{1.5}$ (sample stored for 3 days under 60° C.–65% RH)$-S_{1.5}$ (sample stored for 3 days at ordinary temperature and humidity).

Accordingly, the value nearer to 0 signifies that the sensitive material examined has the higher aging stability.

The results obtained are shown in Table 3.

TABLE 3

| Sample No. | Gamma value | pH Dependence of developer $(\Delta S_{1.5})$ | Aging stability of sensitive material $(\Delta S_{1.5})$ | Remark |
|---|---|---|---|---|
| 1-1  | 13 | 0.21 | −0.02 | comparison |
| 1-2  | 14 | 0.26 | −0.14 | comparison |
| 1-3  | 11 | 0.14 | −0.08 | comparison |
| 1-4  | 12 | 0.15 | −0.06 | comparison |
| 1-5  | 13 | 0.15 | −0.07 | comparison |
| 1-6  | 14 | 0.14 | −0.06 | comparison |
| 1-7  | 14 | 0.17 | −0.09 | comparison |
| 1-8  | 14 | 0.24 | −0.15 | comparison |
| 1-9  | 15 | 0.15 | −0.07 | comparison |
| 1-10 | 12 | 0.25 | −0.04 | comparison |
| 1-11 | 11 | 0.24 | −0.15 | comparison |
| 1-12 | 14 | 0.12 | −0.05 | comparison |
| 1-13 | 15 | 0.14 | −0.08 | comparison |
| 1-14 | 15 | 0.15 | −0.06 | comparison |
| 1-15 | 19 | 0.06 | −0.01 | invention |
| 1-16 | 19 | 0.06 | −0.01 | invention |
| 1-17 | 18 | 0.07 | −0.01 | invention |
| 1-18 | 16 | 0.09 | −0.02 | invention |
| 1-19 | 17 | 0.06 | −0.01 | invention |
| 1-20 | 17 | 0.08 | −0.02 | invention |
| 1-21 | 17 | 0.08 | −0.02 | invention |
| 1-22 | 19 | 0.08 | −0.02 | invention |
| 1-23 | 18 | 0.06 | −0.02 | invention |
| 1-24 | 16 | 0.09 | −0.01 | invention |
| 1-25 | 16 | 0.07 | −0.02 | invention |
| 1-26 | 19 | 0.06 | −0.01 | invention |
| 1-27 | 19 | 0.01 | −0.03 | invention |
| 1-28 | 22 | 0    | −0.03 | invention |
| 1-29 | 21 | 0.01 | −0.04 | invention |
| 1-30 | 21 | 0.02 | −0.02 | invention |
| 1-31 | 20 | 0.03 | −0.04 | invention |
| 1-32 | 19 | 0.02 | −0.04 | invention |
| 1-33 | 20 | 0.03 | −0.02 | invention |
| 1-34 | 20 | 0.01 | −0.03 | invention |
| 1-35 | 22 | 0.01 | −0.02 | invention |
| 1-36 | 19 | 0.03 | 0     | invention |
| 1-37 | 18 | 0.03 | −0.01 | invention |
| 1-38 | 16 | 0.04 | −0.01 | invention |
| 1-39 | 17 | 0.06 | 0     | invention |
| 1-40 | 17 | 0.05 | 0     | invention |
| 1-41 | 18 | 0.06 | 0     | invention |
| 1-42 | 17 | 0.03 | −0.01 | invention |
| 1-43 | 19 | 0.04 | 0     | invention |
| 1-44 | 16 | 0.05 | 0     | invention |
| 1-45 | 17 | 0.05 | −0.01 | invention |
| 1-46 | 17 | 0.04 | 0     | invention |
| 1-47 | 19 | 0.02 | −0.01 | invention |
| 1-48 | 18 | 0.03 | 0     | invention |
| 1-49 | 18 | 0.06 | −0.01 | invention |

<Results>

In only the cases where the present hydrazide compounds were used as nucleating agent, the sensitive materials for argon laser scanner were able to achieve ultra-high contrast and high processing consistency under the development with the developer of low pH, and excellent storage stability as well.

EXAMPLE 3

<Production of Silver Halide Photosensitive Materials>

(i) Preparation of Emulsion B

Emulsion B was prepared in the same manner as Emulsion A, except that the emulsion was chemically sensitized at 60° C. with 1 mg/mole silver of a selenium sensitizer represented by the following structural formula, 1 mg/mole silver of sodium thiosulfate and 4 mg/mole silver of chloroauric acid so as to acquire the optimum sensitivity.

$$\left(\underset{3}{\underbrace{\bigcirc}}\right)-P=Se$$

(ii) Production of Coating Samples

Samples were produced in the same manner as in Example 2, except that the sensitizing dyes in the EM layer were replaced by $2.1 \times 10^{-4}$ mole/mole silver of Compound (S-3) illustrated below and Emulsion A was replaced by Emulsion B.

[Structure of Compound S-3: benzoxazole with N-(CH$_2$)$_2$SO$_3^\ominus$ substituent, connected via =CH—CH=C(CH$_3$)—CH= chain to a thiazolidinone-type ring with =S and N-CH$_2$COO$^\ominus$ 2Na$^\oplus$]

<Evaluation>

(1) Exposure and Development Processing

Each of the samples produced above was exposed to a xenon flash lamp having an emission time of $10^{-6}$ sec. through a step wedge via an interference filter having a peak at 633 nm, developed for 20 sec. at 35° C. with each of the developers A, B and C prepared in Example 2, fixed with the same fixer as used in Example 2, and further subjected to successive washing and drying operations. Herein, an auto processor, FG-680 AG, made by Fuji Photo Film Co., Ltd., was used. During the photographic processing, the replenisher volumes for each developer and the fixer, respectively, were controlled to 100 ml per m$^2$ of sample.

The high contrast characteristics, the dependence of sensitivity on pH of the developer, and the aging stability of each sensitive material were evaluated by the same methods as in Example 2, respectively.

<Results>

Similarly to the results obtained in Example 2, the sensitive materials for helium-neon laser scanner were able to achieve ultra-high contrast and high processing consistency under the development with the developer of low pH, and excellent storage stability as well, only when the present hydrazide compounds were used as nucleating agent.

EXAMPLE 4

<Production of Silver Halide Photosensitive Materials>

Samples were produced in the same manner as in Example 2, except that the sensitizing dyes in the EM layer were replaced by Compound (S-4) illustrated below.

(S-4)

[Structure of Compound S-4: H$_5$C$_2$—N substituted quinoline linked via =CH—CH=C(CH$_3$)—CH=CH— to a benzothiazolium with 5,6-dimethyl substituents and N-C$_2$H$_5$; counterion I$^-$]

<Evaluation>

Each of the samples produced above was exposed to a xenon flash lamp having an emission time of $10^{-6}$ sec. through a step wedge via an interference filter having a peak at 780 nm, developed for 20 sec. at 35° C. with each of the developers A, B and C prepared in Example 2, fixed with the same fixer as used in Example 2, and further subjected to successive In washing and drying operations. Herein, an auto processor, FG-680 AG, made by Fuji Photo Film Co., Ltd., was used. During the photographic processing, the replenisher volumes for each developer and the fixer, respectively, were controlled to 100 ml per m$^2$ of sample.

The high contrast characteristics, the dependence of sensitivity on pH of the developer, and the aging stability of each sensitive material were evaluated by the same methods as in Example 2, respectively.

<Results>

Similarly to the results obtained in Example 2, the sensitive materials for semiconductor laser scanner were able to achieve ultra-high contrast and high processing consistency under the development with the developer of low pH, and excellent storage stability as well, only when the present hydrazide compounds were used as nucleating agent.

EXAMPLE 5

<Production of Silver Halide Photosensitive Materials>

Samples were produced in the same manner as in Example 2, except that the sensitizing dyes in the EM layer were replaced by Compound (S-5) illustrated below.

(S-5)

[Structure of Compound S-5: 5-chlorobenzoxazole with N-(CH$_2$)$_3$SO$_3^\ominus$ linked via =CH—C(C$_2$H$_5$)=CH— to 5-chlorobenzoxazolium with N-(CH$_2$)$_3$SO$_3$Na]

<Evaluation>

Each of the samples produced above was exposed to a tungsten lamp of 3200° K through a step wedge, developed for 20 sec. at 35° C. with each of the developers A, B and C prepared in Example 2, fixed with the same fixer as used in Example 2, and further subjected to successive washing and drying operations. Herein, an auto processor, FG-680 AG, made by Fuji Photo Film Co., Ltd., was used. During the photographic processing, the replenisher volumes for each developer and the fixer, respectively, were controlled to 100 ml per m$^2$ of sample.

The high contrast characteristics, the dependence of sensitivity on pH of the developer, and the aging stability of each sensitive material were evaluated by the same methods as in Example 2, respectively.

<Results>

Similarly to the results obtained in Example 2, the sensitive materials for photographing use were able to achieve ultra-high contrast and high processing consistency under the development with the developer of low pH, and excellent storage stability as well, only when the present hydrazide compounds were used as nucleating agent.

EXAMPLE 6

<Production of Silver Halide Photosensitive Materials>

(i) Preparation of Emulsion C

To a 1.5% aqueous gelatin solution having the pH of 2.0 and containing sodium chloride, $3\times10^{-5}$ mole/mole silver of Compound Z illustrated below and $5\times10^3$ mole/mole silver of 4-hydroxy-6-methyl-1,3,3a,7-tetrazaindene, which was kept at 38° C., an aqueous solution of silver nitrate and an aqueous solution containing sodium chloride and $5\times10^{-5}$ mole/mole silver of $K_2Ru(NO)Cl_5$ were added simultaneously over a period of 3.5 minutes under the potential of 95 mV in accordance with a double jet method, thereby preparing core grains having an average size of 0.12 µm, and further those solutions in the same amounts as used above were added simultaneously over a period of 7 minutes in the same manner as described above. Thus, cubic silver chloride grains having an average size of 0.13 µm were obtained. (The variation coefficient thereof was 12%.)

Then, these grains were washed with water by the flocculation method well-known in the art to remove the soluble salts, and thereto gelatin was added. Further, 60 mg/mole silver of Compound F and 60 mg/mole silver of phenoxyethanol were added thereto as antiseptics, and then adjusted to pH 5.5 and pAg 7.5. The emulsion thus obtained was chemically sensitized at 60° C. for 60 minutes with $4\times10^{-5}$ mole/mole silver of chloroauric acid, $1\times10^{-5}$ mole/mole silver of the foregoing selenium sensitizer and $1\times10^{-5}$ mole/mole silver of sodium thiosulfate. Thereafter, the resulting emulsion was admixed with $1\times10^{-3}$ mole/mole silver of 4-hydroxy-6-methyl-1,3,3a,7-tetrazaindene as a stabilizer. (The final grains obtained were silver chloride grains having the pH of 5.7, the pAg of 7.5 and the Ru content of $5\times10^{-5}$ mole/mole silver.)

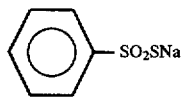

Compound Z (ii) Production of Coating Samples (Silver Halide Emulsion Layer)

The Emulsion C prepared above was admixed with the following compounds, and coated on a support provided with a subbing layer, which is described below, so as to have the gelatin coverage of 0.9 g/m² and the silver coverage of 2.75 g/m².

| | |
|---|---|
| Sodium salt of N-oleyl-N-methyltaurine | 19 mg/m² |
| Solid dispersion of hydrazide compound prepared in Example 1, as shown in Table 4 | 15 mg/m² (on basis of hydrazide compound) |
| Nucleation accelerator z | 20 mg/m² |
| Sodium-3-(5-mercaptotetrazole)benezenesulfonate | 11 mg/m² |
| Compound A | 13 mg/m² |
| Ascorbic acid | 1 mg/m² |
| Compound B | 15 mg/m² |
| Compound C | 70 mg/m² |
| Acetic acid | quantity required for adjustment of film pH to 5.2–6.0 |
| Compound D | 950 mg/m² |
| Compound E (hardener) | quantity to control swelling degree in water to 80% |

On the emulsion layer formed above, the following emulsion-protecting lower and upper layers were provided.

(Emulsion Protecting Lower Layer)

An aqueous gelatin solution having the following composition was applied at a gelatin coverage of 0.8 g/m².

| | |
|---|---|
| Gelatin (Ca⁺⁺ content: 2,700 ppm) | 0.8 g/m² |
| Compound F | 1 mg/m² |
| 1,5-Dihydroxy-2-benzaldoxime | 14 mg/m² |
| $C_2H_5SO_2SNa$ | 3 mg/m² |
| Compound C | 3 mg/m² |
| Sodium p-dodecylbenzenesulfonate | 7 mg/m² |
| Water-soluble dye Y | 25 mg/m² |

(Emulsion Protecting Upper Layer)

An aqueous gelatin solution having the following composition was applied at a gelatin coverage of 0.45 g/m².

| | |
|---|---|
| Gelatin (Ca⁺⁺ content: 2,700 ppm) | 0.45 g/m² |
| Amorphous silica matting agent (average particle size: 4.4 µm) | 40 mg/m² |
| Amorphous silica matting agent (average particle size: 3.6 µm) | 10 mg/m² |
| Compound F | 1 mg/m² |
| Compound C | 8 mg/m² |
| Solid disperse dye $G_1$ | 68 mg/m² |
| Liquid paraffin | 21 mg/m² |
| Potassium N-perfluorooctanesulfonyl-N-propylglycine | 5 mg/m² |
| Sodium p-dodecylbenzenesulfonate | 29 mg/m² |

Then, the following conductive layer and backing layer were applied simultaneously on the back side of the support.

(Conductive Layer)

An aqueous gelatin solution having the following composition was applied at a gelatin coverage of 0.06 g/m².

| | |
|---|---|
| $SnO_2$/Sb (mixing ratio: 9/1 by weight; average grain size: 0.25 µm) | 186 mg/m² |
| Gelatin (Ca⁺⁺ content: 2,700 ppm) | 0.06 g/m² |
| Sodium p-dodecylbenzenesulfonate | 13 mg/m² |
| Sodium dihexyl-α-sulfosuccinate | 12 mg/m² |
| Compound C | 12 mg/m² |
| Compound F | 1 mg/m² |

(Backing Layer)

An aqueous gelatin solution having the following composition was applied at a gelatin coverage of 1.94 g/m².

| | |
|---|---|
| Gelatin (Ca⁺⁺ content: 30 ppm) | 1.94 g/m² |
| Fine particles of polymethylmethacrylate (average particle size: 4.7µ) | 7 mg/m² |
| Compound H | 233 mg/m² |
| Compound I | 21 mg/m² |
| Compound G | 146 mg/m² |
| Compound F | 3 mg/m² |
| Sodium p-dodecylbenzenesulfonate | 68 mg/m² |
| Sodium dihexyl-α-sulfosuccinate | 21 mg/m² |
| $C_8F_{17}SO_3Li$ | 4 mg/m² |
| Potassium N-perfluorooctanesulfonyl-N-propylglycine | 6 mg/m² |
| Sodium sulfate | 177 mg/m² |
| Compound E (hardener) | quantity to control swelling degree in water to 90% |

(Support and Subbing Layer)

On both sides of a biaxially stretched polyethylene terephthalate support (thickness: 100 µm), first and second subbing layers having the following compositions were applied.

123

(First Subbing Layer)

| | |
|---|---|
| Core-Shell type vinylidene chloride copolymer (1) | 15 g |
| 2,4-Dichloro-6-hydroxy-s-triazine | 0.25 g |
| Fine particles of polystyrene (average particle size: 3μ) | 0.05 g |
| Compound M | 0.20 g |
| Colloidal silica (particle size: 70–100μ, Snowtex ZL, product of Nissan Chemical Industries, Ltd.) | 0.12 g |
| Water to make | 100 g |

A dispersion having the above composition was adjusted to pH 6 by the addition of 10% by weight of KOH, and applied so as to have a dry thickness of 0.9 μ by 2-minute drying at 180° C.

(Second Subbing Layer)

| | |
|---|---|
| Gelatin | 1 g |
| Methyl cellulose | 0.05 g |
| Compound J | 0.02 g |
| $C_{12}H_{25}O(CH_2CH_2O)_{10}H$ | 0.03 g |
| Compound F | $3.5 \times 10^{-3}$ g |
| Acetic acid | 0.2 g |
| Water to make | 100 g |

A solution having the above composition was applied on the foregoing first subbing layer so as to have a dry thickness of 0.1 μ by 2-minute drying at 170° C. Thus, the support provided with subbing layers was made.

Core-Shell Type Vinylidene Chloride Copolymer (1)

$$-(CH_2C)_{90}-(CH_2C)_4-(CH_2C)_4-(CH_2C)_1-(CH_2C)_1-$$

with substituents: Cl/Cl (VDC); CH₃/C=O/OCH₃ (MMA); H/C=O/OCH₃ (MA); H/CN (AN); H/C=O/OH (AA)

Core: VDC/MMA/MA (80% by weight)
Shell: VDC/AN/AA (20% by weight)
Average Particle Size: 70 nm Nucleation Accelerator Z

[structure: phenyl-pyridinium-(CH₂)₆-pyridinium-phenyl · 2Cl⁻]

Compound A

[benzotriazole-CONH-CH₂CH₂-N(C₂H₅)₂ structure]

Compound B

[di-tert-pentylphenyl-OCHCONHCH₂CH₂N(C₂H₅)₂ with C₂H₅ group]

124

-continued

Compound C $-(CH_2-CH)_n-$ with phenyl-SO₃K substituent

Compound D $-(CH_2CH)_{37}-(CH_2CH=CHCH_2)_{63}-$ with phenyl    core/shell = 50/50
<core: St/Bu = 47/63>

$-(CH_2CH)_{84}-(CH_2C(CH_3))_{16}-$ with phenyl and COO-CH₂CH₂-OCOCH₂COCH₃

<shell: St/AAEMA = 84/16>

Compound E $CH_2=CHSO_2CH_2CONH-CH_2/CH_2=CHSO_2CH_2CONH-CH_2$
$CH_2=CHSO_2CH_2CONH-CH_2$        $CH_2=$ 4/1
$CH_2=CHSO_2CH_2CONH-CH_2$ Compound F

[benzisothiazolin-3-one structure]

Compound G

[bis(dimethylamino-sulfonato-phenyl) ketone: NaO₃S and SO₃Na groups, N(CH₃)₂ groups]

Solid Disperse Dye G

[bis-pyrazolone methine dye with nC₄H₉ groups]

Compound H

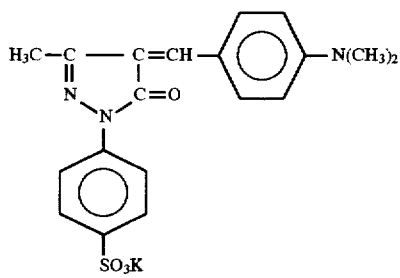

Water-soluble Dye Y

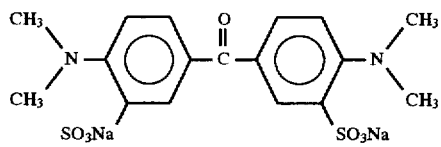

Compound I

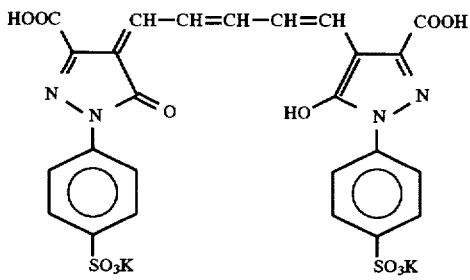

Compound J

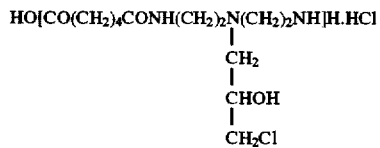

Additionally, the aforementioned layers to be provided on the above support were coated in the following manner, and dried under the condition described below:

<Coating Method>

On one side of the support provided with the subbing layers described above, the emulsion layer, the emulsion protecting lower layer and the emulsion protecting upper layer were arranged in that order using a simultaneous multilayer coating technique while each coating composition was kept at 35° C. and thereto a hardener solution was fed by means of a slide hopper system, and then passed through a cold-air setting zone (5° C.). Thereafter, the other side of the support was coated with the conductive layer and the backing layer in this order using the same simultaneous multilayer coating technique as described above while each coating composition was kept at 35° C. and thereto a hardener solution was fed by means of a slide hopper system, and passed through the cold-air setting zone (5° C.). Just after each passage through the setting zone, the layers coated were in a sufficiently set condition. Subsequently, both sides of the support was dried in a drying zone under the following condition. Additionally, during a period from the conclusion of the coating on the back side of the support to the start in winding up the coated material, the coated material was conveyed without touching with any matter, including rollers. The coating speed adopted therein was 120 m/min.

<Drying Condition>

After the setting operation, the coated material was dried with 30° C. drying air until the proportion of water to gelatin came to 800% by weight, and further with 35° C.–30% drying air until the proportion of water to gelatin came to 200% by weight. Successively, the thus dried material was exposed to air until the surface temperature thereof came to 34° C. (At this point, the drying operation was taken as completed.) After a lapse of 30 seconds therefrom, the material was further dried for 1 minute with 48° C.–2% air. As for the drying time, the period from the start of drying to the state of 800% by weight with respect to the proportion of water to gelatin was 50 seconds, the period between the 800% by weight and 200% by weight states with respect to the proportion of water to gelatin was 35 seconds, and the period from the state of 200% by weight with respect to the proportion of water to gelatin to the completion of drying was 5 seconds.

The thus produced photosensitive material was wound up under the atmosphere of 23° C.–40%, and then cut under the same atmosphere, placed in a barrier bag which had undergone a humidity control for 6 hours, and allowed to stand for 8 hours in the atmosphere of 40° C.–10%. Thereafter, the resultant material was sealed in the barrier bag together with the cardboard which had undergone a 2-hour humidity control under the condition of 23° C.–40%. The humidity inside the barrier bag was 40%.

In the aforementioned manner, the samples as shown in Table 4 were produced.

TABLE 4

| Sample No. | Solid Dispersion of Hydrazide Compound | Remark |
|---|---|---|
| 2-1 | K - 1 | comparison |
| 2-2 | K - 2 | comparison |
| 2-3 | K - 3 | comparison |
| 2-4 | K - 4 | comparison |
| 2-5 | K - 5 | comparison |
| 2-6 | K - 6 | comparison |
| 2-7 | K - 7 | comparison |
| 2-8 | K - 8 | comparison |
| 2-9 | K - 9 | comparison |
| 2-10 | K - 10 | comparison |
| 2-11 | K - 11 | comparison |
| 2-12 | K - 12 | comparison |
| 2-13 | K - 13 | comparison |
| 2-14 | K - 27 | invention |
| 2-15 | K - 28 | invention |
| 2-16 | K - 29 | invention |
| 2-17 | K - 30 | invention |
| 2-18 | K - 31 | invention |
| 2-19 | K - 32 | invention |
| 2-20 | K - 33 | invention |
| 2-21 | K - 34 | invention |
| 2-22 | K - 35 | invention |
| 2-23 | K - 36 | invention |
| 2-24 | K - 37 | invention |
| 2-25 | K - 38 | invention |
| 2-26 | K - 39 | invention |
| 2-27 | K - 40 | invention |
| 2-28 | K - 41 | invention |
| 2-29 | K - 42 | invention |
| 2-30 | K - 43 | invention |
| 2-31 | K - 44 | invention |
| 2-32 | K - 45 | invention |
| 2-33 | K - 46 | invention |
| 2-34 | K - 47 | invention |
| 2-35 | K - 57 | invention |
| 2-36 | K - 58 | invention |
| 2-37 | K - 59 | invention |
| 2-38 | K - 60 | invention |
| 2-39 | K - 61 | invention |

TABLE 4-continued

| Sample No. | Solid Dispersion of Hydrazide Compound | Remark |
|---|---|---|
| 2-40 | K - 62 | invention |
| 2-41 | K - 63 | invention |
| 2-42 | K - 64 | invention |
| 2-43 | K - 65 | invention |
| 2-44 | K - 66 | invention |
| 2-45 | K - 67 | invention |
| 2-46 | K - 68 | invention |
| 2-47 | K - 69 | invention |
| 2-48 | K - 70 | invention |

<Evaluation>

Each of the samples was exposed by means of a printer, P-627FM (made by Dainippon Screen Mfg. Co., Ltd.) through a step wedge. Then, each sample was developed for 20 sec. at 35° C. with each of the developers A, B and C prepared in Example 2, fixed with the same fixer as used in Example 2, and further subjected to successive washing and drying operations. Herein, an auto processor, FG-680 AG, made by Fuji Photo Film Co., Ltd., was used. During the photographic processing, the replenisher volumes for each developer and the fixer, respectively, were controlled to 100 ml per m² of sample.

The high contrast characteristics, the dependence of sensitivity on pH of the developer, and the aging stability of each sensitive material were evaluated by the same methods as in Example 2, respectively.

The results obtained are shown in Table 5.

TABLE 5

| Sample No. | Gamma value | pH Dependence of developer ($\Delta S_{1.5}$) | Aging stability of sensitive material ($\Delta S_{1.5}$) | Remark |
|---|---|---|---|---|
| 2-1 | 9 | 0.11 | -0.01 | comparison |
| 2-2 | 13 | 0.29 | -0.15 | comparison |
| 2-3 | 12 | 0.26 | -0.11 | comparison |
| 2-4 | 11 | 0.15 | -0.08 | comparison |
| 2-5 | 13 | 0.16 | -0.10 | comparison |
| 2-6 | 12 | 0.17 | -0.09 | comparison |
| 2-7 | 13 | 0.15 | -0.09 | comparison |
| 2-8 | 13 | 0.28 | -0.11 | comparison |
| 2-9 | 12 | 0.26 | -0.11 | comparison |
| 2-10 | 7 | 0.10 | -0.06 | comparison |
| 2-11 | 12 | 0.25 | -0.12 | comparison |
| 2-12 | 10 | 0.15 | -0.06 | comparison |
| 2-13 | 11 | 0.16 | -0.09 | comparison |
| 2-14 | 17 | 0.07 | -0.01 | invention |
| 2-15 | 18 | 0.06 | -0.02 | invention |
| 2-16 | 18 | 0.09 | -0.01 | invention |
| 2-17 | 16 | 0.08 | -0.01 | invention |
| 2-18 | 15 | 0.08 | -0.02 | invention |
| 2-19 | 17 | 0.07 | -0.02 | invention |
| 2-20 | 17 | 0.06 | -0.01 | invention |
| 2-21 | 16 | 0.06 | -0.01 | invention |
| 2-22 | 18 | 0.07 | -0.01 | invention |
| 2-23 | 18 | 0.08 | -0.02 | invention |
| 2-24 | 17 | 0.06 | -0.02 | invention |
| 2-25 | 18 | 0.06 | -0.01 | invention |
| 2-26 | 18 | 0.02 | -0.01 | invention |
| 2-27 | 21 | 0.01 | -0.02 | invention |
| 2-28 | 20 | 0.01 | -0.02 | invention |
| 2-29 | 19 | 0.02 | -0.01 | invention |
| 2-30 | 19 | 0.03 | -0.01 | invention |
| 2-31 | 20 | 0.03 | -0.01 | invention |
| 2-32 | 19 | 0.03 | -0.02 | invention |
| 2-33 | 18 | 0.01 | -0.01 | invention |
| 2-34 | 21 | 0.01 | -0.01 | invention |
| 2-35 | 18 | 0.03 | 0 | invention |
| 2-36 | 17 | 0.04 | 0 | invention |
| 2-37 | 15 | 0.06 | 0 | invention |
| 2-38 | 16 | 0.05 | -0.01 | invention |
| 2-39 | 16 | 0.05 | -0.01 | invention |
| 2-40 | 18 | 0.04 | 0 | invention |
| 2-41 | 16 | 0.05 | -0.01 | invention |
| 2-42 | 17 | 0.03 | 0 | invention |
| 2-43 | 17 | 0.04 | -0.01 | invention |
| 2-44 | 15 | 0.06 | -0.01 | invention |
| 2-45 | 18 | 0.05 | -0.01 | invention |
| 2-46 | 18 | 0.04 | 0 | invention |
| 2-47 | 16 | 0.05 | 0 | invention |
| 2-48 | 17 | 0.05 | -0.01 | invention |

<Results>

Only when the present hydrazide compounds were used as nucleating agent, the photosensitive materials for illuminated room processing for dot to dot work were able to achieve ultra-high contrast and high processing consistency under the development with the developer of low pH, and excellent storage stability as well.

EXAMPLE 7

The samples prepared in Examples 2, 3, 4, 5 and 6 were subjected to the same exposure and development processing operations as in Examples 2, 3, 4, 5 and 6, respectively, except that Developer D or E having the following composition was used in place of Developer A and Fixer B was used in place of Fixer A. Similarly to the results obtained in Examples 2 to 6, the photographic photosensitive materials were able to achieve ultra-high contrast and high processing consistency under the development with the developer of low pH, and excellent storage stability as well, only when the present hydrazide compounds were incorporated therein as nucleating agent. Additionally, the developers used for examining the dependence of the sensitivity on pH of the developer were those obtained by adding acetic acid to each of Developers D and E so as to lower the pH by 0.3 and those obtained by adding sodium hydroxide to each of Developers D and E so as to raise the pH by 0.3.

| <Developer D> | |
|---|---|
| Potassium hydroxide | 40.0 g |
| Diethylenetriaminepentaacetic acid | 2.0 g |
| Potassium carbonate | 60.0 g |
| Sodium metabisulfite | 70.0 g |
| Potassium bromide | 7.0 g |
| Hydroquinone | 40.0 g |
| 5-Methylbenzotriazole | 0.35 g |
| 4-Hydroxymethyl-4-methyl-1-phenyl-3-pyrazolidone | 1.50 g |
| Sodium 2-mercaptobenzimidazole-5-sulfonate | 0.30 g |
| Sodium 3-(5-mercapoptetrazole-1-yl)benzenesulfonate | 0.10 g |
| Sodium erythorbate | 6.0 g |
| Diethylene glycol | 5.0 g |
| Water to make | 1 l |
| pH adjusted by addition of KOH to | 10.65 |

<Developer E>

Water was added to the following solid-type developing kit to prepare 10 liter of Developer E.

Solid ingredients to constitute the developing kit were mixed in amounts corresponding to their respective concentrations in 10 liter of Developer E, and then loaded into a container made of high density polyethylene (having the average thickness of 500 μm, partly being 200–1.000 μm in thickness).

The composition of 10 liter of Developer E and the forms of raw materials used are shown in Table 6.

TABLE 6

| Ingredient | Form of Raw Material | Amount used |
|---|---|---|
| Sodium hydroxide (purity: 99.5%) | beads | 115 g |
| Potassium sulfite | raw powder | 718 g |
| Sodium sulfite | raw powder | 350 g |
| Mixture of | briquette | |
| diethylenetriaminepentaacetic acid, | | 20 g |
| 5-methylbenzotriazole, | | 3.5 g |
| sodium 2-mercaptobenzimidazole-5-sulfonate, | | 1.0 g |
| potassium bromide, | | 66 g |
| 4-hydroxymethyl-4-methyl-1-phenyl-3-pyrazolidone, and | | 15 g |
| sodium erythorbate | | 60 g |
| Potassium carbonate | raw powder | 620 g |
| Hydroquinone | briquette | 400 g |
| Total weight | | 2,336 g |
| Proportion (by weight) of alkalis | | 4.9% |
| pH | | 10.6 |

As for the forms of raw materials, general industrial products were employed as raw powders as they were, and the beads of alkali metal salt used are also commercial products.

The raw material having the form of briquette was prepared by being compressed by means of a briquetting machine to be shaped into irregular rugby ball-like forms measuring 4–6 mm in length, and then being crushed. As for the ingredients used in small amounts, they were blended together, and then shaped into a form of briquette.

<Fixer B>

Water was added to the following solid chemicals and liquid chemicals to prepare 10 liter of Fixer B.

More specifically, both the solid chemicals and the liquid chemicals according to the formula described below were loaded into a container made of high density polyethylene (having the average thickness of 500 μm, partly being 200–1.000 μm in thickness). The volume after dissolving all the chemicals in water was adjusted to 10 liter, and the pH of the fixer prepared was 4.85.

| (Solid part) | |
|---|---|
| Ammonium thiosulfate | 1200 g |
| Sodium thiosulfate | 150 g |
| Sodium acetate | 400 g |
| Sodium metabisulfite | 200 g |
| (Liquid part) | |
| Aluminum sulfate (27%) | 300 g |
| Sulfuric acid (75%) | 30 g |
| Sodium gluconate | 20 g |
| EDTA | 0.3 g |
| Citric acid | 40 g |

Additionally, the ingredients constituting the solid part were mixed, and then loaded into the container.

EXAMPLE 8

Photographic photosensitive materials were prepared in the same manner as in Example 2, except that the powders of hydrazide compounds shown in Table 7 were each dissolved in methanol and then added to the coating composition, and then subjected to the same exposure and photographic processing operations as in Example 2, followed by evaluation with respect to the high contrast characteristics and the dependence of the sensitivity on pH of the developer.

The results obtained are also shown in Table 7.

TABLE 7

| Sample No. | Hydrazide compound | Gamma value | Dependence on pH of developer ($\Delta S_{1.5}$) | Remark |
|---|---|---|---|---|
| 3-1 | Comparative Compound 1-1 | 14 | 0.22 | comparison |
| 3-2 | Comparative Compound 1-2 | 15 | 0.26 | comparison |
| 3-3 | Comparative Compound 1-3 | 12 | 0.15 | comparison |
| 3-4 | Comparative Compound 1-4 | 14 | 0.16 | comparison |
| 3-5 | Comparative Compound 2-2 | 15 | 0.25 | comparison |
| 3-6 | Comparative Compound 2-3 | 16 | 0.14 | comparison |
| 3-7 | Comparative Compound 2-4 | 14 | 0.26 | comparison |
| 3-8 | Comparative Compound 3-2 | 12 | 0.25 | comparison |
| 3-9 | Comparative Compound 3-3 | 16 | 0.13 | comparison |
| 3-10 | Comparative Compound 3-4 | 16 | 0.16 | comparison |
| 3-11 | Comparative Compound 3-5 | 16 | 0.15 | comparison |
| 3-12 | 1-1c | 22 | 0.04 | invention |
| 3-13 | 1-2c | 23 | 0.05 | invention |
| 3-14 | 1-3c | 19 | 0.04 | invention |
| 3-15 | 1-4c | 19 | 0.06 | invention |
| 3-16 | 1-12c | 20 | 0.04 | invention |
| 3-17 | 1-13c | 21 | 0.06 | invention |
| 3-18 | 1-15c | 20 | 0.05 | invention |
| 3-19 | 1-16c | 22 | 0.07 | invention |
| 3-20 | 1-17c | 20 | 0.04 | invention |
| 3-21 | 1-18c | 19 | 0.06 | invention |
| 3-22 | 1-19c | 19 | 0.05 | invention |
| 3-23 | 1-31c | 22 | 0.05 | invention |
| 3-24 | 2-1b | 23 | 0.01 | invention |
| 3-25 | 2-2b | 24 | 0 | invention |
| 3-26 | 2-3b | 23 | 0 | invention |
| 3-27 | 2-4b | 24 | 0.01 | invention |
| 3-28 | 2-5c | 22 | 0.02 | invention |
| 3-29 | 2-6c | 21 | 0.01 | invention |
| 3-30 | 2-14c | 21 | 0.01 | invention |
| 3-31 | 2-16c | 23 | 0 | invention |
| 3-32 | 2-18c | 24 | 0 | invention |
| 3-33 | 3-1c | 22 | 0.02 | invention |
| 3-34 | 3-2c | 19 | 0.02 | invention |
| 3-35 | 3-3c | 19 | 0.02 | invention |
| 3-36 | 3-4c | 19 | 0.04 | invention |
| 3-37 | 3-7c | 18 | 0.03 | invention |
| 3-38 | 3-9c | 20 | 0.05 | invention |
| 3-39 | 3-10c | 20 | 0.01 | invention |
| 3-40 | 3-11b | 21 | 0.02 | invention |
| 3-41 | 3-12b | 18 | 0.03 | invention |
| 3-42 | 3-13b | 18 | 0.02 | invention |
| 3-43 | 3-15b | 21 | 0.02 | invention |
| 3-44 | 3-18b | 20 | 0.03 | invention |
| 3-45 | 3-21b | 20 | 0.02 | invention |
| 3-46 | 3-22b | 21 | 0.04 | invention |

<Results>

Similarly to the results obtained in Example 2, the photographic photosensitive materials were able to achieve ultra-high contrast and high processing consistency under the development with the developer of low pH only when the present hydrazide compounds were used as nucleating agent.

EXAMPLE 9

A solution containing 1.0 g of each hydrazine nucleating agent shown in Table 1 (each compound contained in Solid Dispersions K-8 to K-84), 6.0 g of poly(N-tert-butylacrylamide) and 50 ml of ethyl acetate was heated to 60° C. to dissolve the compounds completely. The resultant solution was added to 120 ml of an aqueous solution containing 12 g of gelatin and 0.7 g of sodium dodecylbenzenesulfonate, and stirred with a homogenizer (manufactured by Nippon Seiki Manufacturing Co., Ltd.) at a high rotational speed to obtain a emulsion dispersion of fine particles having an average particle diameter of about 0.2 μm. Then, the emulsion dispersion was heated and distilled under reduced pressure to remove ethyl acetate. Thus, a hydrazine nucleating agent was obtained. A photographic photosensitive material was prepared in the same manner as in Example 3, except for using the hydrazine nucleating agent thus obtained. The photographic characteristics of the photographic photosensitive material was evaluated in the same manner as in Example 3. As a result, photographic photosensitive materials for helium-neon laser scanner were able to achieve ultra-high contrast and high processing consistency under the development with the developer of low pH, and excellent storage stability as well, only when the present hydrazide compounds were used as nucleating agent.

While the invention has been described in detail and with reference to specific embodiments thereof, it will be apparent to one skilled in the art that various changes and modifications can be made therein without departing from the spirit and scope thereof.

What is claimed is:

1. A hydrazine compound represented by the following formula (I):

wherein A represents a 3- to 7-membered heterocyclic group which does not contain a quaternarized nitrogen atom, a condensed polycyclic aromatic group or a group formed by connecting at least two aromatic groups to each other, B represents a group represented by the following formula (I-B) or (II-B), and b represents an integer from 2 to 6;

 (I-B)

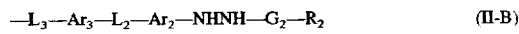 (II-B)

wherein each of $G_1$ and $G_2$ represents a carbonyl group, an oxalyl group, a sulfonyl group or a phosphoryl group; each of $R_1$ and $R_2$ represents a hydrogen atom or a blocking group; each of $Ar_1$, $Ar_2$ and $Ar_3$ represents an aromatic group or an aromatic heterocyclic group; each of $L_1$, $L_2$ and $L_3$ represents a linkage group; and $L_1$ is not a carbamoyl group when the group represented by A is a heterocyclic group.

2. A silver halide photographic photosensitive material comprising a hydrazide compound represented by the formula (I):

A—(B)$_b$ (I)

wherein A represents a 3- to 7-membered heterocyclic group which does not contain a quaternarized nitrogen atom, a condensed polycyclic aromatic group or a group formed by connecting at least two aromatic groups to each other, B represents a group represented by the following formula (I-B) or (II-B), and b represents an integer from 2 to 6;

 (I-B)

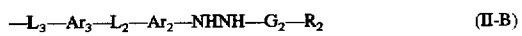 (II-B)

wherein each of $G_1$ and $G_2$ represents a carbonyl group, an oxalyl group, a sulfonyl group or a phosphoryl group; each of $R_1$ and $R_2$ represents a hydrogen atom or a blocking group; each of $Ar_1$, $Ar_2$ and $Ar_3$ represents an aromatic group or an aromatic heterocyclic group; each of $L_1$, $L_2$ and $L_3$ represents a linkage group; $L_1$ is not a carbamoyl group when the group represented by A is a heterocyclic group.

* * * * *